United States Patent
Reuling et al.

(10) Patent No.: US 10,645,890 B2
(45) Date of Patent: May 12, 2020

(54) **INTROGRESSION OF A YIELD QTL IN *CUCUMIS SATIVUS* PLANTS**

(71) Applicant: NUNHEMS B.V., Nunhem (NL)

(72) Inventors: Gerhard T. M. Reuling, Heythuysen (NL); Peter Arnold Gijsbert Kraan, Buggenum (NL); Frank Beenders, Roggel (NL); Marion Van de Wal, Best (NL); Freddy Hermans, Sevenum (NL); Hans-Peter Koelewijn, Veenendaal (NL); Steven D. Tanksley, Ithaca, NY (US); Alexandra M. Casa, Ithaca, NY (US); Gulay Cangal, Neer (NL)

(73) Assignee: NUNHEMS B.V., Nunhem (NL)

( * ) Notice: Subject to any disclaimer, the term of this patent is extended or adjusted under 35 U.S.C. 154(b) by 17 days.

(21) Appl. No.: 15/572,083

(22) PCT Filed: May 3, 2016

(86) PCT No.: PCT/EP2016/059829
§ 371 (c)(1),
(2) Date: Nov. 6, 2017

(87) PCT Pub. No.: WO2016/177696
PCT Pub. Date: Nov. 10, 2016

(65) Prior Publication Data
US 2018/0288960 A1    Oct. 11, 2018

(30) Foreign Application Priority Data
May 7, 2015 (EP) .................................... 15166819

(51) Int. Cl.
*A01H 6/34*     (2018.01)
*A01H 5/08*     (2018.01)
*A01H 1/04*     (2006.01)
*C12Q 1/6895*   (2018.01)
*A01H 1/00*     (2006.01)

(52) U.S. Cl.
CPC .............. *A01H 6/346* (2018.05); *A01H 1/00* (2013.01); *A01H 1/04* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 8,710,303 B2    4/2014  Crienen et al.
2010/0313291 A1  12/2010  De Haan et al.

FOREIGN PATENT DOCUMENTS

WO    WO 2009/059777 A1    5/2009
WO    WO 2009/082222 A1    7/2009
WO    WO-2009082222 A1 *   7/2009    ............... A01H 1/04

OTHER PUBLICATIONS

Fazio et al 2003 Theor Appl Genet 107:864-874 (Year: 2003).*
Allen et al., "Transcript-specific, single-nucleotide polymorphism discovery and linkage analysis in hexaploid bread wheat (*Triticum aestivum* L.)," Plant Biotechnology, 2011, J. 9, pp. 1086-1099.
European Search Report issued in European Patent Application No. 15166819, dated Sep. 29, 2015 (10 pages).
Fan et al., "Population development by phenotypic selection with subsequent marker-assisted selection for line extraction in cucumber (*Cucumis sativus* L.)," Theor Appl Genet, 2006, vol. 112, pp. 843-855.
Fazio et al., "Genetic mapping and QTL analysis of horticultural traits in cucumber (*Cucumis sativus* L.) using recombinant inbred lines", Theor Appl Genet, 2003, vol. 107, pp. 864-874.
Henikoff et al., "Amino acid substitution matrices from protein blocks," PNAS, 1992, vol. 89, pp. 10915-10919.
Huang et al., "The genome of the cucumber, *Cucumis sativus* L.", Nature Genetics, 2009, vol. 41, No. 12, pp. 1275-1283.
International Search Report and Written Opinion issued in International Patent Application No. PCT/EP2016/059829, dated Aug. 1, 2016 (15 pages).
Ji et al., "Ty-3, a begomovirus resistance locus near the Tomato yellow leaf curl virus resistance locus. Ty-1 on chromosome 6 of tomato", Mol. Breeding, 2007, vol. 20, pp. 271-284.
Qi et al., "A genomic variation map provides insights into the genetic basis of cucumber domestication and diversity," Nature Genetics, Dec. 2013, vol. 45, No. 12, pp. 1510-1518.
Shetty et al., "Screening the Cucumber Germplasm Collection for Fruit Yield and Quality," CropSci., 2002, vol. 42, pp. 2174-2183.
Tatlioglu, "Cucumis sativus L.," Cucumber Chapter 13, 2012, pp. 197-234.
Verlaan et al., "Chromosomal rearrangements between tomato and Solanum chilense hamper mapping and breeding of the TYLCV resistance gene Ty-1", Plant Journal, 2011, vol. 68, pp. 1093-1103.
Wei et al., "An SNP-based saturated genetic map and QTL analysis of fruit-related traits in cucumber using specific-length amplified fragment (SLAF) sequencing", BMC Genomics, 2014, vol. 15, No. 11, pp. 1-10.

* cited by examiner

*Primary Examiner* — Brent T Page
(74) *Attorney, Agent, or Firm* — Arent Fox LLP

(57) ABSTRACT

The present invention relates to cultivated cucumber plants comprising a yield QTL on chromosome 3 of their genome, and to methods for generating such plants, and their use.

24 Claims, No Drawings

Specification includes a Sequence Listing.

SEQUENCE LISTING

<160> NUMBER OF SEQ ID NOS: 27

<210> SEQ ID NO 1
<211> LENGTH: 150
<212> TYPE: DNA
<213> ORGANISM: Cucumis sativus
<220> FEATURE:
<221> NAME/KEY: SNP1
<222> LOCATION: (75)..(75)

<400> SEQUENCE: 1
ttaaaacaac aataaaaaca gacatgcagc atgcagcata ctaatgatat cactgagaaa    60
aacaaagccc ccgttggaaa aatcaaaaac aatatttcaa aaagaccagt aaaaagataa    120
gcgaatagag aataaatgaa aaaatataag                                    150

<210> SEQ ID NO 2
<211> LENGTH: 150
<212> TYPE: DNA
<213> ORGANISM: Cucumis sativus
<220> FEATURE:
<221> NAME/KEY: SNP2
<222> LOCATION: (75)..(75)

<400> SEQUENCE: 2
ttcactcaca ttytgcccct gaatatagct aacgggaaag taacatccat agtgacaaag    60
tatttcctgg acgataggtg aaaacattta taaccatgct ggtgaaaggg atacccaaca   120
aacacamatg yctgagctcg atgggtaaat                                    150

<210> SEQ ID NO 3
<211> LENGTH: 150
<212> TYPE: DNA
<213> ORGANISM: Cucumis sativus
<220> FEATURE:
<221> NAME/KEY: SNP3
<222> LOCATION: (75)..(75)

<400> SEQUENCE: 3
caaaagatat ggatcaaktt tgaggtcata ttaaaaaaat gaacttcctt tagcttagac    60
cacatttaca aatgtgtaac atagtttgat tgttttttct ttaatcatat ttcttaatat   120
tacaaataac tcattaactc kaacattaaa                                    150

<210> SEQ ID NO 4
<211> LENGTH: 150
<212> TYPE: DNA
<213> ORGANISM: Cucumis sativus
<220> FEATURE:
<221> NAME/KEY: SNP4
<222> LOCATION: (75)..(75)

<400> SEQUENCE: 4
ccacttctta aaaataaatg aaaagaggca tttggtgtta cctgtccaca tgtcttgact    60
tcacgaatat cacttgatac ttgatgttcg actactcggt gcatgctact caacacacaa   120
ttcctcgtta catgttttac aataaacaat                                    150

<210> SEQ ID NO 5
<211> LENGTH: 150
<212> TYPE: DNA
<213> ORGANISM: Cucumis sativus
<220> FEATURE:
<221> NAME/KEY: SNP5
<222> LOCATION: (75)..(75)

<400> SEQUENCE: 5
ctttatgtgt ggagcatttt atccatacat atatttgaag aaaaaactaa ttaaaagtac    60
ctcacatcac aatcgtgttc aaagtgtatt taaattacaa ttttttttagt gccatggtta   120 gaggagcttt aatttatttt tatgagtaga                                    150

<210> SEQ ID NO 6
<211> LENGTH: 150
<212> TYPE: DNA
<213> ORGANISM: Cucumis sativus
<220> FEATURE:
<221> NAME/KEY: SNP6

<222> LOCATION: (75)..(75)

<400> SEQUENCE: 6
ttaaacttgg acttgaattg ggttatgact tccgttgtag gattgctcat tgactgttca    60
acaactcgaa cacttttca atatcattca gtgtaaaaga atgtttcatg ttaaagaact    120
tttgcgttgt tgttggtgca ttacatccac                                    150

<210> SEQ ID NO 7
<211> LENGTH: 150
<212> TYPE: DNA
<213> ORGANISM: Cucumis sativus
<220> FEATURE:
<221> NAME/KEY: SNP7
<222> LOCATION: (75)..(75)

<400> SEQUENCE: 7
attatgcgaa caaccgttac taatccattt ctatataaac aagaggtccc ataattaacc    60
tttgaggtac actttgaact tcctatgctc tctggctctc tctaaacaat gactaacttg    120
atgttggagt gttgatgccc aaccaccaca                                    150

<210> SEQ ID NO 8
<211> LENGTH: 150
<212> TYPE: DNA
<213> ORGANISM: Cucumis sativus
<220> FEATURE:
<221> NAME/KEY: SNP8
<222> LOCATION: (75)..(75)

<400> SEQUENCE: 8
attatgcgaa camccgttac taatccattt ctatataaac aagaggtccc ataattaacc    60
tttgaggtac actttgaact tcctatgctc tctggctctc tctaaacaat gactaacttg    120
atgttggagt gttgatgccc aaccaccaca                                    150

<210> SEQ ID NO 9
<211> LENGTH: 150
<212> TYPE: DNA
<213> ORGANISM: Cucumis sativus
<220> FEATURE:
<221> NAME/KEY: SNP9
<222> LOCATION: (75)..(75)

<400> SEQUENCE: 9
atttcaatct cttctaaaca aggaaattat ttgtaccaga tgagagttct ggaagttgaa    60
aagtgatctc ataacttcaa caaagaagag ttacttcgag ttatcgttta aaaattatat    120
attcgaaagg tactcatact cgagaacatt                                    150

<210> SEQ ID NO 10
<211> LENGTH: 150
<212> TYPE: DNA
<213> ORGANISM: Cucumis sativus
<220> FEATURE:
<221> NAME/KEY: SNP10
<222> LOCATION: (75)..(75)

<400> SEQUENCE: 10
ctcratcttc ttcttttctt ttatctaata aaacctaaaa gaagaagata gggtttaggg    60
tatcatttgg tttcctacgg ttattgtaat tgtttagagt tgatcgctaa ttgtaacaat    120
aattgtgaca rattcatatt tctcaaactg                                    150

```
<210> SEQ ID NO 11
<211> LENGTH: 150
<212> TYPE: DNA
<213> ORGANISM: Cucumis sativus
<220> FEATURE:
<221> NAME/KEY: SNP11
<222> LOCATION: (75)..(75)

<400> SEQUENCE: 11
gtttctgtct gctaataacc ttggaattct tttgtcatac tcatacaaga ctcaacaata      60
atttgacttt ctagtatgga ttgatacgga agattagatg ctttatgttt gcaaatgata     120
aattgcaacc tattagttct cgtctcttca                                      150

<210> SEQ ID NO 12
<211> LENGTH: 150
<212> TYPE: DNA
<213> ORGANISM: Cucumis sativus
<220> FEATURE:
<221> NAME/KEY: SNP12
<222> LOCATION: (75)..(75)

<400> SEQUENCE: 12
acaagagttt aaaaggccac aatgcaaggc caaacacctt ttcactattt agaaaagctg      60
atttagtatt aaacataata gaggcgtcaa tcttccattt aaggtgatcc gggcaatcaa     120
gaggartcca agaattaaga atttccagca                                      150

<210> SEQ ID NO 13
<211> LENGTH: 150
<212> TYPE: DNA
<213> ORGANISM: Cucumis sativus
<220> FEATURE:
<221> NAME/KEY: SNP13
<222> LOCATION: (75)..(75)

<400> SEQUENCE: 13
caatgaacaa ttggggatta gacaaaaaga gaagaagcac aatcaaggag tattagtttta     60 tttaaggaag gaggtcactc aagagtcaaa caaacgtaaa accaggtcct ttcattacaa     120
caataatgac aaactcattg aaatgataca                                      150

<210> SEQ ID NO 14
<211> LENGTH: 150
<212> TYPE: DNA
<213> ORGANISM: Cucumis sativus
<220> FEATURE:
<221> NAME/KEY: SNP14
<222> LOCATION: (75)..(75)

<400> SEQUENCE: 14
tgtttggcct cttactggga ttctatttaa aatatttcct tcctgtatga tgactacttt      60
tgtttcttcc tcccatcgaa attttttgtg tgttatctga caagggaaaa gaaatttgca     120
aactcgttcc ttcctgttca tgattatgga                                      150

<210> SEQ ID NO 15
<211> LENGTH: 150
<212> TYPE: DNA
<213> ORGANISM: Cucumis sativus
<220> FEATURE:
<221> NAME/KEY: SNP15
<222> LOCATION: (75)..(75)

<400> SEQUENCE: 15
tccaaccatc acttcctcga tgcactgcaa tagaacttct cgtttcacaa ctccgtcgct      60
```

```
gttagcaaga gcttcgagac ctactttcca gacatcggtg atgaacttag cgtttgttgt    120
ttggtcagtc catccaggca ctgtgaccat                                     150

<210> SEQ ID NO 16
<211> LENGTH: 150
<212> TYPE: DNA
<213> ORGANISM: Cucumis sativus
<220> FEATURE:
<221> NAME/KEY: SNP16
<222> LOCATION: (75)..(75)

<400> SEQUENCE: 16
ttctcactta aaatttcagt tccttcattt tgaaattttg ttcaatttta actcatagtg    60
taagattcaa atcacgagtc accttaggcg ataaaaggat tatatgaaga actctcacct   120
cgagaagagg cttacttcat caaaaaataa                                     150

<210> SEQ ID NO 17
<211> LENGTH: 150
<212> TYPE: DNA
<213> ORGANISM: Cucumis sativus
<220> FEATURE:
<221> NAME/KEY: SNP17
<222> LOCATION: (75)..(75)

<400> SEQUENCE: 17
tgcactttga accttgcaca ttgcttgtat tcacaaattt cagaactggc tctttataat    60
tccacaggca taatgcactc atgaacaaat taaacaacta acctagaaat gtattcctct   120
cctctggttt tttgtttgta tgtgcaagtg                                     150

<210> SEQ ID NO 18
<211> LENGTH: 150
<212> TYPE: DNA
<213> ORGANISM: Cucumis sativus
<220> FEATURE:
<221> NAME/KEY: SNP18
<222> LOCATION: (75)..(75)

<400> SEQUENCE: 18
actgccattg caacctcaag ctttgcagcg atgtggtttg agatgcaagc ggtgcagaat    60
gtatgtgtac ataccctgtt ggtgaacatt tgggaatggg attttgcgtc tgtacagatt   120
gaacagagaa gttgggaggt agaagagtgg                                     150

<210> SEQ ID NO 19
<211> LENGTH: 150
<212> TYPE: DNA
<213> ORGANISM: Cucumis sativus
<220> FEATURE:
<221> NAME/KEY: SNP19
<222> LOCATION: (75)..(75)

<400> SEQUENCE: 19
ttcgtgccaa aacgcccaat tttgagcttc cagctggctg gacagtggct caaactcttc    60
caaaattcaa atctggtatc aaaatgtaat gggtaatgtt gttaaactca agtctaactt   120
aatggatatt caaaatttca agaaaactca                                     150

<210> SEQ ID NO 20
<211> LENGTH: 150
<212> TYPE: DNA
<213> ORGANISM: Cucumis sativus
<220> FEATURE:
```

```
<221> NAME/KEY: SNP20
<222> LOCATION: (75)..(75)

<400> SEQUENCE: 20
attgggaact tttggagctg aggttgctga tttggtcgaa ggggtaagat gctgcaccat      60
ccacactttc tttgccatca aatagatggc ttaggcatag aatcataatg gaaaaactta    120
ttatgttttc ttttgaagaa gaaarttgca                                     150

<210> SEQ ID NO 21
<211> LENGTH: 150
<212> TYPE: DNA
<213> ORGANISM: Cucumis sativus
<220> FEATURE:
<221> NAME/KEY: SNP21
<222> LOCATION: (75)..(75)

<400> SEQUENCE: 21
tccwattctt caccttccac atatttgttg aaactaggaa actaaatcta ataaaataac    60
ctcccttaac acttaaggga tcctaacaat attctgttcc tctcactctc tctgatgcag    120
agtaaacttg taatttggct gtttgtacag                                     150

<210> SEQ ID NO 22
<211> LENGTH: 150
<212> TYPE: DNA
<213> ORGANISM: Cucumis sativus
<220> FEATURE:
<221> NAME/KEY: SNP22
<222> LOCATION: (75)..(75)

<400> SEQUENCE: 22
ctctaagtct gcaatgtgca agatagatca ctgcttgaaa cttgctgata catgaaatgt    60
caaaatttct tatgtagtac aatctgaatt gtaacatagg tgtaaataga atctcttcat    120
ttgggattta gaaagaaata attagaagaa                                     150

<210> SEQ ID NO 23
<211> LENGTH: 150
<212> TYPE: DNA
<213> ORGANISM: Cucumis sativus
<220> FEATURE:
<221> NAME/KEY: SNP23
<222> LOCATION: (75)..(75)

<400> SEQUENCE: 23
ccaacaatca attgacaggt acaatctctg aaacacattt ttcaaaccta agcaagctga    60
gaatcttaca cctaccttca aattctttga gattaaatgt cagtgcaaat tgggttcctc    120
catttcaagt cagaaacctt gacatgggtt                                     150

<210> SEQ ID NO 24
<211> LENGTH: 150
<212> TYPE: DNA
<213> ORGANISM: Cucumis sativus
<220> FEATURE:
<221> NAME/KEY: SNP24
<222> LOCATION: (75)..(75)

<400> SEQUENCE: 24
agaactagga catcctcgtg ttacctttag aataaatcac attttcaagg gccaataaac    60
tacaattagc tatcgatttt ggaattcaag taacaaaaac cgatcaaaag ctctataact    120
ggtttcatat gatgctatga mttaattttg                                     150
```

```
<210> SEQ ID NO 25
<211> LENGTH: 150
<212> TYPE: DNA
<213> ORGANISM: Cucumis sativus
<220> FEATURE:
<221> NAME/KEY: SNP25
<222> LOCATION: (75)..(75)

<400> SEQUENCE: 25
gatgatakac taaaaacatg ctacacaaaa cagtatttat ttgaaataaa atgcttttga      60
tagattgcaa gtgagtattg ttgaagcaaa tgttttcttc cagagagcaa ttgaaataat     120
tgatttgaaa acaattttga gaggatgttg                                      150

<210> SEQ ID NO 26
<211> LENGTH: 413
<212> TYPE: DNA
<213> ORGANISM: Cucumis sativus
<220> FEATURE:
<221> NAME/KEY: SNP26
<222> LOCATION: (251)..(251)

<400> SEQUENCE: 26
ctcgggtatt tggcatttag aatcgtcttc tgcccgtatt tcctccacgc gtgcccatcg      60
tccactaggt cgcagctttc tcttgcccaa ctctggcaac tcttcctgca aatttcaatt    120
ataaatattt ttattctaaa tacaattctc ccaaattctc tattattcat cttatgatca    180
actatatatt aaacttagtt taaattaata gaaaacctag ctaccttctc ttatagcaac    240
ccctgcgatc gttattaggg gtggagctct tgcaactgtc tccagattcc tcggattttc    300
tactaccatg atcctcgggt gagtccacaa tagagccatt tatgtcatcg gagtcgcagc    360
gatgattcaa gatggaaagt gttttggaga agaggatag gattctggtg agt           413

<210> SEQ ID NO 27
<211> LENGTH: 150
<212> TYPE: DNA
<213> ORGANISM: Cucumis sativus
<220> FEATURE:
<221> NAME/KEY: SNP27
<222> LOCATION: (75)..(75)

<400> SEQUENCE: 27
aaattgggag atgaatttgg ataaaagaga aaaacagaac aaggaagaaa aagaaatatg      60
tcataaaaat tggcataaat gtaaaagatg tacaaatgta tccaattgga agagtaagag    120
aggaaacaga ggaattagca ataacattgc                                      150
```

US 10,645,890 B2

INTROGRESSION OF A YIELD QTL IN *CUCUMIS SATIVUS* PLANTS

CROSS REFERENCE TO RELATED APPLICATIONS

This application is a 35 U.S.C. 371 National Phase of PCT Application No. PCT/EP2016/059829 filed May 3, 2016, which claims benefit to EP Application No. 15166819.1 filed May 7, 2015, the disclosure of which is hereby incorporated by reference in its entirety.

FIELD

The present invention relates to the field of cucumber breeding. Provided is a Quantitative Trait Locus (QTL) located on chromosome 3 of the cucumber genome, which can be used to increase yield in cultivated cucumbers (*Cucumis sativus* var. *sativus*), such as pickling cucumbers (e.g. American pickling, European pickling types), slicing cucumbers (e.g. American slicing), long cucumbers, short cucumbers, European greenhouse cucumbers, Beit-Alpha type cucumbers, oriental trellis type cucumbers (also marketed as 'burpless'), Asian cucumbers (which can be further subdivided into different types, such as Indian Mottled cucumber, Chinese Long cucumber, Korean cucumber and Japanese cucumber types, whereby the first belongs to the Indian cucumber group and the last three are part of the East Asian cucumber group).

The QTL is referred herein as QTL3.1. Also provided are cultivated cucumber plants comprising (an) introgression fragment on chromosomes 3 comprising QTL3.1, whereby the introgression fragment significantly increase the fruit yield of the cultivated cucumber comprising the introgression compared to the same cultivated cucumber lacking the introgression. The introgression fragment, comprising QTL3.1, is from a wild relative of cucumber. One plant of the wild relative of cucumber accession was used to make a double haploid population, which was then used to map and to introgress the QTL into the European long cucumber type. From this type the QTL can easily be transferred into any other cultivated cucumber type, such as short cucumber types, or into other long cucumber breeding lines or varieties. Seeds comprising the introgression fragment were deposited under accession number NCIMB42346.

In one aspect a cultivated cucumber plant comprising an introgression fragment on chromosomes 3 is provided, comprising QTL3.1, whereby the introgression fragment significantly increase the fruit yield of the cultivated cucumber comprising the introgression compared to the same cultivated cucumber lacking the introgression. Also one or more molecular markers (especially Single Nucleotide Polymorphisms or SNPs) which are present on the introgression fragment and which are indicative of the presence of the introgression fragment and methods of using such markers are provided herein. Likewise seeds, plant parts, cells and/or tissues comprising QTL3.1 in their genome and comprising otherwise a genome of cultivated cucumber in their genome are provided. It is noted that the term "genome of cultivated cucumber" does not exclude that there are other introgression fragments in the entire genome, e.g. on other chromosomes and/or for other traits.

Likewise seeds, plant parts, cells and/or tissues comprising QTL3.1 on chromosome 3 and comprising otherwise a chromosome 3 of cultivated cucumber in their genome are provided. In one aspect the plants, seeds, plant parts, cells and/or tissues comprise the introgression fragment from a wild relative of cucumber, whereby the introgression fragment comprising QTL3.1, which QTL is located physically in the region starting at 21.5 Mb and ending at 27.23 Mb of chromosome 3. Thus in one aspect all or part of the region starting at 21.5 Mb and ending at 27.23 Mb of chromosome 3 is from a wild relative of cucumber and comprises a positive yield QTL (QTL3.1 or a variant thereof). In one aspect the other regions of chromosome 3, i.e. from 0 Mb to 21.5 Mb and/or from 27.23 Mb to the end of chromosome 3 comprise or consist of cultivated cucumber chromosome regions.

In one aspect a cultivated *Cucumis sativus* var. *sativus* plant comprising an introgression fragment from a wild relative of cucumber on chromosome 3 in homozygous or heterozygous form is provided, wherein said introgression fragment comprises a Quantitative Trait Locus (QTL) located between the Single Nucleotide Polymorphism marker SNP_01 at nucleotide 75 of SEQ ID NO: 1 (or of a variant of SEQ ID NO: 1) and the Single Nucleotide Polymorphism marker SNP_27 at nucleotide 75 of SEQ ID NO: 27 (or of a variant of SEQ ID NO: 1), which QTL confers an increase in cucumber fruit yield. In one aspect the QTL is located between base 21,507,892 (SNP_01) and base 27,233,985 (SNP_27) of chromosome 3.

In one aspect QTL3.1 (i.e. the introgression fragment comprising the QTL) is present in heterozygous form in a cultivated cucumber plant, cell or tissue, especially in long cucumber. In another aspect QTL3.1 (i.e. the introgression fragment comprising the QTL) is present in homozygous form in a cultivated cucumber plant, cell or tissue, especially in long cucumber. In a specific aspect the cultivated cucumber plant is an F1 hybrid, especially an F1 hybrid generated by crossing two inbred parent lines, whereby at least one of the parent lines comprises the QTL3.1 (i.e. the introgression fragment comprising the QTL) in homozygous form. In a specific aspect the cultivated cucumber plant does not comprise any other introgression fragments on chromosome 3 of the cucumber genome which affect yield. In another aspect, there may be other introgression fragments on chromosome 3, e.g. in different regions of the chromosome.

BACKGROUND

Cultivated cucumber (*Cucumis sativus* var. *sativus* L.) is an important vegetable crop worldwide. It belongs to the family Cucurbitaceae. It is thought to originate from South East Asia from wild ancestors with small, bitter fruits, such as *Cucumis sativus* var. *hardwickii*.

The cultivated cucumber genome has seven pairs of chromosomes (n=7) and a haploid genome size of about 367 Mb (Megabases) with an estimated total of about 26,682 genes. The cucumber genome was the first vegetable genome to be sequenced (Huang et al. 2009, Nature Genetics, Volume 41, Number 12, p 1275-1283 and http://www.icugi.org/cgi-bin/gb2/gbrowse/cucumber_v2/).

Yield of cultivated cucumber has not increased much over the last decades. Shetty and Wehner 2002 (CropSci. 42: 2174-2183) screened the USDA cucumber germplasm collection for fruit quality and fruit yield under field conditions in North Carolina (USA) and suggest that high yielding cultigens identified in their study can be used to develop high yielding cultivars.

WO2009/082222 used on of the accessions identified by Shetty and Wehner in 2002 (supra), the Turkish Beit-Alpha landrace PI 169383 to identify QTLs for fruit weight of harvest stage cucumbers on linkage group 3 and/or 4 of PI 69383 and seeds were deposited of this accession under accession number NCIMB41532. This donor is a Turkish Beit Alpha landrace of cucumber (which is not a wild relative of cucumber) and does not contain the SNP markers of the instant invention. Further, the patent application describes cucumber plants comprising a whole chromosome 3 substitution, i.e. the whole chromosome 3 is from the donor PI169383.

Wei et al. 2014 (BMC Genomics 15: 1158, p 1-10) disclose mapping of immature and mature fruit length and immature fruit weight in a population derived from a cross between a Chinese cucumber inbred line (CC3) and NC76. NC76 was developed from a landrace of *Cucumis sativus* var. *sativus* from Afghanistan (P1246930) (which is not a wild relative of cucumber) and has short fruits (7~10 cm). By crossing the short fruited NC76 with the long fruited CC3, they mapped QTLs in a segregating F2 population for (immature and mature) fruit length and immature fruit weight, as presented in additional file 6. They found two QTLs for immature fruit length (fl3.1 and fl3.2), two QTLs for immature fruit weight (fw3.1 and fw3.2) and one QTL for mature fruit length (mfl3.1) on Linkage Group 3 (LG3), in addition to another QTL for immature fruit length on LG 1 (fl1.1) and LG6 (fl6.1), but they do not disclose any information on total fruit yield.

Fazio et al. 2003 (Theor Appl Genet 107: 864-874) genetically mapped a number of traits, including cumulative fruits per plants over three harvests and morphological traits such as little leaf (ll'). Their linkage group 6 appears to correspond to the physical chromosome 3. They mapped one QTL called fp16.1 which had a positive effect on cumulative fruit number per plant over three harvests (fruit number per plant was measured at three harvest points) to marker OP-AG1-2 at position 40.8 cM. It was only detected at one location. They also mapped another QTL called nfp6.2 which had a positive effect on number of fruits per plant to marker AK5-SCAR at position 38.6 cM. This QTL was detected at one location and was detected in all three harvests at that location. These QTLs are physically located on the lower half of chromosome 3 (around 3.0 Mb), while the QTL of the present invention is located on the upper half of chromosome 3, between 21.50 Mb and 27.23 Mb of chromosome 3.

Still, there remains a need for identifying QTLs for fruit yield in cucumber to be able to increase fruit yield of modern cucumber varieties.

General Definitions

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested cucumber fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Thus, for example reference may herein be made to a "yield allele" of the yield locus QTL3.1.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a QTL, a gene or genetic marker is found. The yield locus (or yield-increasing locus) is, thus, the location in the genome of cucumber, where QTL3.1 is found. In cultivated cucumber the QTLs are found on chromosome 3 (using the chromosome assignment of Huang et al. 2009, Nature Genetics, Volume 41, Number 12, p 1275-1283 and http://www.icugi.org/cgi-bin/gb2/gbrowse/cucumber_v2/) i.e. they are introgressed into the cultivated cucumber genome (i.e. onto chromosome 3) from a wild relative of cucumber.

A "quantitative trait locus", or "QTL" is a chromosomal locus that encodes for one or more alleles that affect the expressivity of a continuously distributed (quantitative) phenotype. The yield conferring quantitative trait locus (or "yield QTL") is named QTL3.1 herein.

"Cucumber genome" and "physical position on the cucumber genome" and "chromosome 3" refers to the physical genome of cultivated cucumber, world wide web at icugi.org/cgi-bin/gb2/gbrowse/cucumber_v2/, and the physical chromosomes and the physical position on the chromosomes. So, for example SNP_01 is located at the nucleotide (or 'base') positioned physically at nucleotide 21,507,892 of chromosome 3, which has a physical size from 0 to 39.47 Mb (i.e. 39,474,669 bases).

"Physical distance" between loci (e.g. between molecular markers and/or between phenotypic markers) on the same chromosome is the actually physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In cucumber, wild or primitive cucumber accessions (e.g. landraces) or wild relatives of cultivated cucumber can be used to introgress fragments of the wild genome into the genome of cultivated cucumber, *Cucumis sativus* var. *sativus* L. Such a cultivated cucumber plant thus has a "genome of cultivated *Cucumis sativus* var. *sativus*", but comprises in the genome a fragment of a wild or primitive cucumber or of a wild relative of cucumber, e.g. an introgression fragment of a related wild *Cucumis sativus* genome, such as *Cucumis sativus* var. *hardwickii, C. sativus* var. *sikkimensis Cucumis sativus* var. *xishuangbannesis*, or another wild cucumber or wild relative of cucumber. So, for example, a cultivated cucumber is provided herein comprising a genome of cultivated cucumber, and in that genome one introgression fragment on chromosome 3 of cultivated cucumber which confer enhanced yield compared to the cultivated cucumber genome lacking the introgression fragment (and having a chromosomes 3 of cultivated cucumber, without the introgression fragment). It is understood that the term "introgression fragment" never includes a whole chromosome, but only a part of a chromosome. The introgression fragment can be large, e.g. even three quarter or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"Cultivated cucumber" or "domesticated cucumber" refers to plants of *Cucumis sativus* var. *sativus* i.e. varieties, breeding lines or cultivars, cultivated by humans and having good agronomic characteristics, especially producing edible and marketable fruits of good size and quality and uniformity; such plants are not "wild cucumber" or "primitive cucumber" plants, i.e. plants which generally have much poorer yields and poorer agronomic characteristics than cultivated plants and are less uniform genetically and in their physiological and/or morphological characteristics. "Wild plants" of "wild cucumber" include for example ecotypes, landraces or wild accessions or wild relatives of a species. Cultivated cucumber plants (lines or varieties) can also be distinguished from wild or primitive cucumber accessions by the significantly lower amount of SNPs (less than 2,000,000 SNPs) and INDELs (insertions/deletions of shorter than 5 bp; less than 150,000 INDELs) in the genome and their significantly lower nucleotide diversity (equal to or less than $2.3\times10^{-3}\pi$) as described in Table 1 of Qi et al, Nature Genetics December 2013, Vol 45, No. 12, pages 1510-1518. SNP numbers, INDEL numbers and nucleotide diversity can be determined as described herein, especially in the section 'Online Methods'.

"Indian cucumber group" refers to wild or wild relatives of cucumbers from India, having a high amount of SNPs (more than 3,000,000 SNPs) and INDELs (insertions/deletions of shorter than 5 bp; more than 200,000 INDELs) in the genome and high nucleotide diversity (more than $3.0\times10^{-3}\pi$ or even more than $4.0\times10^{-3}\pi$).

"Eurasian cucumber group" refers to cultivated cucumbers from central or western Asia, Europe and the United States, having a low amount of SNPs (less than 2,000,000 SNPs, or less than 1,500,000 SNPs) and INDELs (insertions/deletions of shorter than 5 bp; less than 150,000 INDELs) in the genome and a low nucleotide diversity (equal to or less than $2.3\times10^{-3}\pi$, preferably less than $2.0\times10^{-3}\pi$).

"East Asian cucumber group" refers to cultivated cucumbers from East Asia, such as China, Korea and Japan, having a low amount of SNPs (less than 2,000,000 SNPs, or less than 1,500,000 SNPs) and INDELs (insertions/deletions of shorter than 5 bp; less than 150,000 INDELs, preferably less than 100,000) in the genome and a low nucleotide diversity (equal to or less than $2.3\times10^{-3}\pi$, preferably less than $2.0\times10^{-3}\pi$ or even less than $1.5\times10^{-3}\pi$).

"Xishuangbanna cucumber group" refers to cucumbers from the Xishuangbanna region of China, having a low amount of SNPs (less than 2,000,000 SNPs, or less than 1,500,000 SNPs or even less than 100,000 SNPs) and INDELs (insertions/deletions of shorter than 5 bp; less than 150,000 INDELs, preferably less than 100,000) in the genome and a low nucleotide diversity (equal to or less than $2.3\times10^{-3}\pi$, preferably less than $2.0\times10^{-3}\pi$ or even less than $1.5\times10^{-3}\pi$).

"Wild cucumber" or "primitive cucumber" refers to *C. sativus* var. *sativus* which generally have much poorer yields and poorer agronomic characteristics than cultivated plants and are less uniform genetically and in their physiological and/or morphological characteristics. Wild plants include for example ecotypes, landraces or wild accessions or wild relatives of a species.

"Wild relatives of cucumber" refer to *Cucumis sativus* var. *hardwickii, C. sativus* var. *sikkimensis, Cucumis sativus* var. *xishuangbannesis*.

"Landrace(s)" refers to primitive cultivars of *Cucumis sativus* var. *sativus* developed in local geographic regions, which often show a high degree of genetic variation in their genome and exhibit a high degree of morphological and/or physiological variation within the landrace (e.g. large variation in fruit size, etc.), i.e. are significantly less uniform than cultivated cucumber. Landraces are, therefore, herein included in the group "wild cucumber", which is distinct from "cultivated cucumber".

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

The term "yield-allele" refers to an allele found at the yield locus QTL3.1 introgressed into cultivated cucumber (onto cultivated *C. sativus* var. *sativus* chromosome 3) from a wild relative of cucumber. The term "yield-allele", thus, also encompasses yield-alleles obtainable from other *Cucumis* accessions. When one or two yield-alleles are present at the locus in the genome (i.e. in heterozygous or homozygous form), the plant line or variety produces a significantly higher fruit yield than the genetic control lacking the QTL. In cultivated cucumber plant lacking the introgression fragment, the *C. sativus* var. *sativus* allele found at the same locus on chromosome 3 is herein referred to as "wild type" allele (wt). As the yield QTLs are dominant, wt/wt plants show a normal yield, whereas QTL3.1/wt plants and QTL3.1/QTL3.1 plants are plants which possess the enhanced yield phenotype conferred by the yield-allele(s). The genotype of the SNP markers provided herein is also indicative of the wild type or of either of the QTLs in homozygous or heterozygous form. E.g. the genotype of SNP_01 indicative of QTL3.1 is 'TC' (QTL3.1/wt) or 'TT' (QTL3.1/QTL3.1) while the genotype indicative of the wild type, i.e. of the cultivated cucumber, is 'CC' (wt/wt).

A genetic element, an introgression fragment, or a gene or allele conferring a trait (such as yield) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

A "Variant" or "orthologous" sequence or a "variant QTL3.1" refers to a yield QTL (QTL3.1), or an introgression fragment comprising the QTL, which is derived from different wild relative of cucumber plant than the QTL3.1 present in NCIMB42346, but which variant comprises one or more of the SNPs linked to QTL3.1 and wherein the variant genomic sequence comprises substantial sequence identity to the SEQ ID NO: comprising the SNP (any one of SEQ ID NO: 1-27), i.e. at least 85%, 90%, 95%, 98%, 99% sequence identity or more. Thus, when reference herein is made to a certain SNP genotype in a specific genomic sequence (selected from SEQ ID NO: 1 to SEQ ID NO: 27), this encompasses also the SNP genotype in variants of the genomic sequence, i.e. the SNP genotype in a genomic sequence comprising at least 85%, 90%, 95%, 98%, 99% sequence identity or more to the sequence referred to (selected from SEQ ID NO: 1 to SEQ ID NO: 27). Thus any reference herein to any one of SEQ ID NO: 1 to 27 in one aspect also encompasses a variant of any one of SEQ ID NO: 1 to 27, said variant comprising at least 85%, 90%, 95%, 98%, 99% sequence identity or more to said sequence.

"Yield" or "fruit yield" or "average yield" refers to the average number of fruits per plant (FrPP) and/or the average fruit weight (grams) per plant (GrPP). This is determined for each plant line, hybrid or variety grown under the same conditions (e.g. the line, hybrid or variety with the QTL and the genetic control without QTL) and the average FrPP and/or GrPP of each line, hybrid or variety is calculated. Depending on the type of cucumber, the fruit yield is measured in different ways. So, for example, types which produce fruits continuously over a certain period of time, such as fresh market types (e.g. long cucumber types such as the European greenhouse cucumber, mini- or midi-types), fruits are harvested when they reach marketable size and harvesting is done over a specified period referred to as 'harvest period' (e.g. the harvest period starts when the first fruits reach marketable size and may be at least 10, 11, 12 or more weeks long). So for example the average FrPP and/or GrPP per line is measured per day and is cumulated for all days at the end of the harvest period to calculate the cumulative FrPP and/or GrPP for each line or variety (see also the Examples). "Marketable size" refers to fruits that are long enough and heavy enough to be marketed. Thus, fruits of marketable size are harvested at a time point which is optimal or near optimal for marketing and sale of the fruit. For long cucumber types, such as the European greenhouse cucumber, marketable size is reached when a fruit is at least about 26 or 27 cm long and has a minimum weight of 250 grams. For cucumbers types which are harvested at a single time point only, such as pickling cucumbers, "yield" or "fruit yield" or "average yield" refers to the average number of fruits of equal to or above 1.5 cm diameter per plant (FrPP) and/or the average fruit weight (grams) of fruits which are equal to or above 1.5 cm diameter per plant (GrPP) at a single harvest time-point. The single harvest time-point is in line with growers practice and chosen to maximize the number of fruits having a diameter between 1.5 cm and 5.0 cm. Depending on the desired fruit size, the time-point is generally reached when about 5%, about 10%, about 15% or about 20% of the fruits are oversized, (i.e. have a fruit diameter of 5.0 cm or more). Harvest is either by hand or by machine harvest. Thus, in one aspect all fruits per plant are harvested and only the ones with a diameter of at least 1.5 cm are counted and/or weighed (i.e. all fruits with a diameter of at least 1.5 cm are counted and/or weighed, including oversized fruits).

An "increased fruit yield" or a "significantly increased fruit yield" refers to a cultivated cucumber plant line, hybrid or variety comprising an introgression fragment on chromosome 3, comprising QTL3.1, having (due to the QTL) a statistically significantly higher average number of fruits per plant (FrPP) and/or a significantly higher average fruit weight per plant (GrPP) compared to the genetic control plant lacking the introgression fragments on chromosome 3 when grown in yield experiments under the same environmental conditions. Preferably trials are carried out in several replicates (2, 3, or preferably 3, 4, 5, 6, 7, 8, or more) with sufficient plants (e.g. at least 8, 9, 10, 15, 20, 30, 40, or more plants per line) comprising the introgression fragment on chromosome 3 and lacking the introgression fragment on chromosome 3 (i.e. genetic controls).

"Genetic control" is a cucumber line, variety or hybrid which has the same or very similar cultivated genome as the cucumber plant comprising the introgression on chromosome 3 except that it lacks the introgressions on chromosome 3, i.e. chromosome 3 is "wild type", i.e. cultivated cucumber genome. For example, seeds deposited under accession number NCIMB42346 are seeds of an F1 test-hybrid made between an introgression line (of the long cucumber type) comprising QTL3.1 on chromosome 3 and an elite cucumber breeding line (of the long cucumber type), while the genetic control, deposited under NCIMB 42345, are seeds of the recurrent parent of the introgression line (lacking QTL3.1) and the same elite cucumber breeding line.

The term "marker assay" refers to a molecular marker assay which can be used to test whether on cultivated C. sativus var. sativus chromosome 3 an introgression from a wild relative of cucumber is present which introgression fragment comprises the yield QTL (QTL3.1) (or whether a wild relative of cucumber comprises the QTL3.1 in its genome), by determining the genotype of any one or more markers linked to the QTL3.1, e.g. the genotype of one or more SNP markers selected from SNP_01 to SNP_27, and/or any wild relative of cucumber genome-specific marker in-between SNP markers SNP_01 and SNP_27, and/or within 7 cM or within 5 cM, 3 cM, 2 cM, 1 cM of any one of these markers, and/or within 5 Mb, 3 Mb, 2 Mb, 1 Mb, 0.5 Mb, 0.1 Mb, 50 kb, 20 kb, 10 kb, 5 kb, 2 kb, 1 kb or less of any one of these markers. A marker "in between" two markers is physically located in between the markers on the chromosome.

The SNP markers provided herein, i.e. SNP_01 to SNP_27, are located in the given order on the introgression fragment. "Consecutive" markers refers to markers in the same consecutive order, so e.g. two consecutive markers may be SNP_01 and SNP_02; SNP_02 and SNP_03; SNP_03 and SNP_04, etc. and three consecutive markers may be SNP_01 and SNP_02 and SNP_03; SNP_02 and SNP_03 and SNP_04; etc.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 8, 9, 10, 15, 20, 30, 40, 50 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control (e.g. herein the genetic control) show a statistically significant difference in that characteristic (e.g. the p-value is less than 0.05, p<0.05, using ANOVA) from the (mean of the) control.

A "recombinant chromosome" refers to a chromosome having a new genetic makeup arising through crossing-over between homologous chromosomes, e.g. a "recombinant chromosome 3", i.e. a chromosome 3 which is not present in either of the parent plants and arose through a rare double crossing-over event between homologous chromosomes of a chromosome 3 pair. Herein, for example, recombinant cucumber chromosome 3 is provided comprising an introgression from a wild relative of cucumber.

The term "traditional breeding techniques" encompasses herein crossing, backcrossing, selfing, selection, double haploid production, embryo rescue, protoplast fusion, marker assisted selection, mutation breeding etc., all as known to the breeder (i.e. methods other than genetic modification/transformation/transgenic methods), by which, for example, a recombinant chromosome 3 can be obtained, identified and/or transferred.

"Backcrossing" refers to a breeding method by which a (single) trait, such as a yield QTL, can be transferred from an inferior genetic background (e.g. a wild cucumber or wild relative of cucumber; also referred to as "donor") into a superior genetic background (also referred to as "recurrent parent"), e.g. cultivated cucumber. An offspring of a cross (e.g. an F1 plant obtained by crossing a wild cucumber or wild relative of cucumber with a cultivated cucumber; or an F2 plant or F3 plant, etc., obtained from selfing the F1) is "backcrossed" to the parent with the superior genetic background, e.g. to the cultivated parent. After repeated backcrossing, the trait of the inferior genetic background will have been incorporated into the superior genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to a yield QTL, can be used to detect and/or select cucumber plants comprising the yield QTL on chromosome 3. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g. within 7 cM or 5 cM, 4 cM, 3 cM, 2 cM, 1 cM or less) the less likely it is that the two markers will be separated from one another (and the more likely they will co-segregate as a unit).

A marker "within 7 cM or within 5 cM, 3 cM, 2 cM, or 1 cM" of another marker refers to a marker which genetically maps to within the 7 cM or 5 cM, 3 cM, 2 cM, or 1 cM region flanking the marker (i.e. either side of the marker). Similarly, a marker within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb, 2 kb, 1 kb or less of another marker refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb, 2 kb, 1 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation. In one aspect propagation by grafting, e.g. a scion onto a rootstock, is included herein.

"Cell culture" or "tissue culture" refers to the in vitro culture of cells or tissues of a plant.

"Regeneration" refers to the development of a plant from cell culture or tissue culture or vegetative propagation.

"Non-propagating cell" refers to a cell which cannot be regenerated into a whole plant.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Fine-mapping" refers to methods by which the position of a QTL can be determined more accurately (narrowed down) and by which the size of the introgression fragment comprising the QTL is reduced. For example Near Isogenic Lines for the QTL (QTL-NILs) can be made, which contain different, overlapping fragments of the introgression fragment within an otherwise uniform genetic background of the recurrent parent. Such lines can then be used to map on which fragment the QTL is located and to identify a line having a shorter introgression fragment comprising the QTL.

DETAILED DESCRIPTION

The present invention relates to a cultivated *Cucumis sativus* var. *sativus* plant comprising a yield QTL on chromosome 3 introgressed from wild relative of cucumber. Thus, the increased yield is conferred by an introgression fragment on cultivated cucumber chromosome 3 (comprising QTL3.1 or a variant thereof), wherein said introgression fragment is from a wild relative of cucumber.

When reference is made herein to an introgression fragment on chromosome 3 having a yield QTL this encompasses various sizes of introgression fragments, e.g. the fragment as found in NCIMB42346 comprising all SNP markers (SNP_01 to SNP_27, or any marker in between these, for the fragment on chromosome 3), but also smaller introgression fragments (comprising less than the 27 SNP markers such as only e.g. 1, 2, 3, 4, 5, 6, 7, 8, 9, 10, 11, 12, 13, 14, 15, 16, 17, 18, 19, 20, 21, 22, 23, 24, 25 or 26 of the SNP markers), where however the fragment remains large enough to confer significantly enhanced yield (compared to the genetic control) when the introgression fragment is in heterozygous or homozygous form in the cultivated cucumber genome. In other words, the fragment retains QTL3.1 or a variant thereof, i.e. it still confers significantly enhanced yield (compared to the control, e.g. the genetic control) when the introgression fragment is in heterozygous or homozygous form in the cultivated cucumber genome.

Thus, in one aspect a cultivated cucumber plant is provided comprising an introgression fragment from a wild relative of cucumber, wherein the introgression fragment comprises QTL3.1, or a variant thereof, and wherein the introgression fragment comprises all or part of the region starting at nucleotide (or base) 21,507,892 of chromosome 3 and ending at nucleotide (or base) 27,233,985 of chromosome 3. In other words, all or part of the region starting at nucleotide 21,507,892 of chromosome 3 and ending at nucleotide 27,233,985 of chromosome 3 is, in one aspect, from a wild relative of cucumber and comprises QTL3.1 or a variant thereof. Which sub-region contains QTL3.1 can be identified by e.g. fine-mapping. So, for example if QTL3.1 is found to be in between SNP_01 and SNP_10, then the plant of the invention only needs to comprise the introgression region starting at nucleotide 21,507,892 of chromosome 3 (SNP_01) and ending at nucleotide 23,706,444 (SNP_10) of chromosome 3.

In one aspect QTL3.1 (or a variant thereof) is located in-between marker SNP_01 in SEQ ID NO: 1 (or in a variant sequence of SEQ ID NO: 1) and marker SNP_27 in SEQ ID NO: 27 (or in a variant sequence of SEQ ID NO: 27). In another aspect QTL3.1 (or a variant thereof) is located in-between marker SNP_01 in SEQ ID NO: 1 (or in a variant sequence of SEQ ID NO: 1) and marker SNP_10 in SEQ ID NO: 10 (or in a variant sequence of SEQ ID NO: 10). In a further aspect QTL3.1 (or a variant thereof) is located in-between marker SNP_10 in SEQ ID NO: 10 (or in a variant sequence of SEQ ID NO: 10) and marker SNP_20 in SEQ ID NO: 20 (or in a variant sequence of SEQ ID NO: 20). In a further aspect QTL3.1 (or a variant thereof) is located in-between marker SNP_20 in SEQ ID NO: 20 (or in a variant sequence of SEQ ID NO: 20) and marker SNP_27 in SEQ ID NO: 27 (or in a variant sequence of SEQ ID NO: 27). In still a further aspect QTL3.1 (or a variant thereof) is located in-between marker SNP_06 in SEQ ID NO: 06 (or in a variant sequence of SEQ ID NO: 06) and marker SNP_23 in SEQ ID NO: 23 (or in a variant sequence of SEQ ID NO: 23).

In another aspect the introgression fragment of the invention (comprising QTL3.1 or a variant thereof) is a fragment comprising a smaller fragment (part) of the region starting at nucleotide (or base) 21,507,892 of chromosome 3 and ending at nucleotide (or base) 27,233,985 of chromosome 3, e.g. having a size of e.g. 5.0 Mb, 4.0 Mb, 3.0 Mb, 2.5 Mb, 2 Mb, 1 Mb, 0.5 Mb, 100 kb, 50 kb, 35 kb, 30 kb, 20 kb, or less and comprising the QTL or a variant thereof. In one aspect the part is at least 5 kb, 10 kb, 20 kb in size, or more.

In one aspect the cultivated cucumber plant of the invention comprises an introgression fragment from a wild relative of cucumber, which introgression fragment comprises QTL3.1 or a variant thereof, wherein the introgression fragment comprises all of part of the region starting at 21.50 Mb and ending at 27.3 Mb of the physical chromosome 3.

In one aspect the introgression fragment on chromosome 3 comprising QTL3.1, or a variant thereof, is obtainable by crossing a plant grown from NCIMB42346 with another cucumber plant, especially a cultivated cucumber plant, in one aspect a long cucumber type.

In one aspect the cultivated cucumber plant of the invention comprising QTL3.1, or a variant thereof, is a plant wherein said introgression fragment on chromosome 3 is obtainable by crossing a plant grown from seeds deposited under accession number NCIMB42345 with another cucumber plant. Thus, in one aspect the QTL is the QTL present in seeds deposited under accession number NCIMB42345.

When referring to the SNP markers herein, which are indicative of the presence of the introgression fragment (and the yield QTL present on the introgression fragment), it is understood that the SNP genotype which is indicative of the introgression fragment is referred to, i.e. the SNP genotype as provided in Table 5 herein below. It is noted that the SNP marker genotype can distinguish between the introgression fragment being in homozygous or heterozygous form, as shown in the Table. In homozygous form the nucleotide is identical, while in heterozygous form the nucleotide is not identical. The SNP genotype of the 'wild type' chromosome lacking the introgression fragment is the other genotype, also listed in Table 5 (under genotype of recurrent parent). So, e.g. the genotype of SNP_01 indicative of the introgression fragment comprising QTL3.1 is 'TC' (QTL3.1/wt) or 'TT' (QTL3.1/QTL3.1) while the SNP genotype indicative of the wild type/genetic control (lacking the introgression fragment) is 'CC' (wt/wt). Thus, when referring to a plant or plant part (e.g. cell) comprising the introgression fragment in homozygous or heterozygous form, it is understood that the SNP markers linked to the introgression fragment have the corresponding SNP genotype.

So in one aspect, a cultivated *Cucumis sativus* var. *sativus* plant is provided comprising an introgression fragment on chromosome 3 in homozygous or heterozygous form, wherein said introgression fragment confers an increase in cucumber fruit yield compared to the cucumber plant lacking the introgression fragment on chromosome 3, e.g. the genetic control or control variety, when grown under the same conditions.

The increase in cucumber fruit yield is phenotypically expressed as a (statistically) significantly higher average number of fruits per plant (FrPP) of the cultivated cucumber plant line or variety comprising the introgression fragment on chromosome 3 in homozygous or heterozygous form compared to the genetic control line or variety lacking the introgression fragment on chromosome 3 when grown under the same environment and/or a significantly higher average fruit weight per plant (GrPP) of the plant line or variety comprising the introgression fragment compared to the genetic control line or variety lacking the introgression fragment when grown under the same environment.

Fruit yield (total average FrPP and/or GrPP) is preferably in the cucumber plant comprising QTL3.1 (or a variant) at least 3%, 4%, 5%, 6%, 7%, 8%, 9%, 10%, 11%, 12%, 13%, 14%, 15% higher than in the control, preferably than in the genetic control, when grown under the same environment.

The plants of the invention therefore comprise a genome of cultivated cucumber, with at least one or two recombinant chromosomes, namely one or two recombinant chromosomes 3 (i.e. heterozygous or homozygous). The recombinant chromosomes comprise a fragment of a wild relative of cucumber, which is easily distinguishable from the cultivated cucumber genome by molecular marker analysis, whole genome sequencing, chromosome painting and similar techniques.

In one aspect the introgression fragment on chromosome 3 is from a wild relative of cucumber, comprises the positive yield QTL3.1, or a variant thereof, and comprises all or part of the region starting at nucleotide 21,507,892 of chromosome 3 and ending at nucleotide 27,233,985 of chromosome 3. Thus, the introgression fragment comprises the yield QTL3.1 or a variant thereof and one or more or all (e.g. 2, 3, 4, 5, 6, 7, 8, 9, 10, 11, 12, 13, 14, 15, 16, 17, 18, 19, 20, 21, 22, 23, 24, 25, 26, 27) SNP markers of the wild relative of cucumber selected from SNP_01 to SNP_27 as shown in Table 5.

It is understood that for markers that are smaller introgression fragments described herein, i.e. lacking 1, 2, 3, 4, 5, 6, 7, 8, 9, 10, 11, 12, 13, 14, 15 or more markers of the markers listed herein (e.g. SNP_01 to SNP_27) or subgroups of those markers, the SNP genotype for the wild-relative of cucumber is missing (i.e. the donor genotype is not detected), and instead the SNP genotype of cultivated cucumber is detected for the "missing" SNP marker.

In one aspect the presence of the introgression fragment on chromosomes 3 in the genome of the plant or plant cell or plant tissue (or in the DNA extracted therefrom) is detectable by a molecular marker assay which detects one or more molecular markers of the introgression fragment. However, as mentioned, other techniques may be used, e.g. the SNP genotype of the markers may also be determined by sequencing or by using alternative markers located in between the SNP markers provided herein or within 7 cM, or within 5 cM, of a marker provided herein; or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb, 2 kb, 1 kb or less of a marker provided herein.

When reference is made herein to one or more molecular markers being "detectable" by a molecular marker assay, this means of course that the plant or plant part comprises the one or more markers in its genome, as the marker would otherwise not be detectable.

Cucumber Plants Comprising an Introgression Fragment on Chromosome 3 (Yield QTL 3.1)

In one aspect a cultivated *Cucumis sativus* var. *sativus* plant comprising an introgression fragment from a wild relative of cucumber on chromosome 3 in homozygous or heterozygous form is provided, wherein said introgression fragment comprises a Quantitative Trait Locus (QTL) located between the Single Nucleotide Polymorphism marker SNP_01 at nucleotide 75 of SEQ ID NO: 1 (or of a variant of SEQ ID NO: 1) and the Single Nucleotide Polymorphism marker SNP_27 at nucleotide 75 of SEQ ID NO: 27 (or of a variant of SEQ ID NO: 1), which QTL confers an increase in cucumber fruit yield. In one aspect the QTL is located between base 21,507,892 (SNP_01) and base 27,233,985 (SNP_27) of chromosome 3.

Thus, in one aspect QTL3.1 is located in the region between SNP_01 in SEQ ID NO: 1 (or in a variant thereof) and SNP_27 in SEQ ID NO: 27 (or a variant thereof).

Therefore, in one aspect a cultivated *Cucumis sativus* var. *sativus* plant is provided comprising an introgression fragment on chromosome 3 in homozygous or heterozygous form, wherein said introgression fragment confers an increase in cucumber fruit yield (compared to the plant lacking the introgression fragment, e.g. the genetic control) and wherein said introgression fragment is detectable by a molecular marker assay (i.e. the plant comprises one or more molecular markers) which detects at least 1, preferably at least 2 or 3, or at least 4, 5, 6, 7, 8, 9, 10, 11, 12, 13, 14, 15, 16, 17, 18, 19, 20, 21, 22, 23, 24, 25, 26 or 27 of the markers selected from the group consisting of:

a) the TC or TT genotype for the Single Nucleotide Polymorphism marker SNP_01 in SEQ ID NO: 1 (or in a variant thereof);

b) the TC or TT genotype for the Single Nucleotide Polymorphism marker SNP_02 in SEQ ID NO: 2 (or in a variant thereof);

c) the TC or TT genotype for the Single Nucleotide Polymorphism marker SNP_03 in SEQ ID NO: 3 (or in a variant thereof);

d) the TC or TT genotype for the Single Nucleotide Polymorphism marker SNP_04 in SEQ ID NO: 4 (or in a variant thereof);

e) the GA or GG genotype for the Single Nucleotide Polymorphism marker SNP_05 in SEQ ID NO: 5 (or in a variant thereof);

f) the TC or TT genotype for the Single Nucleotide Polymorphism marker SNP_06 in SEQ ID NO: 6 (or in a variant thereof);

g) the TC or TT genotype for the Single Nucleotide Polymorphism marker SNP_07 in SEQ ID NO: 7 (or in a variant thereof);

h) the TC or TT genotype for the Single Nucleotide Polymorphism marker SNP_08 in SEQ ID NO: 8 (or in a variant thereof);

i) the CT or CC genotype for the Single Nucleotide Polymorphism marker SNP_09 in SEQ ID NO: 9 (or in a variant thereof);

l) the CT or CC genotype for the Single Nucleotide Polymorphism marker SNP_10 in SEQ ID NO: 10 (or in a variant thereof);

k) the TG or TT genotype for the Single Nucleotide Polymorphism marker SNP_11 in SEQ ID NO: 11 (or in a variant thereof);

l) the AG or AA genotype for the Single Nucleotide Polymorphism marker SNP_12 in SEQ ID NO: 12 (or in a variant thereof);

m) the TC or TT genotype for the Single Nucleotide Polymorphism marker SNP_13 in SEQ ID NO: 13 (or in a variant thereof);

n) the AG or AA genotype for the Single Nucleotide Polymorphism marker SNP_14 in SEQ ID NO: 14 (or in a variant thereof);

o) the CT or CC genotype for the Single Nucleotide Polymorphism marker SNP_15 in SEQ ID NO: 15 (or in a variant thereof);

p) the CT or CC genotype for the Single Nucleotide Polymorphism marker SNP_16 in SEQ ID NO: 16 (or in a variant thereof);

q) the GA or GG genotype for the Single Nucleotide Polymorphism marker SNP_17 in SEQ ID NO: 17 (or in a variant thereof);

r) the CT or CC genotype for the Single Nucleotide Polymorphism marker SNP_18 in SEQ ID NO: 18 (or in a variant thereof);

s) the GA or GG genotype for the Single Nucleotide Polymorphism marker SNP_19 in SEQ ID NO: 19 (or in a variant thereof);

t) the CT or CC genotype for the Single Nucleotide Polymorphism marker SNP_20 in SEQ ID NO: 20 (or in a variant thereof);
u) the AC or AA genotype for the Single Nucleotide Polymorphism marker SNP_21 in SEQ ID NO: 21 (or in a variant thereof);
v) the TC or TT genotype for the Single Nucleotide Polymorphism marker SNP_22 in SEQ ID NO: 22 (or in a variant thereof);
w) the CT or TT genotype for the Single Nucleotide Polymorphism marker SNP_23 in SEQ ID NO: 23 (or in a variant thereof);
x) the GA or GG genotype for the Single Nucleotide Polymorphism marker SNP_24 in SEQ ID NO: 24 (or in a variant thereof);
y) the GA or GG genotype for the Single Nucleotide Polymorphism marker SNP_25 in SEQ ID NO: 25 (or in a variant thereof);
z) the GA or GG genotype for the Single Nucleotide Polymorphism marker SNP_26 in SEQ ID NO: 26 (or in a variant thereof);
aa) the AG or AA genotype for the Single Nucleotide Polymorphism marker SNP_27 in SEQ ID NO: 27 (or in a variant thereof); and optionally
bb) any wild relative of cucumber genome-specific marker in between marker SNP_01 and SNP_27.

As mentioned previously, when referring to a SNP in a variant sequence, that variant sequence comprises at least 85% sequence identity with the mentioned sequence.

In one aspect said at least 1, preferably at least 2 or 3, or at least 4, 5, 6, 7, 8, 9, 10, 11, 12, 13, 14, 15, 16, 17, 18, 19, 20, 21, 22, 23, 24, 25, 26 or 27 markers are selected from the group consisting of markers a) to aa). In one aspect said at least 1, preferably at least 2 or 3, or at least 4, 5, 6, 7, 8, 9, 10, 11, 12, 13, 14, 15, 16, 17, 18, 19, 20, 21, 22, 23, 24, 25, 26 or 27 markers are consecutive markers.

As mentioned, the skilled person can also develop other molecular markers, e.g. a wild-relative of cucumber genome-specific marker in-between marker SNP_01 and SNP_27 and/or within 7 cM or within 5 cM of any one of SNP_01 to SNP_27, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_01 to SNP_27. Such markers may also be a stretch of nucleotide, CAPS markers, INDELs, etc. The skilled person can, for example, sequence the introgression fragment found in seeds deposited under accession number NCIMB42346 and use the sequence information to develop new markers and marker assays.

In another aspect QTL3.1 is located in the region between SNP_01 in SEQ ID NO: 1 (or in a variant thereof) and SNP_10 in SEQ ID NO: 10 (or a variant thereof).

Thus, another aspect a cultivated *Cucumis sativus* var. *sativus* plant is provided comprising an introgression fragment on chromosome 3 in homozygous or heterozygous form, wherein said introgression fragment confers an increase in cucumber fruit yield (compared to the plant lacking the introgression fragment, e.g. the genetic control) and wherein said introgression fragment is detectable by a molecular marker assay which detects at least 1, preferably at least 2 or 3, or at least 4, 5, 6, 7, 8, 9, 10 of the markers selected from the group consisting of:
a) the TC or TT genotype for the Single Nucleotide Polymorphism marker SNP_01 in SEQ ID NO: 1 (or in a variant thereof);
b) the TC or TT genotype for the Single Nucleotide Polymorphism marker SNP_02 in SEQ ID NO: 2 (or in a variant thereof);
c) the TC or TT genotype for the Single Nucleotide Polymorphism marker SNP_03 in SEQ ID NO: 3 (or in a variant thereof);
d) the TC or TT genotype for the Single Nucleotide Polymorphism marker SNP_04 in SEQ ID NO: 4 (or in a variant thereof);
e) the GA or GG genotype for the Single Nucleotide Polymorphism marker SNP_05 in SEQ ID NO: 5 (or in a variant thereof);
f) the TC or TT genotype for the Single Nucleotide Polymorphism marker SNP_06 in SEQ ID NO: 6 (or in a variant thereof);
g) the TC or TT genotype for the Single Nucleotide Polymorphism marker SNP_07 in SEQ ID NO: 7 (or in a variant thereof);
h) the TC or TT genotype for the Single Nucleotide Polymorphism marker SNP_08 in SEQ ID NO: 8 (or in a variant thereof);
i) the CT or CC genotype for the Single Nucleotide Polymorphism marker SNP_09 in SEQ ID NO: 9 (or in a variant thereof);
j) the CT or CC genotype for the Single Nucleotide Polymorphism marker SNP_10 in SEQ ID NO: 10 (or in a variant thereof); and optionally
k) any wild relative of cucumber genome-specific marker in between marker SNP_01 and SNP_10.

In one aspect said at least 1, preferably at least 2 or 3, or at least 4, 5, 6, 7, 8, 9, or 10 markers are selected from the group consisting of markers a) to j). In one aspect said at least 1, preferably at least 2 or 3, or at least 4, 5, 6, 7, 8, 9, or 10 markers are consecutive markers.

In a further aspect QTL3.1 is located in the region between SNP_10 in SEQ ID NO: 10 (or in a variant thereof) and SNP_20 in SEQ ID NO: 20 (or a variant thereof).

Therefore in a different aspect a cultivated *Cucumis sativus* var. *sativus* plant is provided comprising an introgression fragment on chromosome 3 in homozygous or heterozygous form, wherein said introgression fragment confers an increase in cucumber fruit yield (compared to the plant lacking the introgression fragment, e.g. the genetic control) and wherein said introgression fragment is detectable by a molecular marker assay which detects at least 1, preferably at least 2 or 3, or at least 4, 5, 6, 7, 8, 9, 10 or 11 of the markers selected from the group consisting of:
1) the CT or CC genotype for the Single Nucleotide Polymorphism marker SNP_10 in SEQ ID NO: 10 (or in a variant thereof);
2) the TG or TT genotype for the Single Nucleotide Polymorphism marker SNP_11 in SEQ ID NO: 11 (or in a variant thereof);
3) the AG or AA genotype for the Single Nucleotide Polymorphism marker SNP_12 in SEQ ID NO: 12 (or in a variant thereof);
4) the TC or TT genotype for the Single Nucleotide Polymorphism marker SNP_13 in SEQ ID NO: 13 (or in a variant thereof);
5) the AG or AA genotype for the Single Nucleotide Polymorphism marker SNP_14 in SEQ ID NO: 14 (or in a variant thereof);
6) the CT or CC genotype for the Single Nucleotide Polymorphism marker SNP_15 in SEQ ID NO: 15 (or in a variant thereof);

7) the CT or CC genotype for the Single Nucleotide Polymorphism marker SNP_16 in SEQ ID NO: 16 (or in a variant thereof);
8) the GA or GG genotype for the Single Nucleotide Polymorphism marker SNP_17 in SEQ ID NO: 17 (or in a variant thereof);
9) the CT or CC genotype for the Single Nucleotide Polymorphism marker SNP_18 in SEQ ID NO: 18 (or in a variant thereof);
10) the GA or GG genotype for the Single Nucleotide Polymorphism marker SNP_19 in SEQ ID NO: 19 (or in a variant thereof);
11) the CT or CC genotype for the Single Nucleotide Polymorphism marker SNP_20 in SEQ ID NO: 20 (or in a variant thereof); and optionally
12) any wild relative of cucumber genome-specific marker in between marker SNP_10 and SNP_20.

In one aspect said at least 1, preferably at least 2 or 3, or at least 4, 5, 6, 7, 8, 9, 10 or 11 markers are selected from the group consisting of markers 1) to 11). In one aspect said at least 1, preferably at least 2 or 3, or at least 4, 5, 6, 7, 8, 9, 10, or 11 markers are consecutive markers.

In another aspect QTL3.1 is located in the region between SNP_20 in SEQ ID NO: 20 (or in a variant thereof) and SNP_27 in SEQ ID NO: 27 (or a variant thereof).

Therefore in a further aspect a cultivated *Cucumis sativus* var. *sativus* plant is provided comprising an introgression fragment on chromosome 3 in homozygous or heterozygous form, wherein said introgression fragment confers an increase in cucumber fruit yield (compared to the plant lacking the introgression fragment, e.g. the genetic control) and wherein said introgression fragment is detectable by a molecular marker assay which detects at least 1, preferably at least 2 or 3, or at least 4, 5, 6, 7 or 8 of the markers selected from the group consisting of:
1) the CT or CC genotype for the Single Nucleotide Polymorphism marker SNP_20 in SEQ ID NO: 20 (or in a variant thereof);
2) the AC or AA genotype for the Single Nucleotide Polymorphism marker SNP_21 in SEQ ID NO: 21 (or in a variant thereof);
3) the TC or TT genotype for the Single Nucleotide Polymorphism marker SNP_22 in SEQ ID NO: 22 (or in a variant thereof);
4) the CT or TT genotype for the Single Nucleotide Polymorphism marker SNP_23 in SEQ ID NO: 23 (or in a variant thereof);
5) the GA or GG genotype for the Single Nucleotide Polymorphism marker SNP_24 in SEQ ID NO: 24 (or in a variant thereof);
6) the GA or GG genotype for the Single Nucleotide Polymorphism marker SNP_25 in SEQ ID NO: 25 (or in a variant thereof);
7) the GA or GG genotype for the Single Nucleotide Polymorphism marker SNP_26 in SEQ ID NO: 26 (or in a variant thereof);
8) the AG or AA genotype for the Single Nucleotide Polymorphism marker SNP_27 in SEQ ID NO: 27 (or in a variant thereof); and optionally
9) any wild relative of cucumber genome-specific marker in between marker SNP_20 and SNP_27.

In one aspect said at least 1, preferably at least 2 or 3, or at least 4, 5, 6, 7 or 8 markers are selected from the group consisting of markers 1) to 8). In one aspect said at least 1, preferably at least 2 or 3, or at least 4, 5, 6, 7 or 8 markers are consecutive markers.

In even another aspect QTL3.1 is located in the region between SNP_06 in SEQ ID NO: 06 (or in a variant thereof) and SNP_23 in SEQ ID NO: 23 (or a variant thereof).

Thus, a cultivated *Cucumis sativus* var. *sativus* plant is provided comprising an introgression fragment on chromosome 3 in homozygous or heterozygous form, wherein said introgression fragment confers an increase in cucumber fruit yield (compared to the plant lacking the introgression fragment, e.g. the genetic control) and wherein said introgression fragment is detectable by a molecular marker assay which detects at least 1, preferably at least 2 or 3, or at least 4, 5, 6, 7, 8, 9, 10, 11, 12, 13, 14, 15, 16, 17 or 18 of the markers selected from the group consisting of:
a) the TC or TT genotype for the Single Nucleotide Polymorphism marker SNP_06 in SEQ ID NO: 6 (or in a variant thereof);
b) the TC or TT genotype for the Single Nucleotide Polymorphism marker SNP_07 in SEQ ID NO: 7 (or in a variant thereof);
c) the TC or TT genotype for the Single Nucleotide Polymorphism marker SNP_08 in SEQ ID NO: 8 (or in a variant thereof);
d) the CT or CC genotype for the Single Nucleotide Polymorphism marker SNP_09 in SEQ ID NO: 9 (or in a variant thereof);
e) the CT or CC genotype for the Single Nucleotide Polymorphism marker SNP_10 in SEQ ID NO: 10 (or in a variant thereof);
f) the TG or TT genotype for the Single Nucleotide Polymorphism marker SNP_11 in SEQ ID NO: 11 (or in a variant thereof);
g) the AG or AA genotype for the Single Nucleotide Polymorphism marker SNP_12 in SEQ ID NO: 12 (or in a variant thereof);
h) the TC or TT genotype for the Single Nucleotide Polymorphism marker SNP_13 in SEQ ID NO: 13 (or in a variant thereof);
i) the AG or AA genotype for the Single Nucleotide Polymorphism marker SNP_14 in SEQ ID NO: 14 (or in a variant thereof);
the CT or CC genotype for the Single Nucleotide Polymorphism marker SNP_15 in SEQ ID NO: 15 (or in a variant thereof);
k) the CT or CC genotype for the Single Nucleotide Polymorphism marker SNP_16 in SEQ ID NO: 16 (or in a variant thereof);
l) the GA or GG genotype for the Single Nucleotide Polymorphism marker SNP_17 in SEQ ID NO: 17 (or in a variant thereof);
m) the CT or CC genotype for the Single Nucleotide Polymorphism marker SNP_18 in SEQ ID NO: 18 (or in a variant thereof);
n) the GA or GG genotype for the Single Nucleotide Polymorphism marker SNP_19 in SEQ ID NO: 19 (or in a variant thereof);
o) the CT or CC genotype for the Single Nucleotide Polymorphism marker SNP_20 in SEQ ID NO: 20 (or in a variant thereof);
p) the AC or AA genotype for the Single Nucleotide Polymorphism marker SNP_21 in SEQ ID NO: 21 (or in a variant thereof);
q) the TC or TT genotype for the Single Nucleotide Polymorphism marker SNP_22 in SEQ ID NO: 22 (or in a variant thereof);
r) the CT or TT genotype for the Single Nucleotide Polymorphism marker SNP_23 in SEQ ID NO: 23 (or in a variant thereof); and optionally s) any wild relative of cucumber genome-specific marker in between marker SNP_06 and SNP_23.

In one aspect said at least 1, preferably at least 2 or 3, or at least 4, 5, 6, 7, 8, 9, 10, 11, 12, 13, 14, 15, 16, 17 or 18 markers are selected from the group consisting of markers a) to r). In one aspect said at least 1, preferably at least 2 or 3, or at least 4, 5, 6, 7, 8, 9, 10, 11, 12, 13, 14, 15, 16, 17, or 18 markers are consecutive markers.

The fragment comprising the QTL may, thus, be large (comprising SNP_01 to SNP_27), or may be smaller and lack markers having the genotype of the wild relative of cucumber (i.e. the markers have the cultivated cucumber genotype instead, see also Table 5 Genotype of recurrent parent), but it may still confer enhanced yield on the cultivated cucumber plant, i.e. it can still comprise the yield allele (QTL3.1 or a variant). Such smaller introgression fragments are an embodiment of the invention. Plants having smaller introgression fragments which still confer the enhanced yield (i.e. contain the yield allele) can be generated using known techniques, such as fine-mapping or similar techniques. For example by starting with a plant comprising the introgression fragment as found in seeds deposited under accession number NCIMB 42346 and crossing such a plant with another cultivated cucumber plant and selfing the progeny of said cross, and/or backcrossing the progeny, to generate a population of plants which may contain recombinants having a smaller introgression fragment on chromosome 3, which fragments still confer enhanced yield in relation to a plant lacking the introgression fragment (such as the genetic control, e.g. plants grown from seeds deposited under NCIMB42345), e.g. a fragment comprising markers SNP_01 to SNP_10 (or smaller, e.g. comprising only 9, 8, 7, 6, 5, 4, 3, 2 or 1 of the SNP markers), SNP_10 to SNP_20 (or smaller e.g. comprising only 10, 9, 8, 7, 6, 5, 4, 3, 2 or 1 of the SNP markers), SNP_20 to SNP_27 (or smaller e.g. comprising only 7, 6, 5, 4, 3, 2 or 1 of the SNP markers) or SNP_06 to SNP_23 (or smaller e.g. comprising only 17, 16, 15, 14, 13, 12, 11, 10, 9, 8, 7, 6, 5, 4, 3, 2 or 1 of the SNP markers). Marker assays can be used to determine the size of the smaller introgression fragment. One or more of the SNP markers with the genotype of the wild relative of cucumber may be missing. The cultivated cucumber genotype is then detected for these SNP markers. The yield of plants comprising such a smaller introgression fragment can then be compared in yield experiments as described herein, i.e. growing a plurality of plants comprising the smaller introgression fragment in field experiments together with suitable control plants, lacking the introgression fragment. The control plants are preferably a genetic control, such as NCIMB42345. If the average yield remains significantly higher than in the control, then the smaller introgression fragment has retained the QTL3.1.

Alternatively, the same or variant QTL (QTL3.1 or variant QTL3.1) may be introgressed from a different wild relative of cucumber, whereby optionally not all SNP markers disclosed herein may be present. Such alternative wild relative of cucumber sources can be identified using the SNP markers provided herein, by screening germplasm (i.e. accessions of) wild relatives of cucumber using a marker assay to detect the genotype of markers SNP_01 to SNP_27, or of markers SNP_01 to SNP_10, SNP_10 to SNP_20, SNP_20 to SNP_27, or SNP_06 to SNP_23, or even only a smaller subgroup of these markers (e.g. 2, 3, 4, 5, 6, 7, 8, or more). Plants comprising the same or variant QTL3.1 from other sources are also an embodiment of the invention. As long as at least one or more (or all) of the SNPs of SNP_01 to SNP_27, or of the SNPs of SNP_01 to SNP_10, or of the SNPs of SNP_10 to SNP_20, or of the SNPs of SNP_20 to SNP_27, or of the SNPs of SNP_06 to SNP_23 is present, the plant has the yield-increasing genotype, i.e. the plant comprises QTL3.1 (or a variant thereof). The skilled person can then introgress the QTL3.1 (or a variant thereof) into cultivated cucumber in order to enhance fruit yield as described herein and in order to confirm that the QTL enhances yield when present in cultivated cucumber.

As described above, in one embodiment the cultivated cucumber plant of the invention comprises an introgression fragment comprising at least a subset of SNP markers with the genotype of the wild relative of cucumber, i.e. at least 1, 2, 3, 4, or 5 markers of SNP_01 to SNP_27, or of SNP_01 to SNP_10, or of SNP_10 to SNP_20, or of SNP_20 to SNP_27, or of SNP_06 to SNP_23. In one aspect the cultivated cucumber plant comprises all, or all except 1 or 2 markers of SNP_01 to SNP_27, or of SNP_01 to SNP_10, or of SNP_10 to SNP_20, or of SNP_20 to SNP_27, or of SNP_06 to SNP_23.

Thus, the introgression fragment (and a cultivated cucumber plant or plant part, e.g., a cell, comprising the introgression fragment) can be detected in a marker assay by detecting the SNP genotype of the introgression fragment (i.e. of the wild relative of cucumber germplasm) of one or more or all of the markers above.

Thus, in one aspect, a Quantitative Trait Locus (QTL3.1) was found to be present on chromosome 3 of a wild relative of cucumber which, when transferred (introgressed) into a cultivated cucumber variety or breeding line, and when present in heterozygous or homozygous form, confers significantly enhanced fruit yield onto the cultivated cucumber plant. The QTL, or the introgression fragment comprising the QTL (comprising the yield allele), is thus dominant, i.e. it is sufficient to have the introgression fragment on one of the chromosomes 3 (one recombinant chromosome 3), while the homologous chromosome 3 of the pair may be a (non-recombinant) chromosome 3 of cultivated *C. sativus* var. *sativus* lacking the introgression fragment.

Although the present source of the yield QTL is a single, specific wild source, there are likely other wild relatives of *Cucumis* accessions which comprise QTL3.1 at the same locus on chromosome 3. Such loci may comprise yield alleles which have slightly different nucleotide sequences, i.e. variants of the allele (QTL) found herein. Such variant QTLs can also be identified and introgressed into cultivated cucumber as described herein, to generate a cultivated cucumber plant comprising a genome of cultivated *C. sativus* var. *sativus* and a recombinant chromosome 3, whereby the recombinant chromosome 3 comprises a wild relative of *Cucumis sativus* species introgression fragment, which confers an enhanced yield phenotype onto the cultivated cucumber plant when present in homozygous or heterozygous form. To identify such wild relatives of cucumber comprising QTL3.1, wild accessions can be screened, e.g. in a marker assay or by sequence comparison or other methods, for the presence of one or more of the SNP markers provided herein. The putative yield QTLs (or variant QTLs) can then be introgressed into cultivated cucumber, e.g. using MAS, i.e. using one or more (or all) of the SNP markers provided herein to detect and/or select progeny plants (e.g. backcross plants) comprising a recombinant chromosome 3. The selected plants, i.e. the cultivated cucumber plants comprising an introgression fragment on chromosome 3, wherein the introgression fragment on chromosome 3 is detectable by one or more of the SNP markers SNP_01 to SNP_27, one or more of the SNP markers SNP_01 to SNP_10, one or more of the SNP markers SNP_10 to SNP_20, one or more of the SNP markers SNP_20 to SNP_27, or one or more of the SNP markers SNP_06 to SNP_23 (as described elsewhere herein) can then be phenotyped in yield experiments together with the suitable control plants, preferably at least the genetic control, in order to determine whether the introgression fragment indeed causes a significant yield increase.

Accessions of wild relatives of cucumber, are obtainable from the USDA National Plant Germplasm System collection or other seed collections, and can thus be screened for the presence of QTL3.1 using e.g. a marker assay as described herein, and accessions comprising one or more of the SNP markers (e.g. at least 1, 2, 3, 4, 5, 6, 7, 8, 9, 10, 11, 12, 13, 14, 15, 16, 17, 18, 19, 20, 21, 22, 23, 24, 25, 26 or all 27 SNP markers indicative of QTL3.1 can be crossed with a cultivated cucumber plant having normal wild-type, non-recombinant chromosomes 3. The F1 or F2 generation (or further generation, such as the F3 or a backcross generation) can then be screened for recombinant plants having the introgression fragment or a part thereof, using the molecular marker assays described herein.

In one aspect, the introgression fragment is from a wild relative of cucumber, which belongs to the Indian Cucumber Group, and which is transferred onto chromosome 3 of the Eurasian Cucumber Group, thereby creating a cultivated cucumber plant comprising yield QTL3.1 or a variant thereof. Thus, in one embodiment the introgression fragment comprising the yield QTL3.1 is derivable from (or derived from) or obtainable from (or obtained from; or as present in) a wild relative of cucumber which belongs to the Indian Cucumber Group.

In a specific embodiment, the introgression fragment comprising the yield QTL3.1 is derivable from (or derived from) or obtainable from (or obtained from; or as present in) seeds, a representative sample of which has been deposited under accession number NCIMB 42346, or from progeny thereof. The progeny may be any progeny which retain the one or more (or all) SNP markers indicative of (and linked to) the QTL, as described. Thus, progeny are not limited to F1 or F2 progeny of the deposit, but can be any progeny, whether obtained by selfing and/or crossing with another cucumber plant.

In one embodiment the introgression fragment is identifiable by one or more of the markers described elsewhere herein, especially markers SNP_01 to SNP_27 for the introgression fragment on chromosome 3, or a subset of markers, such as one or more of the markers selected from SNP markers SNP_01 to SNP_10, or from SNP markers SNP_10 to SNP_20, or from of the SNP markers SNP_20 to SNP_27, or from SNP markers SNP_06 to SNP_23. In one aspect the invention provides a cultivated cucumber plant, having a genome of cultivated (domesticated) cucumber which comprises enhanced fruit yield, wherein the enhanced fruit yield is conferred by an introgression fragment on the cultivated cucumber chromosome 3, wherein said introgression fragment is obtained by (or obtainable by) crossing a cultivated plant grown from seeds deposited under NCIMB 42346 or progeny of this plant (which comprises one or more the markers disclosed herein linked to the QTL) with a cultivated cucumber plant. Thus in one aspect the cultivated cucumber plant of the invention comprises the same introgression fragment and the same recombinant chromosome 3 as present in NCIMB42346 (comprising all of the wild relative of cucumber genotype for SNP markers SNP_01 to SNP_27), or it comprises a shorter fragment of that introgression fragment, whereby the shorter fragment retains the genetic element conferring enhanced fruit yield (QTL3.1).

Thus in one aspect the invention relates to a plant of the invention i.e. a cultivated *Cucumis sativus* var. *sativus* plant comprising an introgression fragment from a wild relative of cucumber on chromosome 3 in homozygous or heterozygous form and wherein said introgression fragment is the introgression fragment "as in"/is "identical to"/is "the same as in" the seeds deposited under number NCIMB 42346, or is a shorter fragment thereof, but still confers enhanced fruit yield due to the presence of QTL3.1.

In yet another embodiment the invention relates to a plant of the invention i.e. a cultivated *Cucumis sativus* var. *sativus* plant comprising an introgression fragment from a wild relative of cucumber on chromosome 3 in homozygous or heterozygous form and wherein said introgression fragment is the introgression fragment is a variant of the introgression fragment seeds deposited under number NCIMB 42346, i.e. it comprises the yield QTL 3.1, but the genomic sequence may be different. As wild accessions will be genetically divergent, the genomic sequence of an introgression fragment comprising QTL3.1 from other wild relatives of cucumber will most likely not be identical to the genomic sequence as introgressed into NCIMB42346, and even the yield conferring gene (comprising a promoter, introns and exons) may be divergent in nucleotide sequence, but the function will be the same, i.e. conferring enhanced fruit yield. The divergence can be seen in that certain SNP markers linked to QTL3.1 may be commonly found in various accessions, while other SNP markers may only be found in specific accessions. So for example not all of SNP_01 to SNP_27 may be found in other wild relatives of cucumber. However, the yield enhancing QTL3.1 (comprising e.g. a variant or ortholog of the yield allele) may still be present in such wild accessions. The skilled person is capable of identifying and introgressing the QTLs 3.1 comprising region found in other wild relatives of cucumber into cultivated cucumber, e.g. detecting wild relatives comprising the SNP markers or a subset thereof and transferring these SNP markers (or subset) into a cultivated cucumber line or variety and assessing the fruit yield of the cultivated line or variety compared to the line or variety lacking the SNP markers (or subset), i.e. lacking the introgression fragment.

In one embodiment the presence of the introgression fragment, or the chromosome 3 region (or variant or orthologous chromosome 3 region), comprising QTL3.1, is detectable by a molecular marker assay which detects at least 1, preferably at least 2, 3, 4, 5, 6, 7, 8, 9, 10, 11, 12, 13, 14, 15, 16, 17, 18, 19, 20, 21, 22, 23, 24, 25, 26 or more (or all 27) Single Nucleotide Polymorphism (SNP) markers selected from the group consisting of:

a) the TC or TT genotype for the Single Nucleotide Polymorphism marker SNP_01 in SEQ ID NO: 1 (or in a variant thereof);

b) the TC or TT genotype for the Single Nucleotide Polymorphism marker SNP_02 in SEQ ID NO: 2 (or in a variant thereof);

c) the TC or TT genotype for the Single Nucleotide Polymorphism marker SNP_03 in SEQ ID NO: 3 (or in a variant thereof);

d) the TC or TT genotype for the Single Nucleotide Polymorphism marker SNP_04 in SEQ ID NO: 4 (or in a variant thereof);

e) the GA or GG genotype for the Single Nucleotide Polymorphism marker SNP_05 in SEQ ID NO: 5 (or in a variant thereof);

f) the TC or TT genotype for the Single Nucleotide Polymorphism marker SNP_06 in SEQ ID NO: 6 (or in a variant thereof);

g) the TC or TT genotype for the Single Nucleotide Polymorphism marker SNP_07 in SEQ ID NO: 7 (or in a variant thereof);

h) the TC or TT genotype for the Single Nucleotide Polymorphism marker SNP_08 in SEQ ID NO: 8 (or in a variant thereof);

i) the CT or CC genotype for the Single Nucleotide Polymorphism marker SNP_09 in SEQ ID NO: 9 (or in a variant thereof);

j) the CT or CC genotype for the Single Nucleotide Polymorphism marker SNP_10 in SEQ ID NO: 10 (or in a variant thereof);

k) the TG or TT genotype for the Single Nucleotide Polymorphism marker SNP_11 in SEQ ID NO: 11 (or in a variant thereof);

l) the AG or AA genotype for the Single Nucleotide Polymorphism marker SNP_12 in SEQ ID NO: 12 (or in a variant thereof);

m) the TC or TT genotype for the Single Nucleotide Polymorphism marker SNP_13 in SEQ ID NO: 13 (or in a variant thereof);

n) the AG or AA genotype for the Single Nucleotide Polymorphism marker SNP_14 in SEQ ID NO: 14 (or in a variant thereof);

o) the CT or CC genotype for the Single Nucleotide Polymorphism marker SNP_15 in SEQ ID NO: 15 (or in a variant thereof);

p) the CT or CC genotype for the Single Nucleotide Polymorphism marker SNP_16 in SEQ ID NO: 16 (or in a variant thereof);

q) the GA or GG genotype for the Single Nucleotide Polymorphism marker SNP_17 in SEQ ID NO: 17 (or in a variant thereof);

r) the CT or CC genotype for the Single Nucleotide Polymorphism marker SNP_18 in SEQ ID NO: 18 (or in a variant thereof);

s) the GA or GG genotype for the Single Nucleotide Polymorphism marker SNP_19 in SEQ ID NO: 19 (or in a variant thereof);

t) the CT or CC genotype for the Single Nucleotide Polymorphism marker SNP_20 in SEQ ID NO: 20 (or in a variant thereof);

u) the AC or AA genotype for the Single Nucleotide Polymorphism marker SNP_21 in SEQ ID NO: 21 (or in a variant thereof);

v) the TC or TT genotype for the Single Nucleotide Polymorphism marker SNP_22 in SEQ ID NO: 22 (or in a variant thereof);

w) the CT or TT genotype for the Single Nucleotide Polymorphism marker SNP_23 in SEQ ID NO: 23 (or in a variant thereof);

x) the GA or GG genotype for the Single Nucleotide Polymorphism marker SNP_24 in SEQ ID NO: 24 (or in a variant thereof);

y) the GA or GG genotype for the Single Nucleotide Polymorphism marker SNP_25 in SEQ ID NO: 25 (or in a variant thereof);

z) the GA or GG genotype for the Single Nucleotide Polymorphism marker SNP_26 in SEQ ID NO: 26 (or in a variant thereof);

aa) the AG or AA genotype for the Single Nucleotide Polymorphism marker SNP_27 in SEQ ID NO: 27 (or in a variant thereof); and bb) optionally any wild relative of cucumber genome-specific marker in between marker SNP_01 and SNP_27.

In one aspect said at least 1, preferably at least 2 or 3, or at least 4, 5, 6, 7, 8, 9, 10, 11, 12, 13, 14, 15, 16, 17, 18, 19, 20, 21, 22, 23, 24, 25, 26 or 27 markers which are detected are consecutive markers.

Thus, in one embodiment the plants according to the invention comprise at least a Thymine (T) (i.e. the TT or TC genotype) instead of two Cytosines (CC) at nucleotide 75 of SEQ ID NO: 1 (referred to as SNP_01) or at the equivalent nucleotide of a genomic sequence comprising substantial sequence identity to SEQ ID NO:1 (in other words there is a Thymine at the physical position of chromosome 3 shown in Table 5);

and/or at least a Thymine (T) (i.e. the TT or TC genotype) instead of two Cytosine (CC) at nucleotide 75 of SEQ ID NO: 2 (referred to as SNP_02) or at the equivalent nucleotide of a genomic sequence comprising substantial sequence identity to SEQ ID NO:2 (in other words there is a Thymine at the physical position of chromosome 3 shown in Table 5);

and/or at least a Thymine (T) (i.e. the TT or TC genotype) instead of two Cytosine (CC) at nucleotide 75 of SEQ ID NO: 3 (referred to as SNP_03) or at the equivalent nucleotide of a genomic sequence comprising substantial sequence identity to SEQ ID NO:3 (in other words there is a Thymine at the physical position of chromosome 3 shown in Table 5);

and/or at least a Thymine (T) (i.e. the TT or TC genotype) instead of two Cytosine (CC) at nucleotide 75 of SEQ ID NO: 4 (referred to as SNP_04) or at the equivalent nucleotide of a genomic sequence comprising substantial sequence identity to SEQ ID NO:4 (in other words there is a Thymine at the physical position of chromosome 3 shown in Table 5);

and/or at least a Guanine (G) (i.e. the GG or GA genotype) instead of two Adenines (AA) at nucleotide 75 of SEQ ID NO: 5 (referred to as SNP_05) or at the equivalent nucleotide of a genomic sequence comprising substantial sequence identity to SEQ ID NO:5 (in other words there is a Guanine at the physical position of chromosome 3 shown in Table 5);

and/or at least a Thymine (T) (i.e. the TT or TC genotype) instead of two Cytosine (CC) at nucleotide 75 of SEQ ID NO: 6 (referred to as SNP_06) or at the equivalent nucleotide of a genomic sequence comprising substantial sequence identity to SEQ ID NO:6 (in other words there is a Thymine at the physical position of chromosome 3 shown in Table 5);

and/or at least a Thymine (T) (i.e. the TT or TC genotype) instead of two Cytosine (CC) at nucleotide 75 of SEQ ID NO:7 (referred to as SNP_07) or at the equivalent nucleotide of a genomic sequence comprising substantial sequence identity to SEQ ID NO:7 (in other words there is a Thymine at the physical position of chromosome 3 shown in Table 5);

and/or at least a Thymine (T) (i.e. the TT or TC genotype) instead of two Cytosine (CC) at nucleotide 75 of SEQ ID NO:8 (referred to as SNP_08) or at the equivalent nucleotide of a genomic sequence comprising substantial sequence identity to SEQ ID NO:8 (in other words there is a Thymine at the physical position of chromosome 3 shown in Table 5);

and/or at least a Cytosine (C) (i.e. the CC or CT genotype) instead of two Thymines (TT) at nucleotide 75 of SEQ ID NO:9 (referred to as SNP_09) or at the equivalent nucleotide of a genomic sequence comprising substantial sequence identity to SEQ ID NO:9 (in other words there is a Cytosine at the physical position of chromosome 3 shown in Table 5);

and/or at least a Cytosine (C) (i.e. the CC or CT genotype) instead of two Thymines (TT) at nucleotide 75 of SEQ ID NO:10 (referred to as SNP_10) or at the equivalent nucleotide of a genomic sequence comprising substantial sequence identity to SEQ ID NO:10 (in other words there is a Cytosine at the physical position of chromosome 3 shown in Table 5);

and/or at least a Thymine (T) (i.e. the TT or TG genotype) instead of two Guanines (GG) at nucleotide 75 of SEQ ID NO:11 (referred to as SNP_11) or at the equivalent nucleotide of a genomic sequence comprising substantial sequence identity to SEQ ID NO:11 (in other words there is a Thymine at the physical position of chromosome 3 shown in Table 5);

and/or at least an Adenine (A) (i.e. the AA or AG genotype) instead of two Guanines (GG) at nucleotide 75 of SEQ ID NO:12 (referred to as SNP_12) or at the equivalent nucleotide of a genomic sequence comprising substantial sequence identity to SEQ ID NO:12 (in other words there is a Adenine at the physical position of chromosome 3 shown in Table 5);

and/or at least a Thymine (T) (i.e. the TT or TC genotype) instead of two Cytosines (CC) at nucleotide 75 of SEQ ID NO:13 (referred to as SNP_13) or at the equivalent nucleotide of a genomic sequence comprising substantial sequence identity to SEQ ID NO:13 (in other words there is a Thymine at the physical position of chromosome 3 shown in Table 5);

and/or at least an Adenine (A) (i.e. the AA or AG genotype) instead of two Guanines (GG) at nucleotide 75 of SEQ ID NO:14 (referred to as SNP_14) or at the equivalent nucleotide of a genomic sequence comprising substantial sequence identity to SEQ ID NO:14 (in other words there is a Adenine at the physical position of chromosome 3 shown in Table 5);

and/or at least a Cytosine (C) (i.e. the CC or CT genotype) instead of two Thymines (TT) at nucleotide 75 of SEQ ID NO: 15 (referred to as SNP_15) or at the equivalent nucleotide of a genomic sequence comprising substantial sequence identity to SEQ ID NO:15 (in other words there is a Cytosine at the physical position of chromosome 3 shown in Table 5);

and/or at least a Cytosine (C) (i.e. the CC or CT genotype) instead of two Thymines (TT) at nucleotide 75 of SEQ ID NO: 16 (referred to as SNP_16) or at the equivalent nucleotide of a genomic sequence comprising substantial sequence identity to SEQ ID NO:16 (in other words there is a Cytosine at the physical position of chromosome 3 shown in Table 5);

and/or at least a Guanine (G) (i.e. the GG or GA genotype) instead of two Adenines (AA) at nucleotide 75 of SEQ ID NO: 17 (referred to as SNP_17) or at the equivalent nucleotide of a genomic sequence comprising substantial sequence identity to SEQ ID NO:17 (in other words there is a Guanine at the physical position of chromosome 3 shown in Table 5);

and/or at least a Cytosine (C) (i.e. the CC or CT genotype) instead of two Thymines (TT) at nucleotide 75 of SEQ ID NO: 18 (referred to as SNP_18) or at the equivalent nucleotide of a genomic sequence comprising substantial sequence identity to SEQ ID NO:18 (in other words there is a Cytosine at the physical position of chromosome 3 shown in Table 5);

and/or at least a Guanine (G) (i.e. the GG or GA genotype) instead of two Adenines (AA) at nucleotide 75 of SEQ ID NO:19 (referred to as SNP_19) or at the equivalent nucleotide of a genomic sequence comprising substantial sequence identity to SEQ ID NO:19 (in other words there is a Guanine at the physical position of chromosome 3 shown in Table 5);

and/or at least a Cytosine (C) (i.e. the CC or CT genotype) instead of two Thymines (TT) at nucleotide 75 of SEQ ID NO:20 (referred to as SNP_20) or at the equivalent nucleotide of a genomic sequence comprising substantial sequence identity to SEQ ID NO:20 (in other words there is a Cytosine at the physical position of chromosome 3 shown in Table 5);

and/or at least an Adenine (A) (i.e. the AA or AC genotype) instead of two Cytosines (CC) at nucleotide 75 of SEQ ID NO:21 (referred to as SNP_21) or at the equivalent nucleotide of a genomic sequence comprising substantial sequence identity to SEQ ID NO:21 (in other words there is a Adenine at the physical position of chromosome 3 shown in Table 5);

and/or at least a Thymine (T) (i.e. the TT or TC genotype) instead of two Cytosines (CC) at nucleotide 75 of SEQ ID NO:22 (referred to as SNP_22) or at the equivalent nucleotide of a genomic sequence comprising substantial sequence identity to SEQ ID NO:22 (in other words there is a Thymine at the physical position of chromosome 3 shown in Table 5);

and/or at least a Cytosine (C) (i.e. the CC or CT genotype) instead of two Thymines (TT) at nucleotide 75 of SEQ ID NO:23 (referred to as SNP_23) or at the equivalent nucleotide of a genomic sequence comprising substantial sequence identity to SEQ ID NO:23 (in other words there is a Cytosine at the physical position of chromosome 3 shown in Table 5);

and/or at least a Guanine (G) (i.e. the GG or GA genotype) instead of two Adenines (AA) at nucleotide 75 of SEQ ID NO:24 (referred to as SNP_24) or at the equivalent nucleotide of a genomic sequence comprising substantial sequence identity to SEQ ID NO:24 (in other words there is a Guanine at the physical position of chromosome 3 shown in Table 5);

and/or at least a Guanine (G) (i.e. the GG or GA genotype) instead of two Adenines (AA) at nucleotide 75 of SEQ ID NO:25 (referred to as SNP_25) or at the equivalent nucleotide of a genomic sequence comprising substantial sequence identity to SEQ ID NO:25 (in other words there is a Guanine at the physical position of chromosome 3 shown in Table 5);

and/or at least a Guanine (G) (i.e. the GG or GA genotype) instead of two Adenines (AA) at nucleotide 251 of SEQ ID NO:26 (referred to as SNP_26) or at the equivalent nucleotide of a genomic sequence comprising substantial sequence identity to SEQ ID NO:26 (in other words there is a Guanine at the physical position of chromosome 3 shown in Table 5);

and/or at least an Adenine (A) (i.e. the AA or AG genotype) instead of two Guanines (GG) at nucleotide 75 of SEQ ID NO:27 (referred to as SNP_27) or at the equivalent nucleotide of a genomic sequence comprising substantial sequence identity to SEQ ID NO:27 (in other words there is a Adenine at the physical position of chromosome 3 shown in Table 5).

In a further one embodiment the presence of the introgression fragment, or the chromosome 3 region (or variant or orthologous chromosome 3 region), comprising QTL3.1, is detectable by a molecular marker assay which detects at least 1, preferably at least 2, 3, 4, 5, 6, 7, 8, or more Single Nucleotide Polymorphism (SNP) markers of the sub-groups consisting of: SNP_01 to SNP10 or any wild relative of cucumber genome-specific marker physically located in between marker SNP_01 and SNP_10; SNP_10 to SNP_20 or any wild relative of cucumber genome-specific marker physically located in between marker SNP_10 and SNP_20; SNP_20 to SNP_27 or any wild relative of cucumber genome-specific marker physically located in between marker SNP_20 and SNP_27; or SNP_06 to SNP_23 or any wild relative of cucumber genome-specific marker physically located in between marker SNP_06 and SNP_23.

The SNP genotype refers to two nucleotides, and genomic sequences comprising one of these two nucleotides, one on each chromosome 3. So a plant having a TT genotype for SNP_01 has an identical nucleotide (T) on both chromosomes (i.e. is homozygous), while a plant having an TC genotype for SNP_01 has one chromosome with an T at nucleotide 75 of SEQ ID NO: 1 (or at the equivalent nucleotide of a genomic sequence comprising substantial sequence identity to SEQ ID NO:1) and one chromosome with a C at nucleotide 75 of SEQ ID NO: 1 (or at the equivalent nucleotide of a genomic sequence comprising substantial sequence identity to SEQ ID NO:1) and is heterozygous. As the genomic sequences around the SNP markers provided herein may vary slightly in introgression fragments from other wild relatives of cucumber (i.e. variants or orthologous chromosome 3 regions) it is clear that the nucleotide sequences before and after the SNP may not be 100% identical to the sequences provided herein. Therefore sequences having substantial sequence identity to the sequences provided herein (when aligned over the entire length as defined), but which comprise the same SNP, are encompassed herein.

In one aspect, the introgression fragment, or the chromosome 3 region (or variant or orthologous chromosome 3 region) comprising the QTL (QTL3.1 or variant), which is detectable by the above one or more markers is from a wild relative of cucumber, and in one aspect the wild relative is a member of the Indian Cucumber Group. In one aspect it is the same introgression fragment as found on chromosome 3 in seeds deposited under accession number NCIMB42346, or a smaller fragment retaining the QTL. SNP markers SNP_01 to SNP_27 span a region of about 5.7 Mb. In one aspect the introgression fragment on chromosome 3 is equal to or less than 10 Mb in size, preferably equal to or less than 8 Mb in size, more preferably equal to or less than 6, 5.7, 5, 4, 3 or 2.5 Mb in size, e.g. equal to or less than 2 Mb. In one aspect the introgression fragment is at least 0.2 Mb, 0.5 Mb, 1.0 Mb, 1.5 Mb, 1.9 Mb, 2.0 Mb, 2.5 Mb, 2.7 Mb or 3 Mb in size. Thus, various ranges of introgression sizes are encompassed herein, such as fragments less than 10 Mb but more than 0.2 Mb, less than 6 Mb or 3 Mb but more than 0.2 Mb, 0.5 MB or 1 Mb, etc., which retain the QTL3.1 and one or more of the SNP markers of SNP_01 to SNP_27, or of the subgroups of SNP_01 to SNP_10; SNP_10 to SNP_20; SNP_20 to SNP_27 or SNP_06 to SNP_23. As mentioned before, the location of the QTL3.1 in the region spanning SNP_01 to SNP_27 can be determined by finemapping and recombinants comprising QTL3.1 on a smaller introgression fragment can be generated. The size of an introgression fragment can be easily determined by e.g. whole genome sequencing or Next Generation Sequencing, e.g. as described in Qi et al. 2013 (supra) or in Huang et al. 2009 (supra). Especially introgression regions can be easily distinguished from cultivated genomic regions due to the larger amount of genetic variation (SNPs, INDELs, etc.) in the introgression region.

To obtain the introgression fragment present on chromosome 3 from the deposited seeds (NCIMB42346), i.e. to transfer the introgression fragments comprising the QTL to another cultivated cucumber plant, a plant is grown from the seed and the plant is crossed with a cultivated cucumber plant to obtain F1 seeds. As NCIMB42346 contains only one recombinant chromosome 3 (comprising the introgression fragment) only about half (50%) of the F1 seed and plants grown therefrom, contain one recombinant chromosome 3 from the NCIMB42346 parent and one non-recombinant chromosome 3 from the other cultivated parent. The other half F1 seeds do not contain a recombinant chromosome 3, but only two copies of the non-recombinant chromosome 3. Thus, by traditional breeding one can transfer the recombinant chromosome 3 from NCIMB42346 into other cultivated cucumber lines or varieties. Plants which comprise the QTL3.1 can be screened for, and selected for, by the presence of one or more of the above SNP markers in order to identify plants comprising a recombinant chromosome 3.

To generate shorter introgression fragments meiosis needs to take place and plants comprising the recombinant chromosomes 3, and especially new meiotic recombination events within the introgression fragment, need to be identified. For example, seeds of NCIMB42346 can be selfed one or more times to produce F1, F2 or F3 plants (or further selfing generations), and/or F1, F2 or F3 plants (etc.) comprising a recombinant chromosome 3 can be backcrossed to a cultivated parent. Plants which comprise the recombinant chromosome 3 can be screened for, and selected for, by the presence of one or more of the above SNP markers in order to identify plants comprising a smaller introgression fragment. Such new recombinants can then be tested for the presence of the QTL3.1 on the smaller introgression fragment by determining the average fruit yield compared to the (genetic) control lacking the introgression fragment.

Similarly, cultivated cucumber plants comprising QTL3.1 (or a variant thereof) can be generated and/or identified using different methods. For example, to obtain a cultivated cucumber plant comprising a introgression fragment from a wild relative of cucumber, first a wild relative of cucumber is identified which comprises one or more of the SNP markers linked to QTL3.1 disclosed herein, e.g. any one, or more, or all of the markers described herein above. The identified plant is crossed with a cultivated cucumber plant to obtain F1 seeds. The the F1 can be selfed to produce F2, F3, etc. plants, and/or F2 plants or F3 plants, etc., can be backcrossed to the cultivated cucumber parent. Plants which are comprising QTL3.1 (or a variant thereof) can be screened for, and/or selected for, by the presence of one or more of the above SNP markers and/or screened for, and/or selected for, an increased yield phenotype compared to the initial cultivated parent (lacking the introgressions). Alternatively or in addition, QTL mapping can be carried out in order to identify further molecular markers linked to the QTL3.1 (or a variant thereof) and/or to generate cultivated cucumber plants comprising an introgression fragment on chromosome 3 which confers significantly enhanced yield.

In one embodiment the presence of the introgression fragment in a cultivated cucumber plant, or the chromosome 3 region (or orthologous chromosome 3 region), comprising QTL3.1, is detectable by a molecular marker assay which detects at least one, two, three, four, five or more of the markers selected from the group consisting of:

a) the TT or TC genotype for the Single Nucleotide Polymorphism marker SNP_01 in SEQ ID NO: 1 (or in a variant thereof);

b) the AA or GA genotype for the Single Nucleotide Polymorphism marker SNP_27 in SEQ ID NO: 27 (or in a variant thereof);

c) any wild relative of cucumber genome-specific marker in between marker SNP_01 and SNP_27;

d) any wild-relative of cucumber genome-specific marker which is genetically linked within 7 cM, 5 cM, 3 cM or less of marker SNP_01 or SNP_27; and e) any wild-relative of cucumber genome-specific marker which is physically linked within 5 Mb, 3 Mb, 2 Mb, 1 Mb, 0.5 Mb or 0.2 Mb or less of marker SNP_01 or SNP_27.

In one aspect the markers of c) are one or more of SNP_02 to SNP_26. In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect the markers detected are consecutive markers.

In one embodiment the presence of the introgression fragment in a cultivated cucumber plant, or the chromosome 3 region (or orthologous chromosome 3 region), comprising QTL3.1, is detectable by a molecular marker assay which detects at least one, two, three, four, five or more of the markers selected from the group consisting of:
a) the TT or TC genotype for the Single Nucleotide Polymorphism marker SNP_01 in SEQ ID NO: 1 (or in a variant thereof);
b) the CC or CT genotype for the Single Nucleotide Polymorphism marker SNP_10 in SEQ ID NO: 10 (or in a variant thereof);
c) any wild relative of cucumber genome-specific marker in between marker SNP_01 and SNP_10;
d) any wild-relative of cucumber genome-specific marker which is genetically linked within 7 cM, 5 cM, 3 cM or less of marker SNP_01 or SNP_10; and
e) any wild-relative of cucumber genome-specific marker which is physically linked within 5 Mb, 3 Mb, 2 Mb, 1 Mb, 0.5 Mb or 0.2 Mb or less of marker SNP_01 or SNP_10.

In one aspect the markers of c) are one or more of SNP_02 to SNP_09. In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect the markers detected are consecutive markers.

In one embodiment the presence of the introgression fragment in a cultivated cucumber plant, or the chromosome 3 region (or orthologous chromosome 3 region), comprising QTL3.1, is detectable by a molecular marker assay which detects at least one, two, three, four, five or more of the markers selected from the group consisting of:
a) the CC or CT genotype for the Single Nucleotide Polymorphism marker SNP_10 in SEQ ID NO: 10 (or in a variant thereof);
b) the CC or CT genotype for the Single Nucleotide Polymorphism marker SNP_20 in SEQ ID NO: 20 (or in a variant thereof);
c) any wild relative of cucumber genome-specific marker in between marker SNP_10 and SNP_20;
d) any wild-relative of cucumber genome-specific marker which is genetically linked within 7 cM, 5 cM, 3 cM or less of marker SNP_10 or SNP_20; and
e) any wild-relative of cucumber genome-specific marker which is physically linked within 5 Mb, 3 Mb, 2 Mb, 1 Mb, 0.5 Mb or 0.2 Mb or less of marker SNP_10 or SNP_20.

In one aspect the markers of c) are one or more of SNP_11 to SNP_19. In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect the markers detected are consecutive markers.

In one embodiment the presence of the introgression fragment in a cultivated cucumber plant, or the chromosome 3 region (or orthologous chromosome 3 region), comprising QTL3.1, is detectable by a molecular marker assay which detects at least one, two, three, four, five or more of the markers selected from the group consisting of:
a) the CC or CT genotype for the Single Nucleotide Polymorphism marker SNP_20 in SEQ ID NO: 20 (or in a variant thereof);
b) the AA or GA genotype for the Single Nucleotide Polymorphism marker SNP_27 in SEQ ID NO: 27 (or in a variant thereof);
c) any wild relative of cucumber genome-specific marker in between marker SNP_20 and SNP_27;
d) any wild-relative of cucumber genome-specific marker which is genetically linked within 7 cM, 5 cM, 3 cM or less of marker SNP_20 or SNP_27; and
e) any wild-relative of cucumber genome-specific marker which is physically linked within 5 Mb, 3 Mb, 2 Mb, 1 Mb, 0.5 Mb or 0.2 Mb or less of marker SNP_20 or SNP_27.

In one aspect the markers of c) are one or more of SNP_21 to SNP_26. In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect the markers detected are consecutive markers.

In one embodiment the presence of the introgression fragment in a cultivated cucumber plant, or the chromosome 3 region (or orthologous chromosome 3 region), comprising QTL3.1, is detectable by a molecular marker assay which detects at least one, two, three, four, five or more of the markers selected from the group consisting of:
a) the TT or TC genotype for the Single Nucleotide Polymorphism marker SNP_06 in SEQ ID NO: 06 (or in a variant thereof);
b) the CC or CT genotype for the Single Nucleotide Polymorphism marker SNP_23 in SEQ ID NO: 23 (or in a variant thereof);
c) any wild relative of cucumber genome-specific marker in between marker SNP_06 and SNP_23;
d) any wild-relative of cucumber genome-specific marker which is genetically linked within 7 cM, 5 cM, 3 cM or less of marker SNP_06 or SNP_23; and
e) any wild-relative of cucumber genome-specific marker which is physically linked within 5 Mb, 3 Mb, 2 Mb, 1 Mb, 0.5 Mb or 0.2 Mb or less of marker SNP_06 or SNP_23.

In one aspect the markers of c) are one or more of SNP_07 to SNP_22. In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect the markers detected are consecutive markers.

Any wild-relative of cucumber genome-specific marker in between two markers refers to any molecular marker which maps genetically to the chromosome 3 region in-between the two markers and/or which lies physically in-between the two markers, and which is indicative of the wild-relative of cucumber chromosome 3 region. This means that the marker is polymorphic between the cultivated cucumber genome and the wild-relative of cucumber genome. In one aspect, the marker is a Single Nucleotide Polymorphism (SNP), but other molecular markers such as RFLP, AFLP, RAPD, DNA sequencing, etc. may equally be used.

The introgression fragment in the plants of the invention is in one aspect a fragment of the chromosome 3 which is present in seeds deposited under accession number NCIMB42346 or a smaller version of that fragment retaining the QTL (generated by e.g. recombination within the introgression fragment).

The introgression fragment is in one aspect equal to or less than 10 Mb in size, preferably equal to or less than 8 Mb, 5 Mb, 3 Mb, 2.5 Mb, 2 Mb, 1.5 Mb, 1 Mb in size. In a further aspect the introgression fragment is at least 0.5 Mb or at least 1 Mb in size.

Also provided are seeds from which a plant of the invention can be grown, as are cucumber fruits harvested from a plant of the invention and comprising the recombinant chromosome 3 in their genome. Likewise a plant cell, tissue or plant part of a plant or of a seed is provided comprising at least one recombinant chromosome 3, wherein said recombinant chromosome 3 comprises an introgression fragment from a wild relative of cucumber and wherein said introgression fragment comprises an allele conferring significantly enhanced fruit yield.

The molecular markers described herein may be detected according to standard method. For example SNP markers can easily be detected using a KASP-assay (see www.kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP assay method.

Thus, in one aspect, the SNP markers and the presence/absence of the marker associated with the yield QTL is determined using a KASP assay, but equally other SNP genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

The physical size of an introgression fragment can be determined by various methods, such as physical mapping, sequencing or by visualization of the introgression using Fluorescent in situ hybridization (FISH) images (Verlaan et al. 2011, Plant Journal 68: 1093-1103).

Cultivated cucumber plants with smaller introgression fragments on chromosome 3 can be generated by generating new recombinant plants from a population of plants derived from a cross between a cultivated cucumber plant (lacking the introgressions) and a plant of the invention and selecting recombinant progeny having smaller introgression sizes. Such plants are thus in one aspect derived from (progeny or descendants of) the recombinant chromosome 3 present in plants of which seeds have been deposited under NCIMB42346. Such progeny or descendants which retain the QTL3.1, and thus the higher yield compared to plants lacking an introgression as described herein, are encompassed herein.

In tomato, for example the large S. chilense introgression fragment on chromosome 6 (about 27 cM) which comprises the Ty-3 allele has been reduced by selecting a recombinant progeny line (LA1931-AL-F2), which comprises a much smaller S. chilense introgression fragment (about 6 cM) comprising Ty-3 (see Ji et al. 2007, Mol. Breeding 20: 271-284).

The cultivated cucumber plant according to the invention may be an inbred line, an OP (open pollinated variety) or an F1 hybrid. In one aspect the F1 hybrid comprises only one recombinant chromosome 3 (comprising the introgression fragment with the QTL), i.e. the F1 hybrid is heterozygous for the introgression fragment and the SNP marker described herein. Such an F1 hybrid is produced by crossing two inbred parent lines, one of which possesses the introgression fragment (preferably in homozygous form, although not necessarily) and collecting the F1 hybrid seeds from said cross. In another aspect the F1 hybrid may comprise the introgression fragment in homozygous form, i.e. produced by crossing two inbred parent lines, each comprising the introgression fragment in homozygous or heterozygous form.

The cultivated cucumber plant may be of any type. Preferably it has good agronomic and good fruit quality characteristics. The cultivated cucumber plant is in one aspect uniform, both genetically and phenotypically. Especially fruit characteristics are uniform, e.g. regarding shape, skin color, skin thickness, skin ribs, skin toughness, spines (spine color, spine density, etc.), presence/absence of warts, length and diameter at edible and marketable maturity, flavour, etc. Likewise seed characteristics (i.e. characteristics of the seeds from which the plant is grown) are uniform, e.g. seed size, seed color, etc. Thus, plants of the line or variety comprising the QTL in homozygous or heterozygous form produce uniform fruits, meaning that there is little variation between fruits of plants grown under the same environmental conditions and when fruits are at the same developmental stage (e.g. for qualitative characteristics at least 98%, 99% or preferably 100% of all plants or plant parts, fruits or seed are identical for the characteristics; for quantitative characteristics at least 90%, 95%, 98% of all plants or plant parts, fruits or seed are identical for the characteristics).

The cultivated cucumber plant comprising QTL3.1 (or a variant thereof) according to the invention may be of any type, e.g. it may be of one of the following cucumber types: pickling cucumbers (e.g. American pickling, European pickling type), slicing cucumbers (e.g. American slicing), long cucumbers, short cucumbers, European greenhouse cucumbers, Beit-Alpha type cucumbers, oriental trellis type cucumbers, Asian cucumbers (e.g. selected from Indian Mottled cucumber, Chinese Long cucumber, Korean cucumber and Japanese cucumber type). In one aspect the cultivated cucumber according to the invention is an inbred line or a F1 hybrid of a pickling cucumber type, slicing cucumber type, long cucumber type, short cucumber type, European greenhouse cucumbers, Beit-Alpha type cucumbers, oriental trellis type cucumbers, Chinese long cucumber type, Korean cucumber type or Japanese cucumber type. In a specific embodiment the cucumber is an inbred line or an F1 hybrid of a European greenhouse cucumber.

The plant may be a single cross F1 hybrid or an inbred line, comprising the QTL in homozygous or heterozygous form. In one aspect it is an F1 hybrid produced by crossing an (inbred) parent plant comprising QTL3.1 (or a variant) in homozygous form with an (inbred) parent plant lacking QTL3.1 (i.e. lacking introgression fragment comprising the QTLs). Thus in one aspect the F1 hybrid is heterozygous for QTL3.1.

In another aspect it is an F1 hybrid produced by crossing an (inbred) parent plant comprising QTL3.1 (or a variant thereof) in homozygous form with an (inbred) parent plant that also comprises QTL3.1 (or a variant thereof) in homozygous form. Thus, in one aspect the F1 hybrid is homozygous for QTL3.1.

In one aspect the F1 hybrid is a European greenhouse cucumber type, suitable for the traditional glasshouse cultivation or for high-wire cultivation. In the traditional glasshouse cultivation method the main stem of the plant is led up to a horizontal iron wire that is suspended at a height of about two meters above the ground. When the plant reaches this height and attaches to the wire, it is "topped" by removing its growth point in order to terminate further proliferation, whereupon lateral shoots start to develop. These lateral shoots are allowed to grow downward to a height of about 1 meter above the ground, and the growth points are then removed from them. This is followed by flowering and the development of the fruits both on the stem and on the lateral shoots or tendrils, but the fruits on the tendrils develop later than those on the stem. The fruits are harvested about 6 weeks after sowing. In the high-wire cultivation no lateral tendrils are allowed to grow and all the harvest comes from the stem. Specific varieties have been developed by Nunhems which are highly suitable for high-wire cultivation, as they provide a gene called "compact", see. WO2009/059777, for example varieties High-Jack, Hi-Power, Hi-Lisa.

Thus, in one aspect of the invention the cultivated cucumber plant comprises additionally the compact gene described in WO2009/059777. The compact gene is preferably present in heterozygous form.

In another aspect the introgression fragment of the invention is present in a long cucumber type, such as variety Kasja (Nunhems), which is a long cucumber variety producing fruits of 27-38 cm. A "long cucumber type" or "long cucumber plants" are greenhouse cucumbers characterized by fruits of at least about 26 cm or 27 cm to 37 or 38 cm in length or longer (for example 40 cm, 42 cm or more), preferably with parthenocarpic fruit formation. Examples of long cucumber types are the Sabrina and Korinda varieties, or cucumber plants that are awarded a score of 7-9 for the length of the fruit according to the CPVO Protocol (see Point 19 in Annex 1 to this protocol). Other long cucumber varieties are, for example, Bodega, Bologna, Kamaro, Flamingo, Discover, Kalunga, Kasja, Logica, Millagon. Nicola, Milika, Manuela, Frida, Activa, Alaya, Savanna, Sienna, Bella, Sheila, Bornand.

In one aspect the European greenhouse cucumber is the plant of which seeds were deposited under accession number NCIMB 42346, or progeny thereof, whereby the progeny retain QTL3.1 (as detectable by the presence of one or more markers as described elsewhere).

In another aspect the plant according to the invention is not a wild cucumber plant or a wild relative of cucumber or a landrace.

In yet another aspect the plant according to the invention is a cultivated cucumber of the Eurasian cucumber group, the East Asian cucumber group or the Xishuangbanna cucumber group. In another aspect the plant according to the invention is not a cucumber of the Indian cucumber group.

In one embodiment of the invention the cultivated cucumber plant comprising QTL3.1 (or a variant) produces seedless fruits without pollination, i.e. is parthenocarpic. Most European greenhouse cucumbers are parthenocarpic, i.e. the female flowers produce fruits without pollination, whereby the fruits remain seedless. Parthenocarpy is genetically controlled and it is known to breeders how to introduce the parthenocarpy trait into a cucumber line or variety (see e.g. Chapter 13 entitled "Cucumber" by T. tatlioglu, page 207-209 in the book Genetic Improvement of Vegetable Crops, Editors G. Kalloo and BO Bergh, Pergamon Press, 2012, ISBN0080408265).

In a further embodiment of the invention the cultivated cucumber plant comprising QTL3.1 (or a variant) is primarily gynoecious or entirely gynoecious (producing 100% female flowers). This means that mostly or only female flowers are produced. This trait is also genetically controlled and it is known to breeders how to introduce the gynoecious trait into a cucumber line or variety (see e.g. Chapter 13 entitled "Cucumber" by T. tatlioglu, page 207-209 in the book Genetic Improvement of Vegetable Crops, Editors G. Kalloo and BO Bergh, Pergamon Press, 2012, ISBN0080408265).

In one aspect the cucumber of the invention is both parthenocarpic and gynoecious. Thus, the plant produces primarily or only female flowers, which produce seedless fruits without pollination. In gynoecious cucumbers male flowers can be induced by treatment with silver nitrate. This method is used to produce pollen and to self-pollinate an inbred gynoecious cucumber line.

In a different aspect the cucumber plant of the invention is monoecious (produces both male and female flowers), optionally parthenocarpic and monoecious.

In a further embodiment of the invention the cultivated cucumber plant comprising QTL3.1 (or a variant) is uniform and genetically stable regarding the morphological characteristics of the fruits produced by said plant, e.g. regarding fruit shape, fruit color, skin thickness, warts, etc.

Fruit characteristics, such as average fruit length, average fruit diameter, skin thickness, presence/absence of warts, spininess, skin toughness, skin color, fruit neck shape, fruit tapering, shape of medial cross section, presence or absence of seeds (parthenocarpy), etc. depend on the cucumber type, i.e. the cultivated genetic background (gene pool) into which the QTL(s) is/are introgressed. Thus, depending on the cucumber type, various fruit shapes, sizes and fruit types are included herein. In one aspect the fruits are seedless.

The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

In one aspect the plant of the invention is a pickling type (processing type) and produces fruits which at edible maturity and/or marketable size have an average fruit length of at least 10 cm, or at least 11 cm, or at least 12 cm, or at least 13 cm and/or a fruit length to diameter ratio of at least 2, at least 2.5, at least 3, or more.

In a different aspect the plant of the invention is a fresh market type, e.g. a long cucumber type or slicing type, and produces fruits have an average fruit length at edible maturity and/or marketable size which is longer than the pickling type, e.g. at least 15 cm, 16 cm, 17 cm, 18 cm, 19 cm, 20 cm, 25 cm, 26 cm, 27 cm, 28 cm, 29 cm, 30 cm, 32 cm, 40 cm, or more.

In a preferred aspect the plant of the invention is a long cucumber type producing fruits of marketable size, especially seedless fruits. The fruits of marketable size, and parts thereof, and food or feed products containing these, are also encompassed herein. In one embodiment the SNP markers are detectable in the fruits, fruit parts or food or feed products comprising these.

In one embodiment the plant is an indeterminate cucumber. In another aspect the cucumber is determinate.

Also seeds from which a plant according to the invention can be grown are provided herein, as are cucumber fruits harvested from a plant according to the invention. These comprise the QTL(s) in their genome and can therefore be distinguished from other fruits by the presence of one or more of the SNP markers provided herein.

In one aspect the fruits are bitter free (selected from the groups bitter and bitterfree) at edible maturity and/or at marketable size of the fruits.

In a further aspect the fruit has a thin skin (selected from the groups thick and thin) at edible maturity and/or at marketable size of the fruits.

In a different embodiment the QTL(s) are introgressed into a cucumber type called 'Compact', as described in U.S. Pat. No. 8,710,303B2. Thus, the cucumber plants according to the invention comprise the compact gene as described in U.S. Pat. No. 8,710,303B2 in homozygous or heterozygous form, e.g. as present in varieties Hi-Jack and Hi-Lisa (both Nunhems).

A further embodiment of the invention is a plant cell, tissue or plant part of a plant or of a seed according to the invention comprising at least one recombinant chromosome 3, wherein said recombinant chromosome 3 comprises an introgression fragment from a wild relative of cucumber and wherein said introgression fragment comprises a QTL conferring enhanced fruit yield.

Also the use of a recombinant chromosome 3 comprising an introgression fragment from a wild relative of cucumber (said introgression fragment comprising an allele conferring enhanced fruit yield) for breeding cucumber varieties having enhanced fruit yield is encompassed herein. In one aspect said recombinant chromosomes 3 is the recombinant chromosome 3 as found in seeds deposited under accession number NCIMB 42346, or is derived from said recombinant chromosome 3 (e.g. is a smaller fragment of the introgression fragment found in said seeds).

Likewise, the use of a chromosome 3 as found in seeds deposited under accession number NCIMB 42346, or in progeny thereof, for generating a cultivated cucumber plant comprising an introgression fragment on said chromosome 3 is encompassed herein, wherein said introgression fragment confers enhanced fruit yield compared to the genetic control cucumber plant lacking said introgression fragment (such as plants grown from seeds deposited under NCIMB42345).

Similarly the use of plants grown from seeds deposited under accession number NCIMB 42346 or progeny thereof, for generating a cultivated cucumber plant comprising enhanced fruit yield is encompassed herein, wherein said enhanced fruit yield is conferred by an introgression fragment obtained from chromosome 3 of said plants or progeny thereof.

Also provided is the use of plants grown from seeds deposited under accession number NCIMB42346 or progeny thereof, for transferring QTL3.1 or the introgression fragment or a sub-fragment thereof comprising QTL3.1 to another cucumber plant is provided.

Also a method for identifying (detecting) a cultivated C. sativus var. sativus plant or plant part comprising an introgression fragment on chromosome 3 is provided, wherein said introgression fragment is as found in NCIMB 42346, or a smaller fragment derived therefrom, comprising:

a) providing a cultivated C. sativus var. sativus plant or plant parts or DNA of such plant or plant part,
b) screening said plant, plant part or DNA using a molecular marker assay which detects at least one SNP marker selected from the group consisting of:
SNP_01 to SNP_27 for detecting the introgression fragment on chromosome 3; and
c) identifying and/or selecting a plant comprising:
i) at least 1, 2, 3, 4, 5, 6, 7, 8, 9, 10 or more of the SNP markers of SNP_01 to SNP_27 for detecting the introgression fragment on chromosome 3; or
ii) at least 2, 3, 4 5, 6, 7, 8, 9, 10 or more consecutive markers selected from SNP_01 to SNP_27 for detecting the introgression fragment on chromosome 3; or
iii) at least 1, 2, 3, 4 5, 6, 7, 8 or more markers of a group, said group consisting of SNP_01 to SNP_10; SNP_10 to SNP_20; SNP_20 to SNP_27; SNP_06 to SNP_23; or
vi) at least 2, 3, 4 5, 6, 7, 8 or more consecutive markers of a group, said group consisting of SNP_01 to SNP_10; SNP_10 to SNP_20; SNP_20 to SNP_27; SNP_06 to SNP_23.

Further a method of producing C. sativus F1 hybrid plants comprising an introgression fragment conferring enhanced fruit yield is provided comprising:
a) providing a first inbred cucumber plant comprising a recombinant chromosome 3 in homozygous form having an introgression fragment comprising an allele conferring enhanced yield, optionally wherein said introgression fragment is as in NCIMB 42346 or a smaller fragment,
b) providing a second inbred cucumber plant,
c) crossing said cucumber plant of a) with said cucumber plant of b),
d) collecting F1 hybrid seeds from said cross.

The F1 hybrid seeds collected are also an embodiment of the invention.

In another aspect a method for generating progeny of NCIMB 42346 is provided, said method comprising:
a) growing a plant from seeds deposited under accession number NCIMB 42346;
b) selfing said plant one or more times and/or crossing said plant one or more times with another cucumber plant to generate progeny seeds;
c) screening said progeny seeds or plants grown from said seeds or parts of the seeds or plants using a molecular marker assay which detects at least one SNP marker selected from the group consisting of:
SNP_01 to SNP_27 for detecting the introgression fragment on chromosome 3;
d) identifying and/or selecting a progeny plant comprising:
i) at least 1 of the SNP markers of SNP_01 to SNP_27 for detecting the introgression fragment on chromosome 3; or
ii) at least 2, 3, or 4 consecutive markers selected from SNP_1 to SNP_27 for detecting the introgression fragment on chromosome 3; or
iii) at least 1, 2, or 3 markers of a group of markers consisting of SNP_1 to SNP_10; SNP_10 to SNP_20; SNP_20 to SNP_27; SNP_06 to SNP_23 for detecting the introgression fragment on chromosome 3; or
iv) at least 2, 3 or 4 consecutive markers of a group of markers consisting of SNP_1 to SNP_10; SNP_10 to SNP_20; SNP_20 to SNP_27; SNP_06 to SNP_23 for detecting the introgression fragment on chromosome 3.

The cucumber plant in step b is preferably a cultivated cucumber, such as a European greenhouse cucumber or long cucumber type.

The method optionally further comprises the step of identifying a progeny plant having enhanced fruit yield compared to the control.

A progeny plant generated by the above method is also an aspect of the invention. The progeny plant may comprise a shorter introgression fragment than the one found in NCIMB 42346, which retains the QTL3.1.

Also containers and packages containing or comprising seeds from which plants of the invention can be grown are provided herein. These may be labelled as containing cultivated cucumber seeds producing enhanced or high fruit yield.

Also progeny seeds and progeny plants of plants of the invention are provided, which retain the introgression on chromosome 3 comprising QTL3.1 (or a variant), or which comprise a smaller introgression (e.g. derivable from the fragment as is present in NCIMB 42346) which still confers enhanced yield, i.e. which still contains QTL3.1. Progeny may be any generation obtained by selfing a cucumber plant according to the invention and/or crossing a cucumber plant according to the invention with another cucumber plant one or more times. Progeny are, therefore, either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another cucumber plant (and/or with a wild relative of cucumber). Progeny are preferably selected to retain the recombinant chromosome 3 comprising the introgression fragment from a wild relative of cucumber. Thus progeny also have the increased yield phenotype, preferably at least the same yield as the plant used in the initial cross or selfing. The presence of (or retention of) the introgression fragment comprising the QTL can be determined phenotypically and/or using the molecular marker assay(s) described herein. Regarding phenotypic assessment, of course consideration needs to be given to the dominance nature of the QTL.

In a further aspect parts of the cucumber plants according to the invention are provided. Parts include for example cells and cell-cultures, tissue cultures, vegetative plant tissues (leaves, roots, etc.), flowers, pollen, embryos, fruits, parts of fruits, etc. The plant parts comprise the introgression fragment on chromosome 3, as described, and as can be detected using one or more of the markers described. Also, when whole plants are regenerated from such cucumber parts, such as cells, cell- or tissue cultures, the regenerated plants comprise the recombinant chromosome 3 and the yield phenotype.

Thus, also provided is a plant cell, tissue or plant part of a plant or of a seed according the invention comprising at least one recombinant chromosome 3, wherein said recombinant chromosome 3 comprises an introgression fragment from a wild relative of cucumber plant and wherein said introgression fragment comprises an allele conferring enhanced fruit yield.

Also in vitro cell cultures and in vitro tissue cultures are encompassed herein, of cells or tissues comprising a recombinant chromosome 3 described. Preferably the cells or tissues can be regenerated into a whole cucumber plant, i.e. the cells are regenerable cells and the tissues comprise regenerable cells. Thus, also vegetative propagations of the plants according to the invention are an embodiment herein. Thus, a vegetatively propagated cultivated cucumber plant is provided which comprises a recombinant chromosome 3 as described herein. In a different aspect non-propagating cells comprising QTL3.1 are encompassed herein, as are tissues comprising such cells.

In a specific aspect a cucumber fruit harvested from a plant according to the invention is provided. Marketable cucumber fruits, especially for the fresh market (slicing), are generally graded according to fruit size and quality characteristics after harvest. See e.g. the United States Standards for Grades of Cucumbers, US Department of Agriculture, Effective Mar. 1, 1985 and reprinted January 1997. Herein different grades of cucumbers are distinguished. Thus, in one aspect harvested fruits are provided of U.S. Fancy grade, U.S. Extra No. 1 grade, U.S. No. 1 grade, U.S. No. 1 Small grade, U.S. No. 1 Large grade, U.S. No. 2 grade. Also containers or packages comprising or consisting of harvested cucumber fruits are provided. Again, the cells of the fruits are distinguishable from other cucumber fruits by the presence of the recombinant chromosome 3 (as determinable in one or more of the molecular marker assays).

In another aspect the cucumber is a long cucumber type and fruits harvested and optionally processed (e.g. sliced or diced) are provided.

In another aspect the cucumber is a pickling type and fruits harvested and optionally pickled are provided.

The invention also provides for a food or feed product comprising or consisting of a plant part described herein preferably a cucumber fruit or part thereof and/or an extract from a plant part described herein. The food or feed product may be fresh or processed, e.g., pickled, canned, steamed, boiled, fried, blanched and/or frozen, etc. For example, containers such as cans, boxes, crates, bags, cartons, Modified Atmosphere Packaging, films (e.g. biodegradable films), etc. comprising plant parts such as fruits or fruit parts (fresh and/or processed) described herein are also provided herein.

Methods and Uses According to the Invention

In a further embodiment, the invention provides for a method of producing a new cultivated cucumber plant which comprises an introgression fragment on chromosome 3 (which confers enhanced yield) in homozygous or heterozygous form, as described. The method comprises crossing a plant of the invention, or a progeny plant thereof, either as male or as female parent, with a second cucumber plant (or a wild relative of cucumber) one or more times, and/or selfing a cucumber plant according to the invention, or a progeny plant thereof, one or more times, and selecting progeny from said crossing and/or selfing.

Thus, a method for transferring the recombinant chromosome 3, comprising the yield QTL3.1, from one (cultivated) cucumber plant into another (cultivated) cucumber plant is provided, especially into cucumber varieties or breeding lines for which the fruit yield should be increased.

The method comprises the steps of:

a) providing a first cultivate cucumber plant comprising a recombinant chromosome 3 having an introgression fragment comprising an allele conferring enhanced fruit yield in homozygous form, b) providing a second cultivated cucumber plant, especially a plant having a wild type (non-recombinant) chromosome 3, c) crossing said cucumber plant of a) with said cucumber plant of b), d) collecting F1 hybrid seeds from said cross, and e) optionally selfing the plant grown from said F1 hybrid seeds to produce F2 seeds or further selfing generations, and optionally selecting the F2 seeds or further selfing generation seeds having the recombinant chromosome 3, and f) optionally breeding further with plants grown from said F1 or F2 or further generation selfing seeds to produce a cucumber plant having good agronomic characteristics and comprising the introgression fragment in homozygous or heterozygous form.

The presence or absence of the recombinant chromosome 3, and of the introgression fragment, may be determined by one or more of the molecular marker assays described herein and/or by determining whether the yield is significantly increased compared to the plant of step b). Further breeding in step f) may comprise selfing, crossing, double haploid production, backcrossing, and combinations thereof (e.g. backcrossing and selfing), etc. Plants, plant parts and seeds obtainable by the above method are encompassed herein. In one aspect the plant of step a) may be a plant grown from seeds deposited under NCIMB42346, or progeny thereof, or a plant comprising the introgression fragment on chromosome 3 as present in seeds deposited under NCIMB42346, or a shorter fragment of that fragment.

Also provided is a method of producing cultivated cucumber F1 hybrid plants comprising a yield QTL on chromosome 3 comprising:
a) providing a first inbred cucumber plant comprising at least one recombinant chromosome 3 comprising an introgression fragment comprising a yield QTL selected from QTL3.1 or a variant thereof,
b) providing a second inbred cucumber plant comprising at least one recombinant chromosome 3 comprising an introgression fragment comprising a yield QTL selected from QTL3.1 or a variant thereof,
c) crossing said cucumber plant of a) with said cucumber plant of b),
d) collecting F1 hybrid seeds from said cross.

The inbred cucumber plant of a) and b) may be homozygous and/or heterozygous for the introgression fragment on chromosome 3, and they may contain introgression fragments of different sizes and/or of different origin, i.e. from different wild relatives of cucumber. So, for example the introgression fragment in a) may be the same or a different introgression fragment than in b). In one aspect the inbred cucumber plant of a) comprises QTL3.1 or a variant thereof in homozygous form and/or the inbred cucumber plant of b) comprises QTL3.1 or a variant thereof in homozygous form. In one aspect the introgression fragment comprising QTL3.1 is the fragment as found in NCIMB42346 or a smaller fragment thereof.

The F1 hybrid seeds preferably comprise at least one recombinant chromosome 3 and the F1 plants grown from the seeds do therefore produce enhanced fruit yield compared to the genetic control.

Plants and seeds obtainable by the above method are encompassed herein.

In a different aspect a method for producing a cultivated cucumber plant comprising an introgression fragment on chromosome 3, wherein said introgression fragment comprises a yield QTL, is provided, said method comprising the steps:
a) providing a first cultivated cucumber plant,
b) providing a second wild relative of cucumber, wherein said plant comprises QTL3.1 (or a variant thereof) as determinable by the presence of one or more SNP markers as described herein,
c) crossing said cucumber plant of a) with said cucumber plant of b),
d) collecting F1 seeds from said cross and backcrossing an F1 plant to the cucumber plant of a) to produce a backcross (BC1) population, or selfing said F1 plants one or more times to produce an F2 or F3 or higher generation selfing population,
e) optionally backcrossing a plant of d) one or more times to the cucumber plant of a) to produce a higher generation backcross population, and
f) identifying a F2, F3, or higher generation selfing, or BC1 or higher generation backcross plant which comprises an introgression on chromosome 3, wherein said introgression fragment comprises QTL3.1 (or a variant thereof).

When referring to backcross populations in the method, the backcross populations may also be selfed, i.e. BC1S1, BC1S2, BC2S1, BC2S2, or others.

In one or more of steps b) to f) the presence of the QTL (or the introgression fragment comprising the QTL) may be tested (and plants may be selected) by carrying out a molecular marker assay as described elsewhere herein, e.g. by determining whether the plant comprises the one or more of the SNP markers (e.g. one or more of SNP_01 to SNP_27; or one or more of SNP_01 to SNP_10; or one or more of SNP_10 to SNP_20; or one or more of SNP_20 to SNP_27; or one or more of SNP_06 to SNP_23; and/or any wild-relative of cucumber genome-specific marker in between any of these markers).

Using this method, one can generate and/or select new cultivated cucumber plants comprising an introgression with QTL 3.1 (or a variant) rom a wild source, such as a wild relative of cucumber.

In one aspect the method for producing a cultivated cucumber plant comprising an introgression fragment on chromosome 3, wherein said introgression fragment comprises a yield QTL, comprises the steps:
a) providing a first cultivated cucumber plant,
b) providing a second wild relative of cucumber comprising one or more of the SNP markers provided herein,
c) crossing said plant of a) with said plant of b),
d) collecting F1 seeds from said cross and backcrossing an F1 plant to the cucumber plant of a) to produce a backcross (BC1) population, or selfing said F1 plants one or more times to produce an F2 or F3 population,
e) optionally selfing the backcross population to produce e.g. a BC1S1 or BC1S2 population,
f) identifying a F2, F3, BC1, BC1S1, or BC1S2 plant which comprises the (one or more) SNP markers and/or any wild-relative of cucumber genome-specific marker in between the SNP markers.

Also provided is a method for identifying a wild relative of cucumber comprising a yield QTL on chromosome 3, said method comprising:
A) providing a wild relative of cucumber accession or several accessions;
B) screening said accession(s) using a molecular marker assay which detects at least one (or at least 2, 3, 4, 5, 6, 7, 8, 9, 10 or more) SNP marker selected from the group consisting of: SNP_01 to SNP_27 (or of subgroups of SNP markers, such as SNP_01 to SNP_10; SNP_10 to SNP_20; SNP_20 to SNP_27; SNP_06 to SNP_23);
C) identifying and/or selecting an accession from b) comprising at least one or more of the following markers:
  a) the TC or TT genotype for the Single Nucleotide Polymorphism marker SNP_01 in SEQ ID NO: 1 (or in a variant thereof);
  b) the TC or TT genotype for the Single Nucleotide Polymorphism marker SNP_02 in SEQ ID NO: 2 (or in a variant thereof);

c) the TC or TT genotype for the Single Nucleotide Polymorphism marker SNP_03 in SEQ ID NO: 3 (or in a variant thereof);
d) the TC or TT genotype for the Single Nucleotide Polymorphism marker SNP_04 in SEQ ID NO: 4 (or in a variant thereof);
e) the GA or GG genotype for the Single Nucleotide Polymorphism marker SNP_05 in SEQ ID NO: 5 (or in a variant thereof);
f) the TC or TT genotype for the Single Nucleotide Polymorphism marker SNP_06 in SEQ ID NO: 6 (or in a variant thereof);
g) the TC or TT genotype for the Single Nucleotide Polymorphism marker SNP_07 in SEQ ID NO: 7 (or in a variant thereof);
h) the TC or TT genotype for the Single Nucleotide Polymorphism marker SNP_08 in SEQ ID NO: 8 (or in a variant thereof);
i) the CT or CC genotype for the Single Nucleotide Polymorphism marker SNP_09 in SEQ ID NO: 9 (or in a variant thereof);
j) the CT or CC genotype for the Single Nucleotide Polymorphism marker SNP_10 in SEQ ID NO: 10 (or in a variant thereof);
k) the TG or TT genotype for the Single Nucleotide Polymorphism marker SNP_11 in SEQ ID NO: 11 (or in a variant thereof);
l) the AG or AA genotype for the Single Nucleotide Polymorphism marker SNP_12 in SEQ ID NO: 12 (or in a variant thereof);
m) the TC or TT genotype for the Single Nucleotide Polymorphism marker SNP_13 in SEQ ID NO: 13 (or in a variant thereof);
n) the AG or AA genotype for the Single Nucleotide Polymorphism marker SNP_14 in SEQ ID NO: 14 (or in a variant thereof);
o) the CT or CC genotype for the Single Nucleotide Polymorphism marker SNP_15 in SEQ ID NO: 15 (or in a variant thereof);
p) the CT or CC genotype for the Single Nucleotide Polymorphism marker SNP_16 in SEQ ID NO: 16 (or in a variant thereof);
q) the GA or GG genotype for the Single Nucleotide Polymorphism marker SNP_17 in SEQ ID NO: 17 (or in a variant thereof);
r) the CT or CC genotype for the Single Nucleotide Polymorphism marker SNP_18 in SEQ ID NO: 18 (or in a variant thereof);
s) the GA or GG genotype for the Single Nucleotide Polymorphism marker SNP_19 in SEQ ID NO: 19 (or in a variant thereof);
t) the CT or CC genotype for the Single Nucleotide Polymorphism marker SNP_20 in SEQ ID NO: 20 (or in a variant thereof);
u) the AC or AA genotype for the Single Nucleotide Polymorphism marker SNP_21 in SEQ ID NO: 21 (or in a variant thereof);
v) the TC or TT genotype for the Single Nucleotide Polymorphism marker SNP_22 in SEQ ID NO: 22 (or in a variant thereof);
w) the CT or TT genotype for the Single Nucleotide Polymorphism marker SNP_23 in SEQ ID NO: 23 (or in a variant thereof);
x) the GA or GG genotype for the Single Nucleotide Polymorphism marker SNP_24 in SEQ ID NO: 24 (or in a variant thereof);
y) the GA or GG genotype for the Single Nucleotide Polymorphism marker SNP_25 in SEQ ID NO: 25 (or in a variant thereof);
z) the GA or GG genotype for the Single Nucleotide Polymorphism marker SNP_26 in SEQ ID NO: 26 (or in a variant thereof);
aa) the AG or AA genotype for the Single Nucleotide Polymorphism marker SNP_27 in SEQ ID NO: 27 (or in a variant thereof);
bb) any wild relative of cucumber genome-specific marker in between marker SNP_01 and SNP_27, and optionally
D) introgressing said QTL from said wild accession into cultivated cucumber (e.g. by backcrossing).

In step B), C) and D) also other molecular marker tests described elsewhere herein can be used. With this method one can, thus, screen wild relatives of cucumber for the presence of one or more of the markers and, thus, the presence of QTL3.1 (or a variant thereof) and introgress the QTL into cultivated cucumber plants. Plants and seeds obtained by this method are also an embodiment of the invention.

In still another aspect a method for identifying a cultivated cucumber plant comprising an introgression fragment on chromosome 3, wherein said introgression fragment comprises a yield QTL, is provided, said method comprising: screening a cultivated cucumber plant or a population of cultivated cucumber plants or parts of such cucumber plants (e.g. fruits, cells, DNA) using a molecular marker assay which detects at least one SNP marker (preferably 2, 3, 4, 5 or more; preferably consecutive SNP markers) indicative of (linked to) QTL3.1 as described elsewhere herein.

In this method any of the molecular marker tests described elsewhere herein can be used. Thus, using this method one can detect the presence of an introgression fragment on chromosome 3 and comprising QTL3.1 in cultivated cucumber plants or plant parts.

In yet another aspect a method for detecting whether a cultivated cucumber plant comprises an introgression fragment on chromosome 3, wherein said introgression fragment comprises QTL3.1, is provided, said method comprising:
a) providing cultivated cucumber plant or a plant part,
b) screening said plant or said plant part (or DNA obtained from said plant or plant part) using a molecular marker assay which detects at least one (preferably at least 2, 3, 4, 5 or more) SNP marker selected from the group consisting of:
SNP_01 to SNP_27 and/or any wild-relative of cucumber genome-specific marker in between the marker SNP_01 and SNP_27.

Molecular marker screening obviously involves obtaining plant material and analyzing the genomic DNA of the material for the marker genotype.

In this method also other molecular marker tests described elsewhere herein can be used.

Also encompassed herein is a method for producing a cultivated cucumber plant comprising an introgression fragment on chromosome 3, wherein said introgression fragment comprises QTL3.1, comprising:
a) providing a first cultivated cucumber plant lacking an introgression fragment comprising QTL3.1,
b) providing a second cultivated cucumber plant selected from plants grown from seeds deposited under accession number NCIMB42346 or progeny thereof;
c) crossing said plant of a) with said plant of b), d) collecting F1 seeds from said cross and optionally selfing said F1 plants one or more times to produce an F2 or F3 or further selfing population,
e) optionally backcrossing the F1 plant or an F2 or F3 or further selfing plant to the plant of a) to produce a backcross population,
f) optionally selfing the backcross population one or more times,
g) identifying a F1, F2, F3, further selfing or backcross plant which comprises one or more or all of the SNP marker genotypes indicative of the introgression fragment on chromosome 3.

In a further aspect a method of producing F1 hybrid plants is provided comprising:
a) providing a first inbred cucumber plant comprising at least one recombinant chromosome 3 having an introgression fragment comprising QTL3.1, wherein said introgression fragment is the fragment as found in NCIMB42346, or a shorter fragment of that introgression fragment,
b) providing a second inbred cucumber plant with or without a recombinant chromosome 3,
c) crossing said plant of a) with said plant of b),
d) collecting F1 hybrid seeds from said cross.

In another aspect a method for generating progeny of NCIMB42346 retaining QTL3.1 is provided, said method comprising:
a) growing a plant from seeds deposited under accession number NCIMB42346;
b) selfing said plant one or more times or crossing said plant one or more times with another cultivated cucumber plant to generate progeny seeds;
c) screening said progeny seeds or plants grown from said seeds or parts of the seeds or plants using a molecular marker assay which detects at least one SNP marker disclosed herein;
d) identifying and/or selecting a progeny plant comprising at least one, two, three or more of the SNP markers indicative of the introgression fragment comprising the QTL3.1 (as described elsewhere herein); and
e) optionally confirming the enhanced fruit yield of said progeny plants.

In one aspect the yield in e) is preferably at least the same yield as for plants grown from NCIMB43246 when grown under the same conditions.

A method for generating progeny of NCIMB 42346 is provided, said method comprising:
a) growing a plant from seeds deposited under accession number NCIMB 42346;
b) selfing said plant one or more times or crossing said plant one or more times with another cucumber plant to generate progeny seeds;
c) screening said progeny seeds or plants grown from said seeds or parts of the seeds or plants using a molecular marker assay which detects at least one SNP marker selected from the group consisting of:
SNP_01 to SNP_27 for detecting the introgression fragment on chromosome 3;
d) identifying and/or selecting a progeny plant comprising:
i) at least 1 of the SNP markers of SNP_01 to SNP_27 for detecting the introgression fragment on chromosome 3; or
ii) at least 2, 3, or 4 consecutive markers selected from SNP_01 to SNP_27 for detecting the introgression fragment on chromosome 3, and
e) optionally confirming the enhanced fruit yield of said progeny plants.

In one aspect the yield in e) is preferably at least the same yield as for plants grown from NCIMB43246 when grown under the same conditions.

A progeny plant generated by any of the above methods is also an aspect of the invention.

One can also use the methods and the markers described herein to reduce the size of the introgression fragment comprising the QTL, i.e. to generate and select recombinants having a smaller introgression fragment on chromosome 3, but which retain the yield enhancing part of the introgression fragment.

In one aspect the invention encompasses the use of a recombinant chromosome 3 comprising an introgression fragment from a wild relative of cucumber, said introgression fragment comprising a yield QTL, for breeding cucumber varieties having enhanced fruit yield.

Also provided is the use of a chromosome 3 as found in seeds deposited under accession number NCIMB42346 or progeny thereof for generating cultivated cucumber plant comprising an introgression fragment of said chromosome 3.

Also provided is the use of plants grown from seeds deposited under accession number NCIMB 42346, or progeny thereof, for generating a cultivated cucumber plant comprising enhanced fruit yield, wherein said enhanced fruit yield is conferred by an introgression fragment obtained from chromosome 3 of said plants or progeny.

DNA and Chromosomes According to the Invention

In one aspect a modified (recombinant) cultivated cucumber chromosome 3 is provided herein, which comprises an introgression fragment of a wild relative of cucumber, as described throughout the specification. In one aspect the recombinant chromosome is isolated from its natural environment. In another aspect it is in a plant cell, especially in a cucumber cell, especially in a cultivated cucumber cell. Also an isolated part of the recombinant chromosome comprising the QTL is provided herein.

In a further aspect a recombinant nucleic acid molecule, especially a recombinant DNA molecule, is provided which comprises a yield-allele according to the invention. In one aspect the yield-allele is detectable by one or more of the molecular marker assays described herein. Also a DNA vector is provided comprising the recombinant DNA. The recombinant DNA molecule or DNA vector may be an isolated nucleic acid molecule. The DNA comprising the yield-allele may be present in a microorganisms, such as a bacterium (e.g. *Agrobacterium*).

The use of such a (isolated or extracted) nucleic acid molecule and/or of such a recombinant chromosome or part thereof for generating plant cells and plants comprising a yield-allele is encompassed herein. In one aspect it may be used to generate transgenic plant cells and transgenic plants, e.g. cucumber cells, cucumber plants and parts (e.g. fruits) comprising the yield allele and the plant comprises an enhanced fruit yield phenotype.

Thus, transgenic plant cells, e.g. transgenic cucumber cells, comprising in their genome a recombinant chromosome 3 as described and/or a recombinant nucleic acid molecule comprising a yield-allele are also an embodiment of the invention. In one aspect the DNA molecule comprising the yield-allele is stably integrated into the cucumber genome.

The yield-allele may also be cloned and a chimeric gene may be made, e.g. operably linking a plant expressible promoter to the yield allele. Such a chimeric gene may be introduced into a plant cell and the plant cell may be regenerated into a whole plant to produce a transgenic plant. In one aspect the transgenic plant is a cucumber plant, or a melon plant.

Thus, transgenic plants, especially transgenic cultivated cucumber or melon plants, comprising a yield allele and having increased fruit yield are provided herein.

Especially cells or cell cultures comprising a recombinant chromosome 3 according to the invention are an embodiment, independent whether the recombinant chromosome 3 is introduced by transgenic methods or by breeding methods. The cells are e.g. in vitro and are regenerable into plants comprising the recombinant chromosome 3 of the invention.

Also the molecular marker sequences (and isolated nucleic acid molecules comprising the sequence) disclosed herein and molecular markers in between any of the mentioned molecular markers described herein, linked to the yield QTL3.1, and their use in detecting and/or generating cucumber plants comprising said QTLs are encompassed herein.

Seed Deposits

A representative sample of seeds of a hybrid *Cucumis sativus* var. *sativus* of the long cucumber type, designated CUCYLD-3, comprising an introgression fragment comprising QTL3.1 in heterozygous form, and the genetic control (GC) lacking the introgression fragment and the QTL, designated CUYLD-GC, were deposited by Nunhems B. V. on 17 Dec. 2014 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers NCIMB 42346 (CUCYLD-3) and NCIMB 42345 (CUYLD-GC).

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising QTL3. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

EXAMPLES

Example 1—Identification of Yield QTLs

Population Development

A wild relative of cucumber accession obtained from the USA was crossed with a proprietary long cucumber breeding line, HMRKC, in the breeding program for the North-European and North-American greenhouse cucumber market. HMRKC is an elite line for the long greenhouse cucumber program.

A QTL-discovery population has been developed out of the cross between HMRKC and the wild accession. During population development only female flowering plants have been kept as to facilitate yield measurements.

SNP markers have been used during several generations to select for long fruits and to optimize for genome coverage and homozygosity. A BC2S2 population was used to construct a genetic map.

220 BC2S2 plants were self-pollinated to generate BC2S3's. The BC2S2 plants were also crossed with an elite line from the breeding program, line CUZL0176, to create test hybrids. Also a genetic control was generated by crossing HMRKC with CUZL0176. The 220 test hybrids and the genetic control were used in yield trials.

Yield Experiments

The aim of the yield experiment was to measure yield for long glasshouse cucumbers during the summer-autumn period in the Netherlands. The experiment consisted of the 220 test-hybrids and 30 repeats of the genetic control.

Thus, 250 plots were sown in June 2009 by hand in trays with rockwool plugs. The trays were kept during 4 days at a temperature of at least 24° C. 4 days after sowing the plugs with germinated seeds were transplanted on rockwool blocks. During approximately 3 weeks the rockwool pots were kept in a specific compartment of the greenhouse, the plant-raising area. In this area the plants will grow until they were ready for planting in the greenhouse.

The plants of roughly 30 cm height were transported to the grower about 4 weeks after sowing. At the grower 8 plants per plot were maintained. In total the experiment consisted of 250 plots*8 plants. The exact number of plants per plot was recorded. The plants were grown in the traditional Dutch way. That means that the plants were grown vertically, supported by a wire up to roughly 220 cm height. At this height the top of the plant is removed and the plant continues growing on the laterals. About 3 weeks after transplantation the first fruits can be harvested (i.e. are of marketable size). The harvest period started in August and continued until the end of October. Plants were harvested by hand 3 to 7 times per week by picking marketable fruits.

The yield was measured in two different ways. The total number of harvested fruits per plot was counted and divided by the number of plants of that plot. This results in the yield expressed in (average) number of fruits per plant (FrPP). The second measurement was to take the weight per plot and divide that by the number of plants to obtain the (average) yield in gram per plant (GrPP).

In 2009 two experiments have been carried out in The Netherlands.

The yield data was used for QTL detection analysis. A QTL on chromosome 3 was detected with a peak (LOD score 6.3) at 89.347 cM of the genetic map (the LOD interval started at position 76.214 cM and ended at 93.377 cM of chromosome 3).

Table 1 and Table 2 show the performance of the test-hybrids with an introgression from the wild cucumber relative on chromosome 3 versus the genetic control lacking the introgression on chromosome 3. The yield increase due to QTL3.1 was on average, for the two trials, 6% when expressed in GrPP and 16% when expressed in FrPP.

TABLE 1

Yield of test-hybrids containing an introgression on chromosome 3 (QTL3.1) versus the genetic control hybrid (generated by crossing HMRKC with CUZL0176) lacking the introgression on chromosome 3. Yield data is based on 2 trials in the Netherlands (NL)

|  | Yield in average gram per plant (GrPP) NL-Trial 1 | Yield in average gram per plant (GrPP) NL-Trial 2 |
| --- | --- | --- |
| Genetic control hybrid (lacking QTL3.1) | 17957 | 12085 |
| Test-hybrids with QTL3.1 introgression | 19259 | 12649 |
| Yield increase due to QTL3.1 introgression | 7% | 5% |

TABLE 2

Yield of test-hybrids containing an introgression on chromosome 3 (QTL3.1) versus the genetic control hybrid (generated by crossing HMRKC with CUZL0176) lacking the introgression on chromosome 3. Yield data is based on 2 trials in the Netherlands (NL)

|  | Yield in average fruits per plant (FrPP) NL-Trial 1 | Yield in average fruits per plant (FrPP) NL-Trial 2 |
| --- | --- | --- |
| Genetic control hybrid (lacking QTL3.1) | 40.8 | 29.6 |
| Test-hybrids with QTL3.1 introgression | 47.4 | 34.4 |
| Yield increase due to QTL3.1 introgression | 16% | 16% |

Based on the results of the QTL-detection trials, one particular BC2S3-line, containing the introgression on chromosome 3, was selected. This BC2S3 line was crossed with the elite line CUZL0176 to create the test-hybrid called PRE.N1.1168. The BC2S3 line was also backcrossed to elite line HMRKC to create a BC3. The BC3 was self-pollinated twice to create a BC3S2 line only containing the introgressions on chromosome 3 from the wild relative of cucumber.

This BC3S2 line was crossed with elite line CUZL0176, to create a new test-cross hybrid of which seeds were deposited under Accession number NCIMB42346. NCIMB42346 has the introgression from the wild relative of cucumber comprising the QTL3.1 on chromosome 3. Thus NCIMB42346 is heterozygous for QTL3.1.

For comparison the elite line HMRKC was crossed with the elite line CUZL0176 creating the genetic control hybrid, seeds of which were deposited under Accession number NCIMB42345.

Two yield trials with PRE.N1.1168 were performed in 2011. Both trials were carried out starting in June and ending in October 2011. The harvest of both trials was from week 31 until week 43. Table 3 shows that the average yield increase of the two trials was 20% expressed in (average) fruits per plant. The average yield increase of the two trials, expressed in (average) gram per plant, was 10% (data not shown).

TABLE 3

Yield trial 2011, 2 trials and 4 replicates per trial

|  | FrPP (average fruits per plant) Trial 1 | FrPP (average fruits per plant) Trial 2 |
| --- | --- | --- |
| NCIMB42345 (genetic control, lacking QTL3.1) | 35.0 | 29.9 |
| PRE.N1.1168 -(comprising QTL3.1) | 43.5 | 34.7 |
| Yield increase due to QTL3.1 | 24% | 16% |

Another yield trial has been carried out in 2014 with NCIMB42346, comprising QTL3.1, and the genetic control NCIMB42345. This trial has been carried out in the period from June to September 2014 in the Netherlands. Fruits were harvested from week 29 until week 39. NCIMB42346 and the genetic control NCIMB42345 were planted in 8 replicates.

Table 4 shows that yield increase due to QTL3.1 expressed in average fruits per plant was 3.4%. The yield increase in average grams per plant was 2.2%.

TABLE 4

Yield trial 2014, 8 replicates. Yield is expressed in average fruits harvested per plant (FrPP) and average gram harvested per plant (GrPP)

|  | FrPP | GrPP |
| --- | --- | --- |
| NCIMB42345 (genetic control, lacking QTL3.1) | 38.7 | 15781 |
| NCIMB42346 (comprising QTL3.1) | 40.0 | 16130 |
| Yield increase due to QTL3.1 | 3.4% | 2.2% |

Example 2

Single Nucleotide Polymorphism markers (SNPs) were identified spanning the introgression fragment and their position on the physical *C. sativus* map was determined.

TABLE 5

SNP markers for QTL3.1 introgression fragment

| SNP marker | Physical position of the SNP (base number) | Genotype of introgression on fragment (homozygous), i.e. this is the genotype of the wild relative of cucumber or donor | Genotype of recurrent parent lacking introgression (HMRKC), i.e. this is the genotype of cultivated cucumber | Genotype of hybrid (heterozygous for the introgression fragment compromsing QTL3.1) | Genomic sequence compromising the SNP (highlighted in bold) |
|---|---|---|---|---|---|
| SNP_01 | 21,507,892 | TT | CC | TC | TTAAAACAACAATAAAAAC AGACATGCAGCATGCAGCA TACTAATGATATCACTGAG AAAAACAAAGCCCCCGT[C/T] GGAAAAATCAAAAACA ATATTTCAAAAAGACCAGT AAAAAGATAAGCGAATAGA GAATAAATGAAAAAATATA AG (SEQ ID NO: 1) |
| SNP_02 | 21,719,917 | TT | CC | TC | TTCACTCACATTYTGCCCC TGAATATAGCTAACGGGAA AGTAACATCCATAGTGACA AAGTATTTCCTGGACGA[C/T] AGGTGAAAACATTTAT AACCATGCTGGTGAAAGGG ATACCCAACAAACACAMAT GYCTGAGCTCGATGGGTAA AT (SEQ ID NO: 2) |
| SNP_03 | 21,943,026 | TT | CC | TC | cAAAAGATATGGATCAAKT TTGAGGTCATATTAAAAAA ATGAACTTCCTTTAGCTTA GACCACATTTACAAATG[C/T] GTAACATAGTTTGATT GTTTTTTCTTTAATCATAT TTCTTAATATTACAAATAA CTCATTAACTCKAACATTA AA (SEQ ID NO: 3) |
| SNP_04 | 22,305,217 | TT | CC | TC | CCACTTCTTAAAAATAAAT GAAAAGAGGCATTTGGTGT TACCTGTCCACATGTCTTG ACTTCACGAATATCACT[C/T] GATACTTGATGTTCGA CTACTCGGTGCATGCTACT CAACACACAATTCCTCGTT ACATGTTTTACAATAAACA AT (SEQ ID NO: 4) |
| SNP_05 | 22,532,533 | GG | AA | GA | CTTTATGTGTGGAGCATTT TATCCATACATATATTTGA AGAAAAAACTAATTAAAAG TACCTCACATCACAATC[A/G] TGTTCAAAGTGTATTT AAATTACAATTTTTTTAGT GCCATGGTTAGAGGAGCTT TAATTTATTTTTATGAGTA GA (SEQ ID NO: 5) |
| SNP_06 | 23,091,618 | TT | CC | TC | TTAAACTTGGACTTGAATT GGGTTATGACTTCCGTTGT AGGATTGCTCATTGACTGT TCAACAACTCGAACACT[C/T] TTTCAATATCATTCAG VTGTAAAAGAATGTTTCATG TTAAAGAACTTTTGCGTTG TTGTTGGTGCATTACATCC AC (SEQ ID NO: 6) |

TABLE 5-continued

SNP markers for QTL3.1 introgression fragment

| SNP marker | Physical position of the SNP (base number) | Genotype of introgression on fragment (homozygous), i.e. this is the genotype of the wild relative of cucumber or donor | Genotype of recurrent parent lacking introgression (HMRKC), i.e. this is the genotype of cultivated cucumber | Genotype of hybrid (heterozygous for the introgression fragment comprosming QTL3.1) | Genomic sequence compromising the SNP (highlighted in bold) |
|---|---|---|---|---|---|
| SNP_07 | 23,302,402 | TT | CC | TC | ATTATGCGAACAACCGTTACTAATCCATTTCTATATAAACAAGAGGTCCCATAATTAACCTTTGAGGTACACTT[C/T]GAACTTCCTATGCTCTCTGGCTCTCTCTAAACAATGACTAACTTGATGTTGGAGTGTTGATGCCCAACCACCACA (SEQ ID NO: 7) |
| SNP_08 | 23,302,402 | TT | CC | TC | ATTATGCGAACAMCCGTTACTAATCCATTTCTATATAAACAAGAGGTCCCATAATTAACCTTTGAGGTACACTT[C/T]GAACTTCCTATGCTCTCTGGCTCTCTCTAAACAATGACTAACTTGATGTTGGAGTGTTGATGCCCAACCACCACA (SEQ ID NO: 8) |
| SNP_09 | 23,491,579 | CC | TT | CT | ATTTCAATCTCTTCTAAACAAGGAAATTATTTGTACCAGATGAGAGTTCTGGAAGTTGAAAAGTGATCTCATAA[C/T]TTCAACAAAGAAGAGTTACTTCGAGTTATCGTTTAAAAATTATATATTCGAAAGGTACTCATACTCGAGAACATT (SEQ ID NO: 9) |
| SNP_10 | 23,706,444 | CC | TT | CT | CTCRATCTTCTTCTTTTCTTTTATCTAATAAAACCTAAAAGAAGAAGATAGGGTTTAGGGTATCATTTGGTTTC[C/T]TACGGTTATTGTAATTGTTTAGAGTTGATCGCTAATTGTAACAATAATTGTGACARATTCATATTTCTCAAACTG (SEQ ID NO: 10) |
| SNP_11 | 24,104,682 | TT | GG | TG | GTTTCTGTCTGCTAATAACCTTGGAATTCTTTTGTCATACTCATACAAGACTCAACAATAAATTTGACTTTCTAG[G/T]ATGGATTGATACGAAGATTAGATGCTTTATGTTTGCAAATGATAAATTGCAACCTATTAGTTCTCGTCTCTTCA (SEQ ID NO: 11) |
| SNP_12 | 24,399,990 | AA | GG | AG | ACAAGAGTTTAAAAGGCCACAATGCAAGGCCAAACACCTTTTCACTATTTAGAAAAGCTGATTTAGTATTAAAC[A/G]TAATAGAGGCGTCAATCTTCCATTTAAGGTGATCCGGGCAATCAAGAGGARTCCAAGAATTAAGAATTTCCAGCA (SEQ ID NO: 12) |

TABLE 5-continued

SNP markers for QTL3.1 introgression fragment

| SNP marker | Physical position of the SNP (base number) | Genotype of introgression on fragment (homozygous), i.e. this is the genotype of the wild relative of cucumber or donor | Genotype of recurrent parent lacking introgression (HMRKC), i.e. this is the genotype of cultivated cucumber | Genotype of hybrid (heterozygous for the introgression fragment comprosming QTL3.1) | Genomic sequence compromising the SNP (highlighted in bold) |
|---|---|---|---|---|---|
| SNP_13 | 24,506,922 | TT | CC | TC | CAATGAACAATTGGGGATTAGACAAAAAGAGAAGAAGCACAATCAAGGAGTATTAGTTTATTTAAGGAAGGAGG[C/T]CACTCAAGAGTCAAACAAACGTAAAACCAGGTCCTTTCATTACAACAATAATGACAAACTCATTGAAATGATACA (SEQ ID NO: 13) |
| SNP_14 | 24,552,703 | AA | GG | AG | TGTTTGGCCTCTTACTGGGATTCTATTTAAAATATTTCCTTCCTGTATGATGACTACTTTTGTTTCTTCCTCCC[A/G]TCGAAATTTTTTGTGTGTTATCTGACAAGGGAAAAGAAATTTGCAAACTCGTTCCTTCCTGTTCATGATTATGGA (SEQ ID NO: 14) |
| SNP_15 | 24,700,359 | CC | TT | CT | TCCAACCATCACTTCCTCGATGCACTGCAATAGAACTTCTCGTTTCACAACTCCGTCGCTGTTAGCAAGAGCTT[C/T]GAGACCTACTTTCCAGACATCGGTGATGAACTTAGCGTTTGTTGTTTGGTCAGTCCATCCAGGCACTGTGACCAT (SEQ ID NO: 15) |
| SNP_16 | 24,892,666 | CC | TT | CT | TTCTCACTTAAAATTTCAGTTCCTTCATTTTGAAATTTTGTTCAATTTTAACTCATAGTGTAAGATTCAAATCA[C/T]GAGTCACCTTAGGCGATAAAAGGATTATATGAAGAACTCTCACCTCGAGAAGAGGCTTACTTCATCAAAAAATAA (SEQ ID NO: 16) |
| SNP_17 | 25,402,260 | GG | AA | GA | TGCACTTTGAACCTTGCACATTGCTTGTATTCACAAATTTCAGAACTGGCTCTTTATAATTCCACAGGCATAAT[A/G]CACTCATGAACAAATTAAACAACTAACCTAGAAATGTATTCCTCTCCTCTGGTTTTTTGTTTGTATGTGCAAGTG (SEQ ID NO: 17) |
| SNP_18 | 25,500,392 | CC | TT | CT | ACTGCCATTGCAACCTCAAGCTTTGCAGCGATGTGGTTTGAGATGCAAGCGGTGCAGAATGTATGTGTACATAC[C/T]CTGTTGGTGAACATTTGGGAATGGGATTTTGCGTCTGTACAGATTGAACAGAGAAGTTGGGAGGTAGAAGAGTGG (SEQ ID NO: 18) |

TABLE 5-continued

SNP markers for QTL3.1 introgression fragment

| SNP marker | Physical position of the SNP (base number) | Genotype of introgression on fragment (homozygous), i.e. this is the genotype of the wild relative of cucumber or donor | Genotype of recurrent parent lacking introgression (HMRKC), i.e. this is the genotype of cultivated cucumber | Genotype of hybrid (heterozygous for the introgression fragment compromsing QTL3.1) | Genomic sequence compromising the SNP (highlighted in bold) |
|---|---|---|---|---|---|
| SNP_19 | 25,578,888 | GG | AA | GA | TTCGTGCCAAAACGCCCAA TTTTGAGCTTCCAGCTGGC TGGACAGTGGCTCAAACTC TTCCAAAATTCAAATCT[A/G] GTATCAAAATGTAATG GGTAATGTTGTTAAACTCA AGTCTAACTTAATGGATAT TCAAAATTTCAAGAAAACT CA (SEQ ID NO: 19) |
| SNP_20 | 25,703,869 | CC | TT | CT | ATTGGGAACTTTTGGAGCT GAGGTTGCTGATTTGGTCG AAGGGGTAAGATGCTGCAC CATCCACACTTTCTTTG[C/T] CATCAAATAGATGGCT TAGGCATAGAATCATAATG GAAAAACTTATTATGTTTT CTTTTGAAGAAGAAARTTG CA (SEQ ID NO: 20) |
| SNP_21 | 25,729,729 | AA | CC | AC | TCCWATTCTTCACCTTCCA CATATTTGTTGAAACTAGG AAACTAAATCTAATAAAAT AACCTCCCTTAACACTT[A/C] AGGGATCCTAACAATA TTCTGTTCCTCTCACTCTC TCTGATGCAGAGTAAACTT GTAATTTGGCTGTTTGTAC AG (SEQ ID NO: 21) |
| SNP_22 | 25,899,925 | TT | CC | TC | CTCTAAGTCTGCAATGTGC AAGATAGATCACTGCTTGA AACTTGCTGATACATGAAA TGTCAAAATTTCTTATG[C/T] AGTACAATCTGAATTG TAACATAGGTGTAAATAGA ATCTCTTCATTTGGGATTT AGAAAGAAATAATTAGAAG AA (SEQ ID NO: 22) |
| SNP_23 | 26,303,326 | CC | TT | CT | CCAACAATCAATTGACAGG TACAATCTCTGAAACACAT TTTTCAAACCTAAGCAAGC TGAGAATCTTACACCTA[C/T] CTTCAAATTCTTTGAG ATTAAATGTCAGTGCAAAT TGGGTTCCTCCATTTCAAG TCAGAAACCTTGACATGGG TT (SEQ ID NO: 23) |
| SNP_24 | 26,704,926 | GG | AA | GA | AGAACTAGGACATCCTCGT GTTACCTTTAGAATAAATC ACATTTTCAAGGGCCAATA AACTACAATTAGCTATC[A/G] ATTTTGGAATTCAAGT AACAAAAACCGATCAAAAG CTCTATAACTGGTTTCATA TGATGCTATGAMTTAATTT TG (SEQ ID NO: 24) |

TABLE 5-continued

SNP markers for QTL3.1 introgression fragment

| SNP marker | Physical position of the SNP (base number) | Genotype of introgression on fragment (homozygous), i.e. this is the genotype of the wild relative of cucumber or donor | Genotype of recurrent parent lacking introgression (HMRKC), i.e. this is the genotype of cultivated cucumber | Genotype of hybrid (heterozygous for the introgression fragment compromsing QTL3.1) | Genomic sequence compromising the SNP (highlighted in bold) |
|---|---|---|---|---|---|
| SNP_25 | 26,912,250 | GG | AA | GA | GATGATAKACTAAAAACAT GCTACACAAAACAGTATTT ATTTGAAATAAAATGCTTT TGATAGATTGCAAGTGA[A/G] TATTGITGAAGCAAAT GTTTTCTTCCAGAGAGCAA TTGAAATAATTGATTTGAA AACAATTTTGAGAGGATGT TG (SEQ ID NO: 25) |
| SNP_26 | 27,179,673 | GG | AA | GA | ctcgggtatttggcattta gaatcgtcttctgcccgta tttcctccacgcgtgccca tcgtccactaggtcgcagc tttctcttgcccaactctg gcaactcttcctgcaaatt tcaattataaatattttta ttctaaatacaattctccc aaattctctattattcatc ttatgatcaactatatatt aaacttagtttaaattaat agaaaacctagctaccttc tcttatagcaaccccctgcg atc[A/G]ttattaggggt ggagctcttgcaactgtct ccagattcctcggattttc tactaccatgatcctcggg tgagtccacaatagagcca tttatgtcatcggagtcgc agcgatgattcaagatgga aagtgttttggagaaagag gataggattctggtgagt (SEQ ID NO: 26) |
| SNP_27 | 27,233,985 | AA | GG | GA | AAATTGGGAGATGAATTTG GATAAAAGAGAAAAACAGA ACAAGGAAGAAAAAGAAAT ATGTCATAAAAATTGGC[A/G] TAAATGTAAAAGATGT ACAAATGTATCCAATTGGA AGAGTAAGAGAGGAAACAG AGGAATTAGCAATAACATT GC (SEQ ID NO: 27) |

The invention claimed is:

1. A cultivated *Cucumis sativus* var. *sativus* plant, or plant cell, tissue, plant part or seed thereof, comprising an introgression fragment on chromosome 3 in homozygous or heterozygous form, wherein said introgression fragment is the fragment as found on chromosome 3 in seeds of which a representative sample has been deposited under accession number NCIMB 42346, wherein said introgression fragment comprises a Quantitative Trait Locus (QTL) that confers an increase in cucumber fruit yield, and wherein said introgression fragment comprises at least one of the following markers:

a) the TC or TT genotype for the Single Nucleotide Polymorphism marker SNP_01 at nucleotide 75 of SEQ ID NO: 1;

b) the TC or TT genotype for the Single Nucleotide Polymorphism marker SNP_02 at nucleotide 75 of SEQ ID NO: 2;

c) the TC or TT genotype for the Single Nucleotide Polymorphism marker SNP_03 at nucleotide 75 of SEQ ID NO: 3;

d) the TC or TT genotype for the Single Nucleotide Polymorphism marker SNP_04 at nucleotide 75 of SEQ ID NO: 4;

e) the GA or GG genotype for the Single Nucleotide Polymorphism marker SNP_05 at nucleotide 75 of SEQ ID NO: 5;

f) the TC or TT genotype for the Single Nucleotide Polymorphism marker SNP_06 at nucleotide 75 of SEQ ID NO: 6;

g) the TC or TT genotype for the Single Nucleotide Polymorphism marker SNP_07 at nucleotide 75 of SEQ ID NO: 7;
h) the TC or TT genotype for the Single Nucleotide Polymorphism marker SNP_08 at nucleotide 75 of SEQ ID NO: 8;
i) the CT or CC genotype for the Single Nucleotide Polymorphism marker SNP_09 at nucleotide 75 of SEQ ID NO: 9;
j) the CT or CC genotype for the Single Nucleotide Polymorphism marker SNP_10 at nucleotide 75 of SEQ ID NO: 10;
k) the TG or TT genotype for the Single Nucleotide Polymorphism marker SNP_11 at nucleotide 75 of SEQ ID NO: 11;
l) the AG or AA genotype for the Single Nucleotide Polymorphism marker SNP_12 at nucleotide 75 of SEQ ID NO: 12;
m) the TC or TT genotype for the Single Nucleotide Polymorphism marker SNP_13 at nucleotide 75 of SEQ ID NO: 13;
n) the AG or AA genotype for the Single Nucleotide Polymorphism marker SNP_14 at nucleotide 75 of SEQ ID NO: 14;
o) the CT or CC genotype for the Single Nucleotide Polymorphism marker SNP_15 at nucleotide 75 of SEQ ID NO: 15;
p) the CT or CC genotype for the Single Nucleotide Polymorphism marker SNP_16 at nucleotide 75 of SEQ ID NO: 16;
q) the GA or GG genotype for the Single Nucleotide Polymorphism marker SNP_17 at nucleotide 75 of SEQ ID NO: 17;
r) the CT or CC genotype for the Single Nucleotide Polymorphism marker SNP_18 at nucleotide 75 of SEQ ID NO: 18;
s) the GA or GG genotype for the Single Nucleotide Polymorphism marker SNP_19 at nucleotide 75 of SEQ ID NO: 19;
t) the CT or CC genotype for the Single Nucleotide Polymorphism marker SNP_20 at nucleotide 75 of SEQ ID NO: 20;
u) the AC or AA genotype for the Single Nucleotide Polymorphism marker SNP_21 at nucleotide 75 of SEQ ID NO: 21;
v) the TC or TT genotype for the Single Nucleotide Polymorphism marker SNP_22 at nucleotide 75 of SEQ ID NO: 22;
w) the CT or TT genotype for the Single Nucleotide Polymorphism marker SNP_23 at nucleotide 75 of SEQ ID NO: 23;
x) the GA or GG genotype for the Single Nucleotide Polymorphism marker SNP_24 at nucleotide 75 of SEQ ID NO: 24;
y) the GA or GG genotype for the Single Nucleotide Polymorphism marker SNP_25 at nucleotide 75 of SEQ ID NO: 25;
z) the GA or GG genotype for the Single Nucleotide Polymorphism marker SNP_26 at nucleotide 251 of SEQ ID NO: 26; or
aa) the AG or AA genotype for the Single Nucleotide Polymorphism marker SNP_27 at nucleotide 75 of SEQ ID NO: 27.

2. The plant according to claim 1, wherein said increase in cucumber fruit yield is phenotypically expressed as a significantly higher average number of fruits per plant (FrPP) of the plant line comprising the introgression fragment compared to the genetic control line lacking the introgression fragment when grown under the same environment and/or a significantly higher average fruit weight per plant (GrPP) of the plant line comprising the introgression fragment compared to the genetic control line lacking the introgression fragment when grown under the same environment.

3. The plant according to claim 1, wherein said introgression fragment on chromosome 3 comprises at least 2 of the following markers:
a) the TC or TT genotype for the Single Nucleotide Polymorphism marker SNP_01 at nucleotide 75 of SEQ ID NO: 1;
b) the TC or TT genotype for the Single Nucleotide Polymorphism marker SNP_02 at nucleotide 75 of SEQ ID NO: 2;
c) the TC or TT genotype for the Single Nucleotide Polymorphism marker SNP_03 at nucleotide 75 of SEQ ID NO: 3;
d) the TC or TT genotype for the Single Nucleotide Polymorphism marker SNP_04 at nucleotide 75 of SEQ ID NO: 4;
e) the GA or GG genotype for the Single Nucleotide Polymorphism marker SNP_05 at nucleotide 75 of SEQ ID NO: 5;
f) the TC or TT genotype for the Single Nucleotide Polymorphism marker SNP_06 at nucleotide 75 of SEQ ID NO: 6;
g) the TC or TT genotype for the Single Nucleotide Polymorphism marker SNP_07 at nucleotide 75 of SEQ ID NO: 7;
h) the TC or TT genotype for the Single Nucleotide Polymorphism marker SNP_08 at nucleotide 75 of SEQ ID NO: 8;
i) the CT or CC genotype for the Single Nucleotide Polymorphism marker SNP_09 at nucleotide 75 of SEQ ID NO: 9;
j) the CT or CC genotype for the Single Nucleotide Polymorphism marker SNP_10 at nucleotide 75 of SEQ ID NO: 10;
k) the TG or TT genotype for the Single Nucleotide Polymorphism marker SNP_11 at nucleotide 75 of SEQ ID NO: 11;
l) the AG or AA genotype for the Single Nucleotide Polymorphism marker SNP_12 at nucleotide 75 of SEQ ID NO: 12;
m) the TC or TT genotype for the Single Nucleotide Polymorphism marker SNP_13 at nucleotide 75 of SEQ ID NO: 13;
n) the AG or AA genotype for the Single Nucleotide Polymorphism marker SNP_14 at nucleotide 75 of SEQ ID NO: 14;
o) the CT or CC genotype for the Single Nucleotide Polymorphism marker SNP_15 at nucleotide 75 of SEQ ID NO: 15;
p) the CT or CC genotype for the Single Nucleotide Polymorphism marker SNP_16 at nucleotide 75 of SEQ ID NO: 16;
q) the GA or GG genotype for the Single Nucleotide Polymorphism marker SNP_17 at nucleotide 75 of SEQ ID NO: 17;
r) the CT or CC genotype for the Single Nucleotide Polymorphism marker SNP_18 at nucleotide 75 of SEQ ID NO: 18;
s) the GA or GG genotype for the Single Nucleotide Polymorphism marker SNP_19 at nucleotide 75 of SEQ ID NO: 19;

t) the CT or CC genotype for the Single Nucleotide Polymorphism marker SNP_20 at nucleotide 75 of SEQ ID NO: 20;

u) the AC or AA genotype for the Single Nucleotide Polymorphism marker SNP_21 at nucleotide 75 of SEQ ID NO: 21;

v) the TC or TT genotype for the Single Nucleotide Polymorphism marker SNP_22 at nucleotide 75 of SEQ ID NO: 22;

w) the CT or TT genotype for the Single Nucleotide Polymorphism marker SNP_23 at nucleotide 75 of SEQ ID NO: 23;

x) the GA or GG genotype for the Single Nucleotide Polymorphism marker SNP_24 at nucleotide 75 of SEQ ID NO: 24;

y) the GA or GG genotype for the Single Nucleotide Polymorphism marker SNP_25 at nucleotide 75 of SEQ ID NO: 25;

z) the GA or GG genotype for the Single Nucleotide Polymorphism marker SNP_26 at nucleotide 251 of SEQ ID NO: 26; and/or aa) the AG or AA genotype for the Single Nucleotide Polymorphism marker SNP_27 at nucleotide 75 of SEQ ID NO: 27.

4. The plant according to claim 1, comprising the QTL and comprising at least 1, 2, 3, 4 or 5 of the following markers from one of a), b), c) or d):

a) the TC or TT genotype for the Single Nucleotide Polymorphism marker SNP_01 at nucleotide 75 of SEQ ID NO: 1; the TC or TT genotype for the Single Nucleotide Polymorphism marker SNP_02 at nucleotide 75 of SEQ ID NO: 2; the TC or TT genotype for the Single Nucleotide Polymorphism marker SNP_03 at nucleotide 75 of SEQ ID NO: 3; the TC or TT genotype for the Single Nucleotide Polymorphism marker SNP_04 at nucleotide 75 of SEQ ID NO: 4; the GA or GG genotype for the Single Nucleotide Polymorphism marker SNP_05 at nucleotide 75 of SEQ ID NO: 5; the TC or TT genotype for the Single Nucleotide Polymorphism marker SNP_06 at nucleotide 75 of SEQ ID NO: 6; the TC or TT genotype for the Single Nucleotide Polymorphism marker SNP_07 at nucleotide 75 of SEQ ID NO: 7; the TC or TT genotype for the Single Nucleotide Polymorphism marker SNP_08 at nucleotide 75 of SEQ ID NO: 8; the CT or CC genotype for the Single Nucleotide Polymorphism marker SNP_09 at nucleotide 75 of SEQ ID NO: 9; the CT or CC genotype for the Single Nucleotide Polymorphism marker SNP_10 at nucleotide 75 of SEQ ID NO: 10; or b) the CT or CC genotype for the Single Nucleotide Polymorphism marker SNP_10 at nucleotide 75 of SEQ ID NO: 10; the TG or TT genotype for the Single Nucleotide Polymorphism marker SNP_11 at nucleotide 75 of SEQ ID NO: 11; the AG or AA genotype for the Single Nucleotide Polymorphism marker SNP_12 at nucleotide 75 of SEQ ID NO: 12; the TC or TT genotype for the Single Nucleotide Polymorphism marker SNP_13 at nucleotide 75 of SEQ ID NO: 13; the AG or AA genotype for the Single Nucleotide Polymorphism marker SNP_14 at nucleotide 75 of SEQ ID NO: 14; the CT or CC genotype for the Single Nucleotide Polymorphism marker SNP_15 at nucleotide 75 of SEQ ID NO: 15; the CT or CC genotype for the Single Nucleotide Polymorphism marker SNP_16 at nucleotide 75 of SEQ ID NO: 16; the GA or GG genotype for the Single Nucleotide Polymorphism marker SNP_17 at nucleotide 75 of SEQ ID NO: 17; the CT or CC genotype for the Single Nucleotide Polymorphism marker SNP_18 at nucleotide 75 of SEQ ID NO: 18; the GA or GG genotype for the Single Nucleotide Polymorphism marker SNP_19 at nucleotide 75 of SEQ ID NO: 19; the CT or CC genotype for the Single Nucleotide Polymorphism marker SNP_20 at nucleotide 75 of SEQ ID NO: 20; or c) the CT or CC genotype for the Single Nucleotide Polymorphism marker SNP_20 at nucleotide 75 of SEQ ID NO: 20; the AC or AA genotype for the Single Nucleotide Polymorphism marker SNP_21 at nucleotide 75 of SEQ ID NO: 21; the TC or TT genotype for the Single Nucleotide Polymorphism marker SNP_22 at nucleotide 75 of SEQ ID NO: 22; the CT or TT genotype for the Single Nucleotide Polymorphism marker SNP_23 at nucleotide 75 of SEQ ID NO: 23; the GA or GG genotype for the Single Nucleotide Polymorphism marker SNP_24 at nucleotide 75 of SEQ ID NO: 24; the GA or GG genotype for the Single Nucleotide Polymorphism marker SNP_25 at nucleotide 75 of SEQ ID NO: 25; the GA or GG genotype for the Single Nucleotide Polymorphism marker SNP_26 at nucleotide 251 of SEQ ID NO: 26; the AG or AA genotype for the Single Nucleotide Polymorphism marker SNP_27 at nucleotide 75 of SEQ ID NO: 27; or d) the TC or TT genotype for the Single Nucleotide Polymorphism marker SNP_06 at nucleotide 75 of SEQ ID NO: 6; the TC or TT genotype for the Single Nucleotide Polymorphism marker SNP_07 at nucleotide 75 of SEQ ID NO: 7; the TC or TT genotype for the Single Nucleotide Polymorphism marker SNP_08 at nucleotide 75 of SEQ ID NO: 8; the CT or CC genotype for the Single Nucleotide Polymorphism marker SNP_09 at nucleotide 75 of SEQ ID NO: 9; the CT or CC genotype for the Single Nucleotide Polymorphism marker SNP_10 at nucleotide 75 of SEQ ID NO: 10; the TG or TT genotype for the Single Nucleotide Polymorphism marker SNP_11 at nucleotide 75 of SEQ ID NO: 11; the AG or AA genotype for the Single Nucleotide Polymorphism marker SNP_12 at nucleotide 75 of SEQ ID NO: 12; the TC or TT genotype for the Single Nucleotide Polymorphism marker SNP_13 at nucleotide 75 of SEQ ID NO: 13; the AG or AA genotype for the Single Nucleotide Polymorphism marker SNP_14 at nucleotide 75 of SEQ ID NO: 14; the CT or CC genotype for the Single Nucleotide Polymorphism marker SNP_15 at nucleotide 75 of SEQ ID NO: 15; the CT or CC genotype for the Single Nucleotide Polymorphism marker SNP_16 at nucleotide 75 of SEQ ID NO: 16; the GA or GG genotype for the Single Nucleotide Polymorphism marker SNP_17 at nucleotide 75 of SEQ ID NO: 17; the CT or CC genotype for the Single Nucleotide Polymorphism marker SNP_18 at nucleotide 75 of SEQ ID NO: 18; the GA or GG genotype for the Single Nucleotide Polymorphism marker SNP_19 at nucleotide 75 of SEQ ID NO: 19; the CT or CC genotype for the Single Nucleotide Polymorphism marker SNP_20 at nucleotide 75 of SEQ ID NO: 20; the AC or AA genotype for the Single Nucleotide Polymorphism marker SNP_21 at nucleotide 75 of SEQ ID NO: 21; the TC or TT genotype for the Single Nucleotide Polymorphism marker SNP_22 at nucleotide 75 of SEQ ID NO: 22; the CT or TT genotype for the Single Nucleotide Polymorphism marker SNP_23 at nucleotide 75 of SEQ ID NO: 23.

5. The plant according to claim 1, wherein the introgression fragment is in heterozygous form and the one or more SNP markers have the heterozygous SNP genotype.

6. The plant according to claim 1, wherein the introgression fragment is in homozygous form and the one or more SNP markers have the homozygous SNP genotype.

7. The plant according to claim 1, wherein the plant is of one of the following cucumber types: slicing cucumber, long cucumber, European greenhouse cucumber.

8. The plant according to claim 1, wherein the plant is a single cross F1 hybrid or an inbred line.

9. The plant according to claim 1, wherein the plant is a cultivated cucumber of the Eurasian cucumber group, the East Asian cucumber group or the Xishuangbanna cucumber group.

10. The plant according to claim 1, wherein the plant is parthenocarpic.

11. The plant according to claim 1, wherein said introgression fragment on chromosome 3 is obtainable by crossing a plant grown from seeds deposited under accession number NCIMB 42346 with another cucumber plant.

12. Seeds from which a plant according to claim 1 can be grown.

13. A cucumber fruit harvested from a plant according to claim 1.

14. A method for identifying a cultivated *C. sativus* var. *sativus* plant comprising an introgression fragment on chromosome 3, wherein said introgression fragment is as found in NCIMB 42346, or a smaller fragment derived therefrom, comprising:
   a) screening a population of cultivated *C. sativus* var. *sativus* plants using a molecular marker assay which detects at least one SNP marker from SNP_01 to SNP_27 for detecting the introgression fragment on chromosome 3; and
   b) identifying and/or selecting a plant comprising:
      i) at least 1 of the SNP markers of SNP_01 to SNP_27 for detecting the introgression fragment on chromosome 3; or
      ii) at least 2, 3, or 4 consecutive markers selected from SNP_01 to SNP_27 for detecting the introgression fragment on chromosome 3, wherein the markers are defined as follows:
   a) the TC or TT genotype for the Single Nucleotide Polymorphism marker SNP_01 at nucleotide 75 of SEQ ID NO: 1;
   b) the TC or TT genotype for the Single Nucleotide Polymorphism marker SNP_02 at nucleotide 75 of SEQ ID NO: 2;
   c) the TC or TT genotype for the Single Nucleotide Polymorphism marker SNP_03 at nucleotide 75 of SEQ ID NO: 3;
   d) the TC or TT genotype for the Single Nucleotide Polymorphism marker SNP_04 at nucleotide 75 of SEQ ID NO: 4;
   e) the GA or GG genotype for the Single Nucleotide Polymorphism marker SNP_05 at nucleotide 75 of SEQ ID NO: 5;
   f) the TC or TT genotype for the Single Nucleotide Polymorphism marker SNP_06 at nucleotide 75 of SEQ ID NO: 6;
   g) the TC or TT genotype for the Single Nucleotide Polymorphism marker SNP_07 at nucleotide 75 of SEQ ID NO: 7;
   h) the TC or TT genotype for the Single Nucleotide Polymorphism marker SNP_08 at nucleotide 75 of SEQ ID NO: 8;
   i) the CT or CC genotype for the Single Nucleotide Polymorphism marker SNP_09 at nucleotide 75 of SEQ ID NO: 9;
   j) the CT or CC genotype for the Single Nucleotide Polymorphism marker SNP_10 at nucleotide 75 of SEQ ID NO: 10;
   k) the TG or TT genotype for the Single Nucleotide Polymorphism marker SNP_11 at nucleotide 75 of SEQ ID NO: 11;
   l) the AG or AA genotype for the Single Nucleotide Polymorphism marker SNP_12 at nucleotide 75 of SEQ ID NO: 12;
   m) the TC or TT genotype for the Single Nucleotide Polymorphism marker SNP_13 at nucleotide 75 of SEQ ID NO: 13;
   n) the AG or AA genotype for the Single Nucleotide Polymorphism marker SNP_14 at nucleotide 75 of SEQ ID NO: 14;
   o) the CT or CC genotype for the Single Nucleotide Polymorphism marker SNP_15 at nucleotide 75 of SEQ ID NO: 15;
   p) the CT or CC genotype for the Single Nucleotide Polymorphism marker SNP_16 at nucleotide 75 of SEQ ID NO: 16;
   q) the GA or GG genotype for the Single Nucleotide Polymorphism marker SNP_17 at nucleotide 75 of SEQ ID NO: 17;
   r) the CT or CC genotype for the Single Nucleotide Polymorphism marker SNP_18 at nucleotide 75 of SEQ ID NO: 18;
   s) the GA or GG genotype for the Single Nucleotide Polymorphism marker SNP_19 at nucleotide 75 of SEQ ID NO: 19;
   t) the CT or CC genotype for the Single Nucleotide Polymorphism marker SNP_20 at nucleotide 75 of SEQ ID NO: 20;
   u) the AC or AA genotype for the Single Nucleotide Polymorphism marker SNP_21 at nucleotide 75 of SEQ ID NO: 21;
   v) the TC or TT genotype for the Single Nucleotide Polymorphism marker SNP_22 at nucleotide 75 of SEQ ID NO: 22;
   w) the CT or TT genotype for the Single Nucleotide Polymorphism marker SNP_23 at nucleotide 75 of SEQ ID NO: 23;
   x) the GA or GG genotype for the Single Nucleotide Polymorphism marker SNP_24 at nucleotide 75 of SEQ ID NO: 24;
   y) the GA or GG genotype for the Single Nucleotide Polymorphism marker SNP_25 at nucleotide 75 of SEQ ID NO: 25;
   z) the GA or GG genotype for the Single Nucleotide Polymorphism marker SNP_26 at nucleotide 251 of SEQ ID NO: 26; and
   aa) the AG or AA genotype for the Single Nucleotide Polymorphism marker SNP_27 at nucleotide 75 of SEQ ID NO: 27.

15. A method of producing *C. sativus* F1 hybrid plants comprising an introgression fragment conferring enhanced fruit yield comprising: a) crossing a first inbred cucumber plant comprising a recombinant chromosome 3 in homozygous form having an introgression fragment comprising an allele conferring enhanced yield, wherein said introgression fragment is as in NCIMB 42346 with a second inbred cucumber plant, and b) collecting F1 hybrid seeds from said cross, wherein the introgression fragment comprises at least one of the following markers:

a) the TC or TT genotype for the Single Nucleotide Polymorphism marker SNP_01 at nucleotide 75 of SEQ ID NO: 1;
b) the TC or TT genotype for the Single Nucleotide Polymorphism marker SNP_02 at nucleotide 75 of SEQ ID NO: 2;
c) the TC or TT genotype for the Single Nucleotide Polymorphism marker SNP_03 at nucleotide 75 of SEQ ID NO: 3;
d) the TC or TT genotype for the Single Nucleotide Polymorphism marker SNP_04 at nucleotide 75 of SEQ ID NO: 4;
e) the GA or GG genotype for the Single Nucleotide Polymorphism marker SNP_05 at nucleotide 75 of SEQ ID NO: 5;
f) the TC or TT genotype for the Single Nucleotide Polymorphism marker SNP_06 at nucleotide 75 of SEQ ID NO: 6;
g) the TC or TT genotype for the Single Nucleotide Polymorphism marker SNP_07 at nucleotide 75 of SEQ ID NO: 7;
h) the TC or TT genotype for the Single Nucleotide Polymorphism marker SNP_08 at nucleotide 75 of SEQ ID NO: 8;
i) the CT or CC genotype for the Single Nucleotide Polymorphism marker SNP_09 at nucleotide 75 of SEQ ID NO: 9;
j) the CT or CC genotype for the Single Nucleotide Polymorphism marker SNP_10 at nucleotide 75 of SEQ ID NO: 10;
k) the TG or TT genotype for the Single Nucleotide Polymorphism marker SNP_11 at nucleotide 75 of SEQ ID NO: 11;
l) the AG or AA genotype for the Single Nucleotide Polymorphism marker SNP_12 at nucleotide 75 of SEQ ID NO: 12;
m) the TC or TT genotype for the Single Nucleotide Polymorphism marker SNP_13 at nucleotide 75 of SEQ ID NO: 13;
n) the AG or AA genotype for the Single Nucleotide Polymorphism marker SNP_14 at nucleotide 75 of SEQ ID NO: 14;
o) the CT or CC genotype for the Single Nucleotide Polymorphism marker SNP_15 at nucleotide 75 of SEQ ID NO: 15;
p) the CT or CC genotype for the Single Nucleotide Polymorphism marker SNP_16 at nucleotide 75 of SEQ ID NO: 16;
q) the GA or GG genotype for the Single Nucleotide Polymorphism marker SNP_17 at nucleotide 75 of SEQ ID NO: 17;
r) the CT or CC genotype for the Single Nucleotide Polymorphism marker SNP_18 at nucleotide 75 of SEQ ID NO: 18;
s) the GA or GG genotype for the Single Nucleotide Polymorphism marker SNP_19 at nucleotide 75 of SEQ ID NO: 19;
t) the CT or CC genotype for the Single Nucleotide Polymorphism marker SNP_20 at nucleotide 75 of SEQ ID NO: 20;
u) the AC or AA genotype for the Single Nucleotide Polymorphism marker SNP_21 at nucleotide 75 of SEQ ID NO: 21;
v) the TC or TT genotype for the Single Nucleotide Polymorphism marker SNP_22 at nucleotide 75 of SEQ ID NO: 22;
w) the CT or TT genotype for the Single Nucleotide Polymorphism marker SNP_23 at nucleotide 75 of SEQ ID NO: 23;
x) the GA or GG genotype for the Single Nucleotide Polymorphism marker SNP_24 at nucleotide 75 of SEQ ID NO: 24;
y) the GA or GG genotype for the Single Nucleotide Polymorphism marker SNP_25 at nucleotide 75 of SEQ ID NO: 25;
z) the GA or GG genotype for the Single Nucleotide Polymorphism marker SNP_26 at nucleotide 251 of SEQ ID NO: 26; or
aa) the AG or AA genotype for the Single Nucleotide Polymorphism marker SNP_27 at nucleotide 75 of SEQ ID NO: 27.

16. A cultivated *Cucumis sativus* var. *sativus* plant, or plant cell, tissue, plant part or seed thereof, comprising an introgression fragment on chromosome 3 in homozygous or heterozygous form, wherein said introgression fragment is a smaller fragment derived from the fragment as found on chromosome 3 in seeds of which a representative sample has been deposited under accession number NCIMB 42346, wherein said smaller fragment comprises a Quantitative Trait Locus (QTL) that confers an increase in cucumber fruit yield and comprises markers SNP_1 to SNP_10, SNP_10 to SNP_20, SNP_20 to SNP_27, or SNP_06 to SNP_23, wherein the makers are defined as follows:
a) the TC or TT genotype for the Single Nucleotide Polymorphism marker SNP_01 at nucleotide 75 of SEQ ID NO: 1;
b) the TC or TT genotype for the Single Nucleotide Polymorphism marker SNP_02 at nucleotide 75 of SEQ ID NO: 2;
c) the TC or TT genotype for the Single Nucleotide Polymorphism marker SNP_03 at nucleotide 75 of SEQ ID NO: 3;
d) the TC or TT genotype for the Single Nucleotide Polymorphism marker SNP_04 at nucleotide 75 of SEQ ID NO: 4;
e) the GA or GG genotype for the Single Nucleotide Polymorphism marker SNP_05 at nucleotide 75 of SEQ ID NO: 5;
f) the TC or TT genotype for the Single Nucleotide Polymorphism marker SNP_06 at nucleotide 75 of SEQ ID NO: 6;
g) the TC or TT genotype for the Single Nucleotide Polymorphism marker SNP_07 at nucleotide 75 of SEQ ID NO: 7;
h) the TC or TT genotype for the Single Nucleotide Polymorphism marker SNP_08 at nucleotide 75 of SEQ ID NO: 8;
i) the CT or CC genotype for the Single Nucleotide Polymorphism marker SNP_09 at nucleotide 75 of SEQ ID NO: 9;
j) the CT or CC genotype for the Single Nucleotide Polymorphism marker SNP_10 at nucleotide 75 of SEQ ID NO: 10;
k) the TG or TT genotype for the Single Nucleotide Polymorphism marker SNP_11 at nucleotide 75 of SEQ ID NO: 11;
l) the AG or AA genotype for the Single Nucleotide Polymorphism marker SNP_12 at nucleotide 75 of SEQ ID NO: 12;
m) the TC or TT genotype for the Single Nucleotide Polymorphism marker SNP_13 at nucleotide 75 of SEQ ID NO: 13;

n) the AG or AA genotype for the Single Nucleotide Polymorphism marker SNP_14 at nucleotide 75 of SEQ ID NO: 14;
o) the CT or CC genotype for the Single Nucleotide Polymorphism marker SNP_15 at nucleotide 75 of SEQ ID NO: 15;
p) the CT or CC genotype for the Single Nucleotide Polymorphism marker SNP_16 at nucleotide 75 of SEQ ID NO: 16;
q) the GA or GG genotype for the Single Nucleotide Polymorphism marker SNP_17 at nucleotide 75 of SEQ ID NO: 17;
r) the CT or CC genotype for the Single Nucleotide Polymorphism marker SNP_18 at nucleotide 75 of SEQ ID NO: 18;
s) the GA or GG genotype for the Single Nucleotide Polymorphism marker SNP_19 at nucleotide 75 of SEQ ID NO: 19;
t) the CT or CC genotype for the Single Nucleotide Polymorphism marker SNP_20 at nucleotide 75 of SEQ ID NO: 20;
u) the AC or AA genotype for the Single Nucleotide Polymorphism marker SNP_21 at nucleotide 75 of SEQ ID NO: 21;
v) the TC or TT genotype for the Single Nucleotide Polymorphism marker SNP_22 at nucleotide 75 of SEQ ID NO: 22;
w) the CT or TT genotype for the Single Nucleotide Polymorphism marker SNP_23 at nucleotide 75 of SEQ ID NO: 23;
x) the GA or GG genotype for the Single Nucleotide Polymorphism marker SNP_24 at nucleotide 75 of SEQ ID NO: 24;
y) the GA or GG genotype for the Single Nucleotide Polymorphism marker SNP_25 at nucleotide 75 of SEQ ID NO: 25;
z) the GA or GG genotype for the Single Nucleotide Polymorphism marker SNP_26 at nucleotide 251 of SEQ ID NO: 26; and
aa) the AG or AA genotype for the Single Nucleotide Polymorphism marker SNP_27 at nucleotide 75 of SEQ ID NO: 27.

17. The plant according to claim 16, wherein the smaller fragment comprises markers SNP_1 to SNP_10.

18. The plant according to claim 16, wherein the smaller fragment comprises SNP_10 to SNP_20.

19. The plant according to claim 16, wherein the smaller fragment comprises markers SNP_20 to SNP_27.

20. The plant according to claim 16, wherein the smaller fragment comprises markers SNP_06 to SNP_23.

21. The plant according to claim 16, wherein the introgression fragment is in heterozygous form and the SNP markers have the heterozygous SNP genotype.

22. The plant according to claim 16, wherein the introgression fragment is in homozygous form and the SNP markers have the homozygous SNP genotype.

23. The plant according to claim 16, wherein the plant is of one of the following cucumber types: slicing cucumber, long cucumber, European greenhouse cucumber.

24. The plant according to claim 16, wherein the plant is a single cross F1 hybrid or an inbred line.

* * * * *